US012419191B2

(12) United States Patent
Yun et al.

(10) Patent No.: US 12,419,191 B2
(45) Date of Patent: Sep. 16, 2025

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Jin Ho Yun, Cheonan-si (KR); Nam Soo Kim, Cheonan-si (KR); Mi Young Chae, Cheonan-si (KR); Sun Hee Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 632 days.

(21) Appl. No.: 17/293,809

(22) PCT Filed: Sep. 20, 2019

(86) PCT No.: PCT/KR2019/012284
§ 371 (c)(1),
(2) Date: May 13, 2021

(87) PCT Pub. No.: WO2020/101169
PCT Pub. Date: May 22, 2020

(65) Prior Publication Data
US 2022/0020932 A1 Jan. 20, 2022

(30) Foreign Application Priority Data
Nov. 15, 2018 (KR) .................. 10-2018-0140445

(51) Int. Cl.
| | | |
|---|---|---|
| C07D 401/14 | (2006.01) | |
| C07D 403/14 | (2006.01) | |
| C07D 405/14 | (2006.01) | |
| C07D 409/14 | (2006.01) | |
| H10K 85/60 | (2023.01) | |
| H10K 50/11 | (2023.01) | |

(52) U.S. Cl.
CPC ......... *H10K 85/654* (2023.02); *C07D 403/14* (2013.01); *C07D 405/14* (2013.01); *C07D 409/14* (2013.01); *H10K 85/6572* (2023.02); *H10K 85/6574* (2023.02); *H10K 85/6576* (2023.02); *H10K 50/11* (2023.02)

(58) Field of Classification Search
None
See application file for complete search history.

(56) References Cited

U.S. PATENT DOCUMENTS

| | | | |
|---|---|---|---|
| 2012/0267620 A1* | 10/2012 | Min ................. | H10K 85/6572 257/E51.026 |
| 2018/0337348 A1* | 11/2018 | Jung ................. | H10K 85/622 |
| 2019/0198777 A1* | 6/2019 | Suzuki .............. | H10K 85/654 |
| 2020/0259098 A1* | 8/2020 | Lee ................... | H10K 85/657 |
| 2021/0047306 A1* | 2/2021 | Jung ................. | C07D 405/10 |
| 2022/0102646 A1* | 3/2022 | Kim .................. | H10K 85/6574 |
| 2022/0181558 A1* | 6/2022 | Jun ................... | C07D 403/04 |

FOREIGN PATENT DOCUMENTS

| | | | | |
|---|---|---|---|---|
| CN | 106946853 A | | 7/2017 | |
| KR | 10-2013-0025190 A | | 3/2013 | |
| KR | 10-2015-0069346 A | | 6/2015 | |
| KR | 10-2017-0113319 A | | 10/2017 | |
| KR | 20170113319 A | * | 10/2017 | ......... C07D 487/04 |
| KR | 10-2018-0010130 A | | 1/2018 | |
| KR | 10-2018-0061074 A | | 6/2018 | |
| KR | 10-1959821 B1 | | 3/2019 | |
| KR | 10-2019-0116686 A | | 10/2019 | |
| WO | WO-2013032297 A1 | * | 3/2013 | ......... C07B 59/002 |
| WO | WO-2014128945 A1 | * | 8/2014 | ......... C09K 11/06 |
| WO | WO-2015169412 A1 | * | 11/2015 | ......... C07D 251/24 |
| WO | WO-2017171420 A1 | * | 10/2017 | ......... C07D 251/24 |

OTHER PUBLICATIONS

Machine translation of WO-2014128945-A1, translation generated Aug. 2024, 12 pages. (Year: 2024).*
Machine translation of WO-2017171420-A1, translation generated Aug. 2024, 28 pages. (Year: 2024).*
Machine translation of KR-20170113319-A, translation generated Nov. 2024, 28 pages. (Year: 2024).*
Machine translation of WO-2015169412-A1, translation generated Mar. 2025, 33 pages. (Year: 2025).*
Korean Office Action for corresponding KR 10-2018-0140445 mailed Apr. 6, 2023.

* cited by examiner

*Primary Examiner* — Robert S Loewe
(74) *Attorney, Agent, or Firm* — Vorys, Sater, Seymour and Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and an electronic device comprising the organic electric element, and by employing the compound represented by Formula 1 in the organic material layer, the driving voltage of the organic electric element can be lowered, and the luminous efficiency and life time of the electric element can be improved.

13 Claims, 1 Drawing Sheet

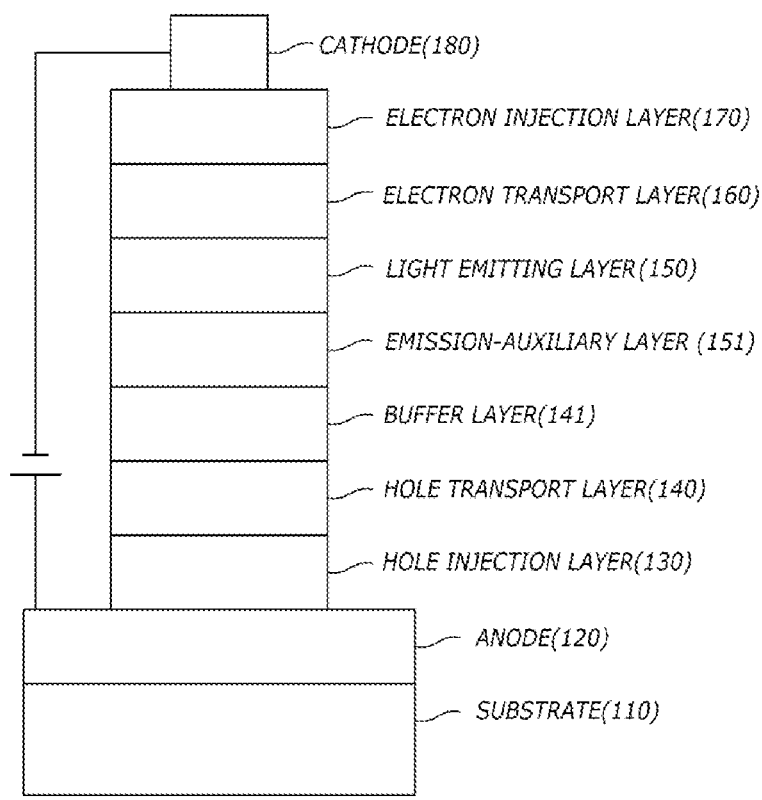

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2018-0140445, filed on Nov. 15, 2018 which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element using the same and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may comprise a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is very important factor in the portable display with a limited power source of the battery, and efficiency and life span issues must also be solved.

Efficiency, life span, driving voltage, and the like are correlated with each other. If efficiency is increased, then driving voltage is relatively lowered, and the crystallization of an organic material due to Joule heating generated during operation is reduced as driving voltage is lowered. As a result, life span tens to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, in particular, it is strongly required to develop host material of the light emitting layer.

Object, Technical Solution and Effects of the Invention

The present invention is to provide compound lowering a driving voltage, improving luminous efficiency and lifetime of the element, an organic electric element comprising the same, and an electronic device thereof.

In an aspect of the present invention, the present invention provides the compound represented by the following formula.

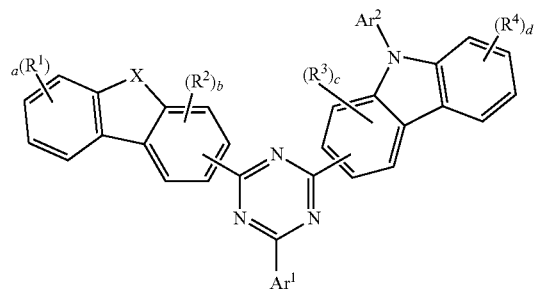

In another aspect of the present invention, the present invention provides an organic electric element using the compound represented by formula above and an electric device thereof.

By using the compound according to embodiment of the present invention, a driving voltage of element can be lowered and the luminous efficiency and lifetime of the element can be significantly improved.

BRIEF DESCRIPTION OF THE DRAWINGS

FIGURE illustrates an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

DETAILED DESCRIPTION

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like. In addition, unless otherwise stated, a fluorenyl group may be comprised in an aryl group and a fluorenylene group may be comprised in an arylene group.

Unless otherwise stated, the term "fluorenyl group" or "fluorenylene group" as used herein means univalent or bivalent functional group in which R, R' and R" are all hydrogen in the following structure, "substituted fluorenyl group" or "substituted fluorenylene group" means that at least any one of R, R' and R" is a substituent other than hydrogen, and the case where R and R' are bonded to each other to form the spiro compound together with the carbon bonded to them is comprised.

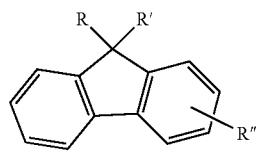

The term "spiro compound" as used herein has a spiro union which means union having one atom as the only common member of two rings. The common atom is designated as 'spiro atom'. The compounds are defined as 'monospiro-', 'dispiro-' or 'trispiro' depending on the number of spiro atoms in one compound.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein represents N, O, S, P or Si and the heterocyclic group means a monocyclic, ring assemblies, a fused polycyclic system or spiro compound containing a heteroatom.

The term "heterocyclic group" as used herein refers to a ring in which a heteroatom such as N, O, S, P, or Si is comprised instead of carbon forming the ring and it comprises a non-aromatic ring as well as an aromatic ring like "heteroaryl group" or "heteroarylene group". The term "heterocyclic group" used in the present invention may also comprise a compound comprising a heteroatom group such as $SO_2$, $P=O$, and the like, such as the following compounds, instead of carbon forming a ring.

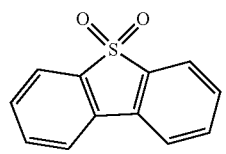 [SMILES: O=S1(=O)c2ccccc2-c2ccccc21]

The term "aliphatic ring group" as used herein refers to a cyclic hydrocarbon except for aromatic hydrocarbons, and comprises a monocyclic ring, ring assemblies, a fused polycyclic system, spiro compounds, and the like, and unless otherwise specified, it means a ring of 3 to 60 carbon atoms, but not limited thereto. For example, a fused ring formed by benzene being an aromatic ring with cyclohexane being a non-aromatic ring corresponds to aliphatic ring group.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, in the present specification, the numbers and alphabets indicating a position may be omitted when describing a compound name or a substituent name, For example, pyrido[4,3-d]pyrimidine, benzopuro[2,3-d] pyrimidine and 9,9-dimethyl-9H-fluorene can be described as pyridopyrimidine, benzofurropyrimidine and dimethylfluorene, respectively. Therefore, both benzo[g]quinoxaline and benzo[f] quinoxaline can be described as benzoquinoxaline.

In addition, unless otherwise expressed, where any formula of the present invention is represented by the following formula, the substituent according to the index may be defined as follows.

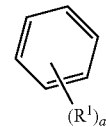

In the above formula, where a is an integer of zero, the substituent $R^1$ is absent, that is, hydrogen atoms are bonded to all the carbon constituting the benzene ring. Here, chemical formulas or compounds may be written described by omitting the indication of hydrogen bonded to carbon. In addition, one substituent $R^1$ is bonded to any carbon of the carbons forming the benzene ring when "a" is an integer of 1. Similarly, where "a" is an integer of 2 or 3, for example, as in the following formulas, substituents $R^1$s may be bonded to the carbon of the benzene ring. Also, where "a" is an integer of 4 to 6, substituents R¹s are bonded to the carbon of the benzene ring in a similar manner. Further, where "a" is an integer of 2 or more, R's may be the same or different from each other.

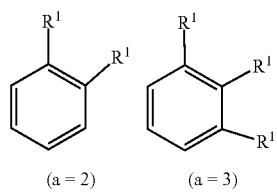

FIGURE illustrates an example of an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 stacked in sequence on the first electrode 120. Here, at least one layer of the organic material layer may be omitted, or a hole blocking layer, an electron blocking layer, an emission-auxiliary layer 151, an electron transport-auxiliary layer, a buffer layer 141, etc. may be further included in the organic material layer, and the electron transport layer 160 or the like may serve as a hole blocking layer.

In addition, although not shown, the organic electric element according to an embodiment of the present invention may further include a protective layer or a layer for improving luminous efficiency. The layer for improving luminous efficiency may be formed on one side of sides of the first electrode or one side of sides of the second electrode, wherein the one side is not facing the organic material layer.

The inventive compound employed in the organic material layer may be used as a material of a hole injection layer 130, a hole transport layer 140, an emission-auxiliary layer 151, an electron transport-auxiliary layer, an electron transport layer 160 or an electron injection layer 170, as host or dopant of a light emitting layer 150, or as a material of a layer for improving luminous efficiency. Preferably, compound according to Formula 1 of the present invention can be used as host of a light emitting layer.

On the other hand, even if the core is same or similar, the band gap, the electrical characteristics, the interface characteristics and the like may be different depending on which substituent is bonded at which position. Therefore, there is a need to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.) and the like among the respective layers of an organic material layer is achieved.

Therefore, the energy level and $T_1$ value between the respective layers of the organic material layer, inherent material properties (mobility, interfacial properties, etc.) and the like can be optimized by using compound represented by Formula 1 as host of a light emitting layer in the present invention.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or alloy on the substrate to form the anode 120, forming the organic material layer including the hole injection layer 130, the hole transport layer 140, the light emitting layer 150, the electron transport layer 160, and the electron injection layer 170 thereon, and then depositing a material which can be used as the cathode 180, thereon. In addition, an emitting auxiliary layer 151 may be formed between a hole transport layer 140 and a light emitting layer 150, and an electron transport-auxiliary layer may be formed between a light emitting layer 150 and an electron transport layer 160.

In addition, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to the present invention may be selected from group consisting of an organic electroluminescent element, an organic solar cell, an organic photo conductor, an organic transistor, an element for monochromatic illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, various kinds of computers and so on.

Hereinafter, the compound according to an aspect of the present invention will be described.

Compound according to one aspect of the present invention may be represented by Formula 1.

<Formula 1>

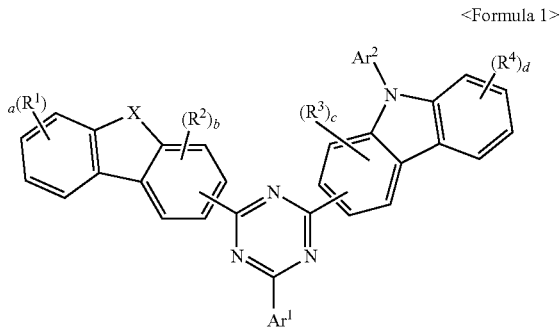

In formula 1, each of symbols may be defined as follows.

X is O, S or N(Ar³). Here, Ar³ is selected from the group consisting of a $C_6$-$C_{60}$ aryl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group.

Where Ar³ is an aryl group, the aryl group may be preferably a $C_6$-$C_{30}$ aryl group, more preferably a $C_6$-$C_{18}$ aryl group, for example, phenyl, naphthyl, biphenyl, terphenyl and the like. Where Ar³ is an alkyl group, the alkyl group may be preferably a $C_2$-$C_{20}$ alkyl group, more preferably a $C_2$-$C_{10}$ alkyl group, for example, methyl, t-butyl and the like.

R¹ to R⁴ may be each independently selected from the group consisting of hydrogen, deuterium, halogen, a cyano group, a nitro group, a $C_6$-$C_{60}$ aryl group, a $C_2$-$C_{60}$ heterocyclic group containing at least one heteroatom of O, N, S, Si, and P, a $C_3$-$C_{60}$ aliphatic ring group, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group and -L'-N(R$_a$)(R$_b$). With the proviso that the case where all of R¹ to R⁴ are hydrogen is excluded.

Also, adjacent R¹ groups, adjacent R² groups, adjacent R³ groups, or adjacent R⁴ groups together may be bonded to each other to form a ring. Here, the ring can be selected from the group consisting of a $C_6$-$C_{60}$ aromatic ring, a $C_2$-$C_{60}$ heterocyclic group containing at least one heteroatom of O, N, S, Si, and P, a $C_3$-$C_{60}$ aliphatic ring group and a combination thereof.

a and d are each an integer of 0 to 4, b and c are each an integer of 0 to 3, where they are each an integer of 2 or more, each of a plurality of R¹s, each of a plurality of R²s, each of a plurality of R³s, each of a plurality of R⁴s is the same or different from each other.

Where R¹ to R⁴ are independently an aryl group, the aryl group may be preferably a $C_6$-$C_{30}$ aryl group, more preferably a $C_6$-$C_{18}$ aryl group, for example, phenyl, naphthyl, biphenyl, terphenyl and the like. Where R¹ to R⁴ are independently a heterocyclic group, the heterocyclic group may be preferably a $C_2$-$C_{30}$ heterocyclic group, more preferably a $C_2$-$C_{18}$ heterocyclic group, for example, dibenzothiophene, dibenzofuran, carbazole, phenylcarbazole and the like. Where R¹ to R⁴ are independently an alkyl group, the alkyl group may be preferably a $C_2$-$C_{20}$ alkyl group, more preferably a $C_2$-$C_{10}$ alkyl group, for example, methyl, t-butyl and the like.

Where adjacent R¹ groups or adjacent R² groups together may be bonded to each other to form an aromatic ring, the aromatic ring may be a $C_6$-$C_{30}$ aromatic ring, more preferably a $C_6$-$C_{14}$ aromatic ring, for example, a ring such as benzene, naphthalene or phenanthrene.

Preferably, at least one of R¹ to R⁴ is the aryl group.

Ar¹ and Ar² may be independently selected from the group consisting of a $C_6$-$C_{60}$ aryl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group.

Where Ar¹ and Ar² are an aryl group, the aryl group may be preferably a $C_6$-$C_{30}$ aryl group, more preferably a $C_6$-$C_{18}$ aryl group, for example, phenyl, naphthyl, biphenyl, naphthyl substituted phenyl, anthracene, terphenyl, 9H-fluorene and the like.

L' may be selected from the group consisting of a single bond, a $C_6$-$C_{60}$ arylene group, a $C_3$-$C_{60}$ aliphatic ring, a $C_2$-$C_{60}$ heterocyclic group containing at least one heteroatom of O, N, S, Si, and P and a combination thereof.

R$_a$ and R$_b$ may be each independently selected from the group consisting of a $C_6$-$C_{60}$ aryl group, a $C_3$-$C_{60}$ aliphatic ring group, a $C_2$-$C_{60}$ heterocyclic group containing at least one heteroatom of O, N, S, Si, and P and a combination thereof.

R¹ to R⁴, Ar¹ to Ar³, L', R$_a$, R$_b$, and the ring formed by bonding adjacent groups to each other may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ arylalkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a $C_2$-$C_{20}$ heterocyclic group containing at least one heteroatom of O, N, S, Si, and P, a $C_3$-$C_{20}$ aliphatic ring, a $C_7$-$C_{20}$ arylalkyl group, $C_8$-$C_{20}$ arylalkenyl group and a combination thereof.

Formula 1 may be represented by one of Formula 2 to Formula 5.

<Formula 2>

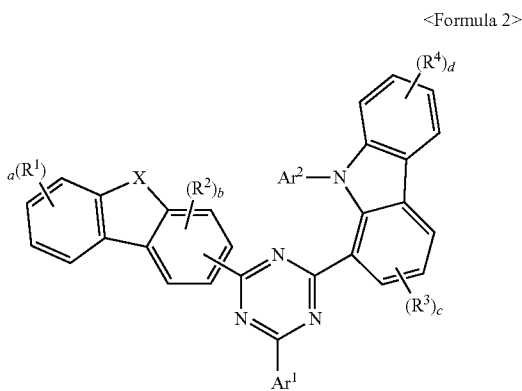

<Formula 3>

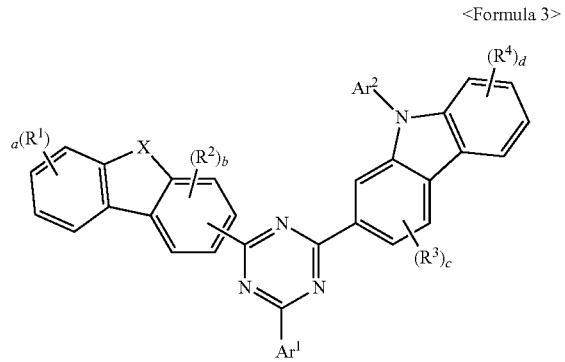

<Formula 4>

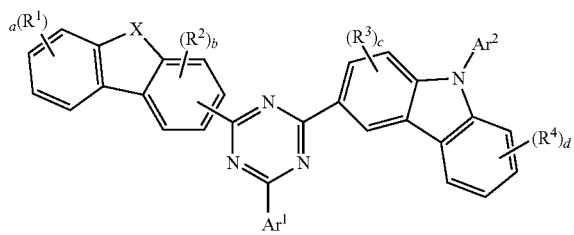

<Formula 5>

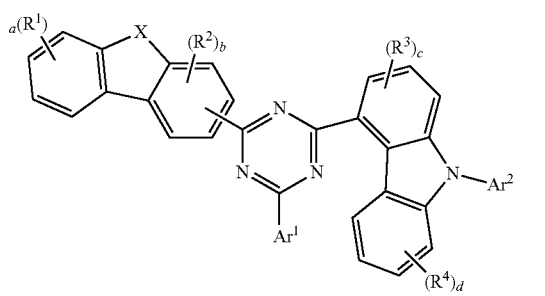

In Formulas 2 to 5, X, R¹ to R⁴, a to d, Ar¹, Ar² are the same as defined for Formula 1.

In addition, Formula 1 may be represented by one of Formula 6 to Formula 9.

<Formula 6>

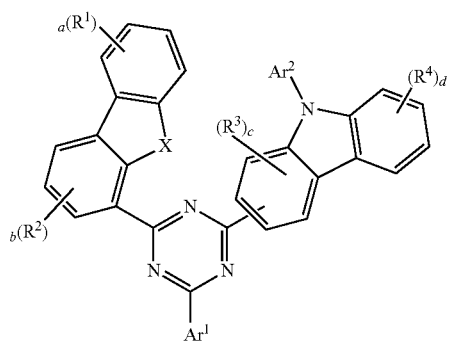

<Formula 7>

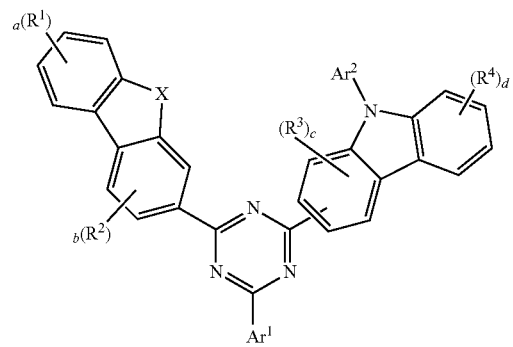

<Formula 8>

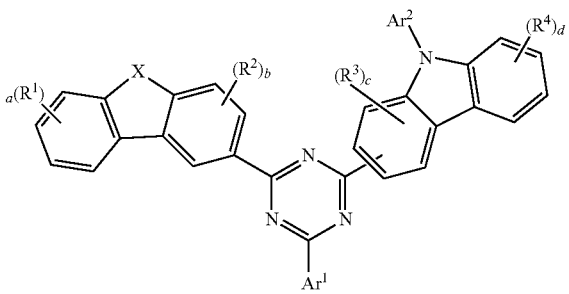

<Formula 9>

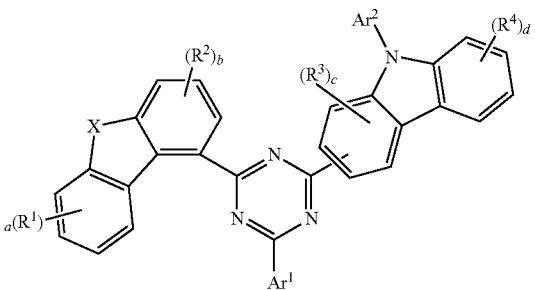

In Formulas 6 to 9, X, R¹ to R⁴, a to d, Ar¹, Ar² are the same as defined for Formula 1.

Specifically, compound represented by formula 1 may be one of the following compounds, but there is no limitation thereto.

P 1-1

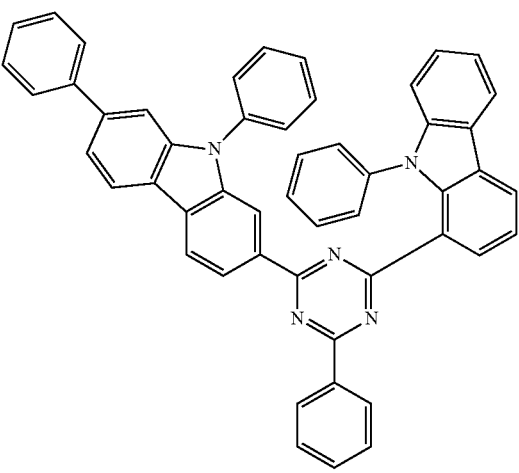

P 1-2
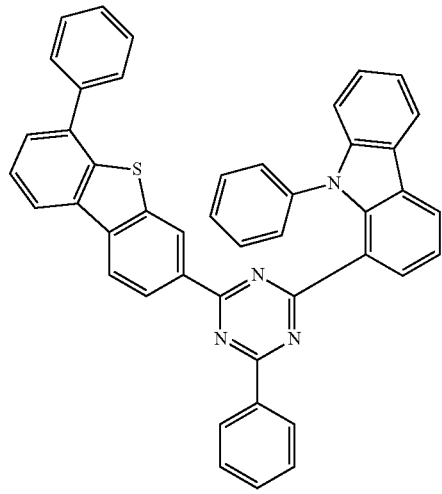
P 1-3
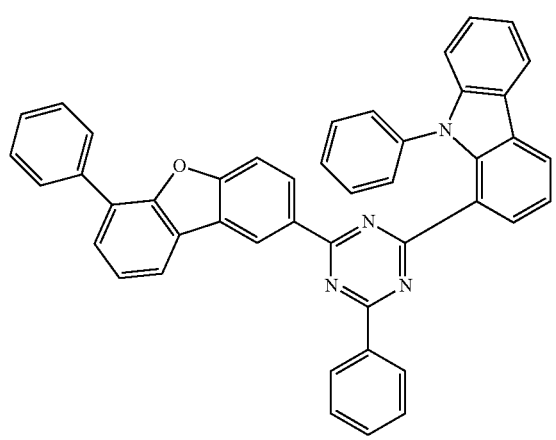
P 1-4
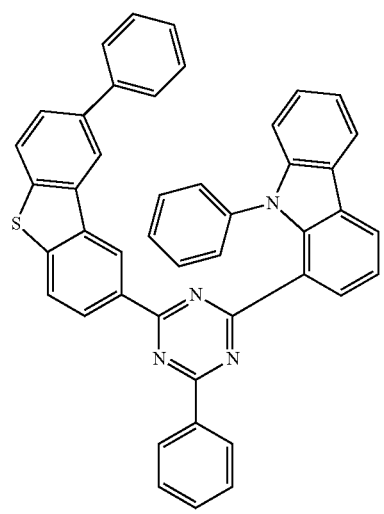
P 1-5
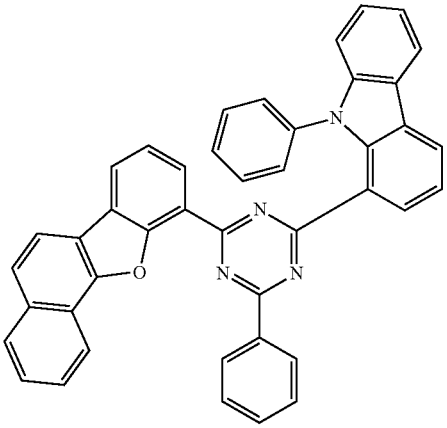
P 1-6
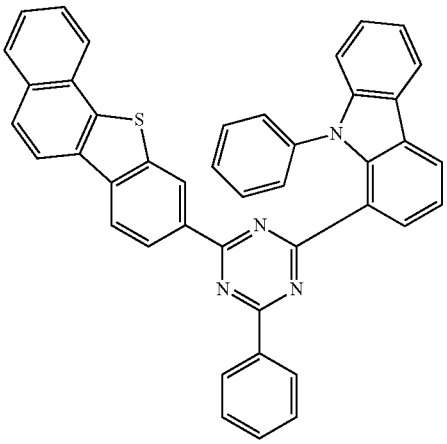
P 1-7
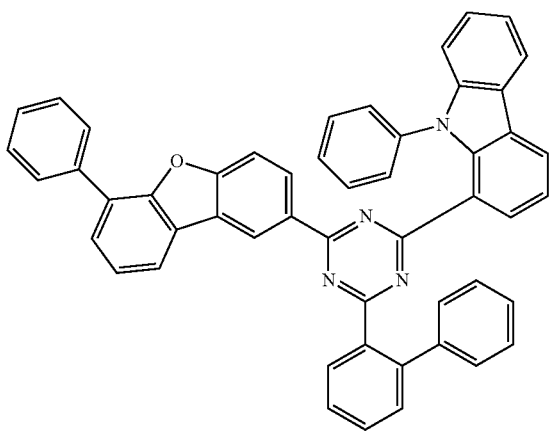

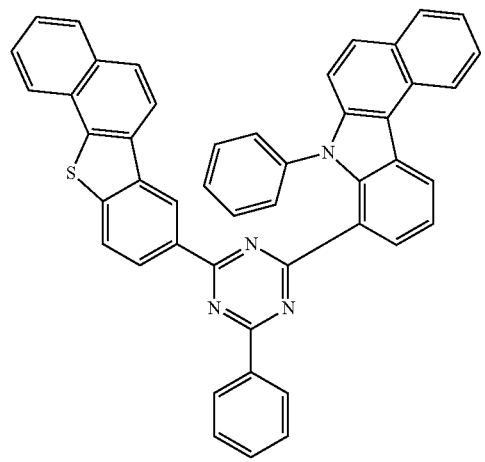
P 1-8
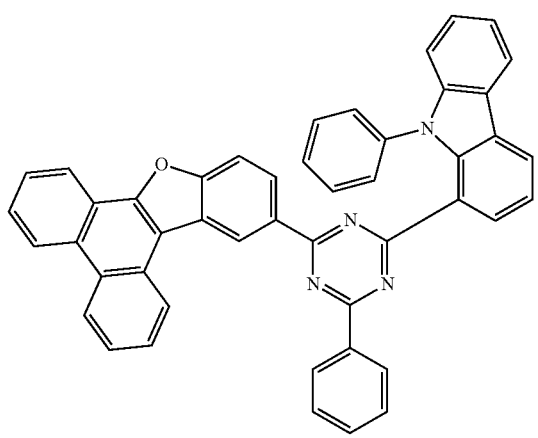
P 1-11
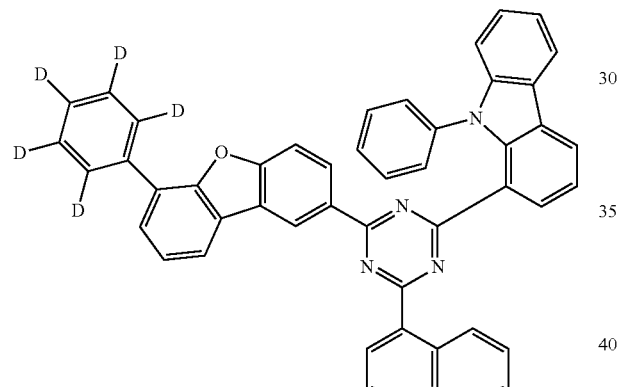
P 1-9
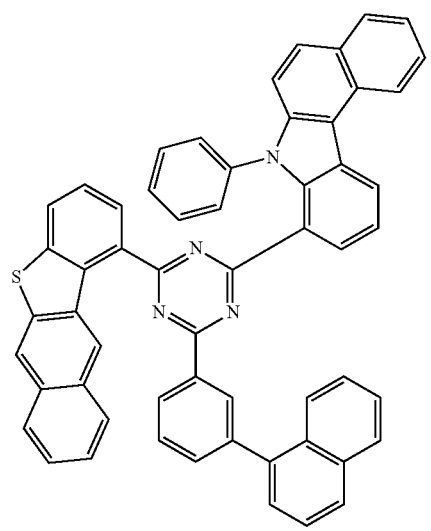
P 1-12
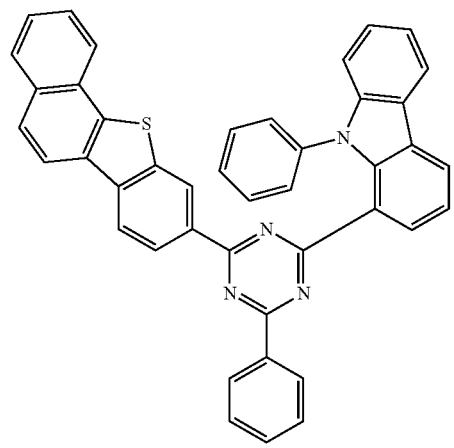
P 1-10
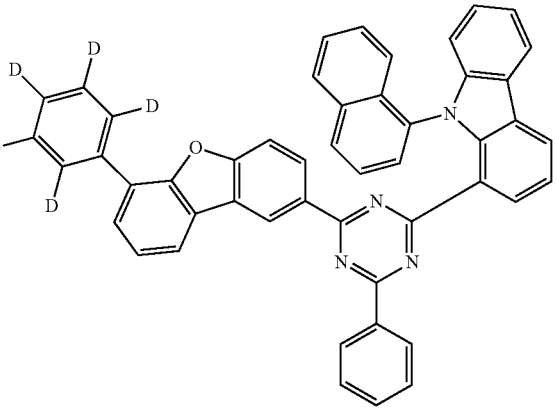
P 1-13

P 1-14
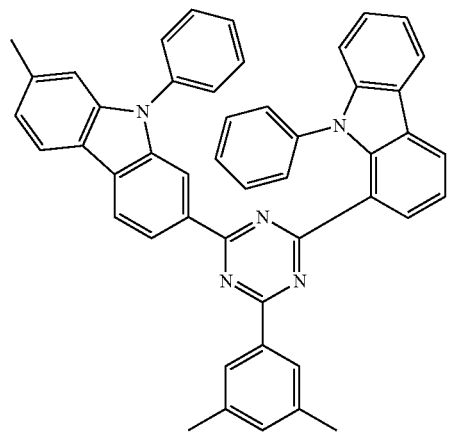
P 2-1
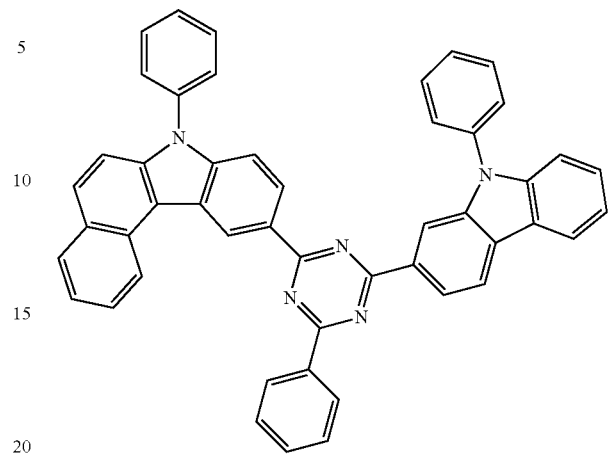
P 1-15
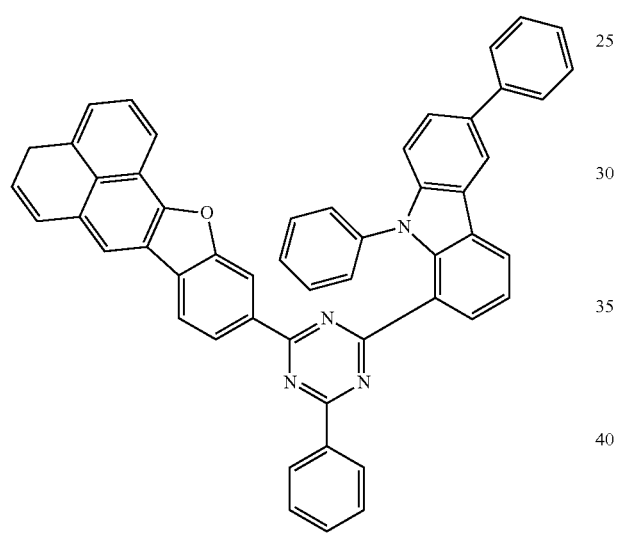
P 2-2
P 1-16
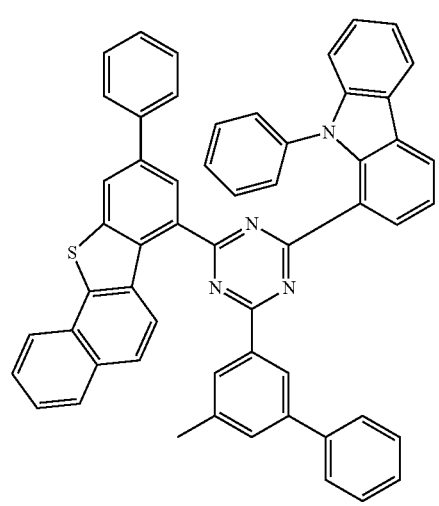
P 2-3

P 2-4
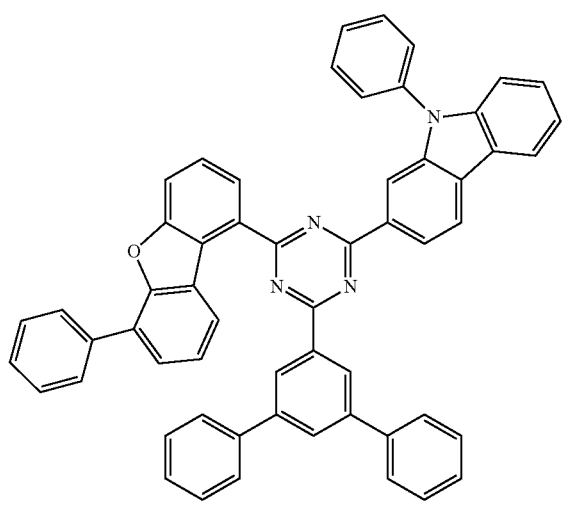
P 2-5
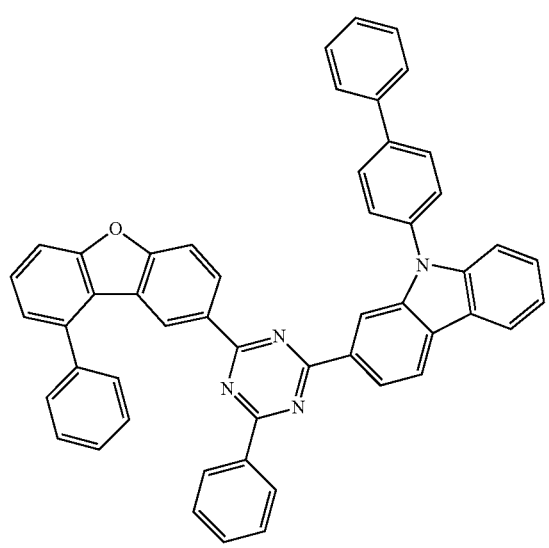
P 2-6
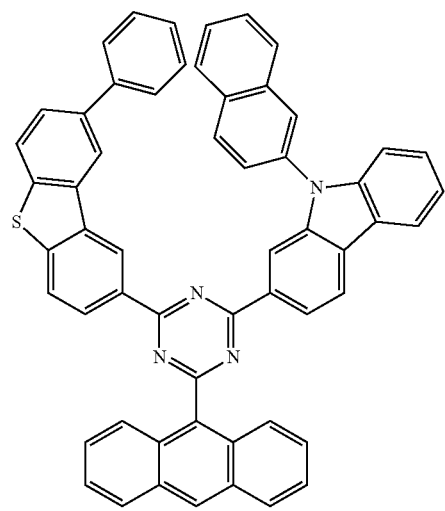
P 2-7
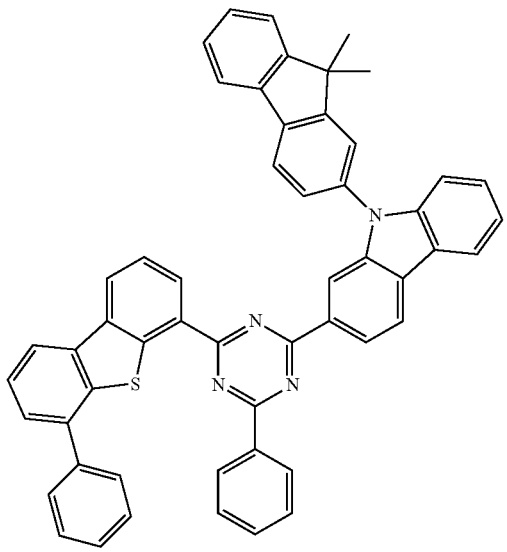
P 2-8
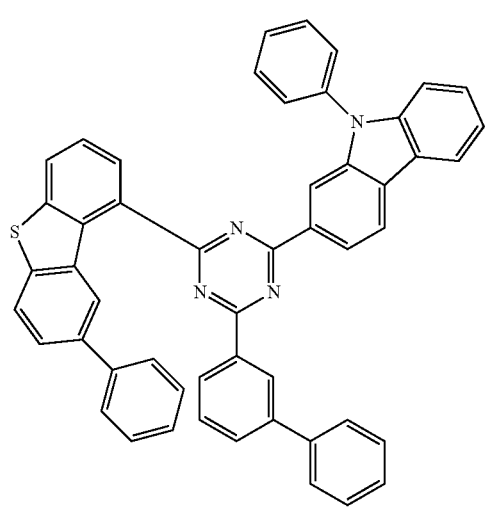
P 2-9
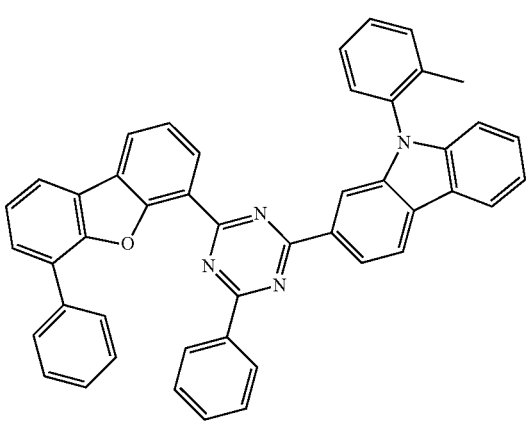

P 2-10
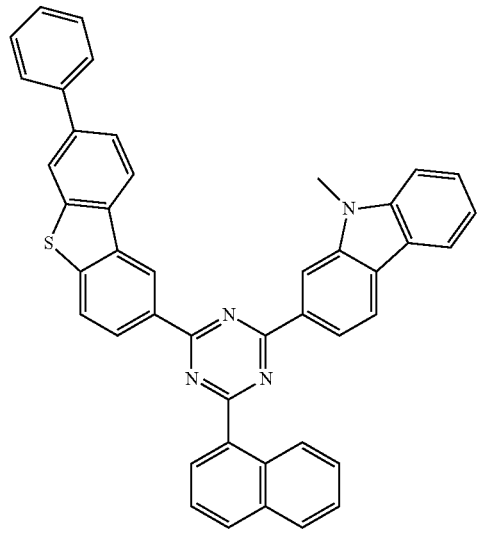
P 2-14
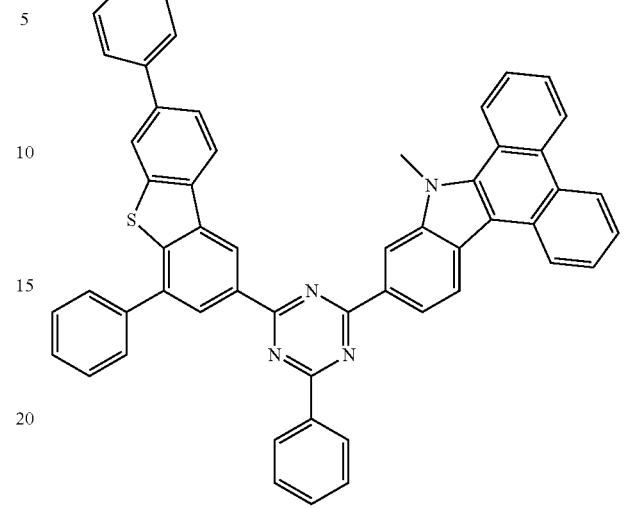
P 2-11
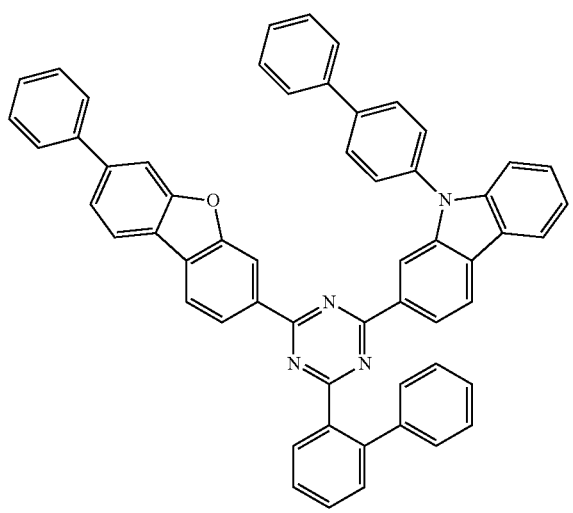
P 2-15
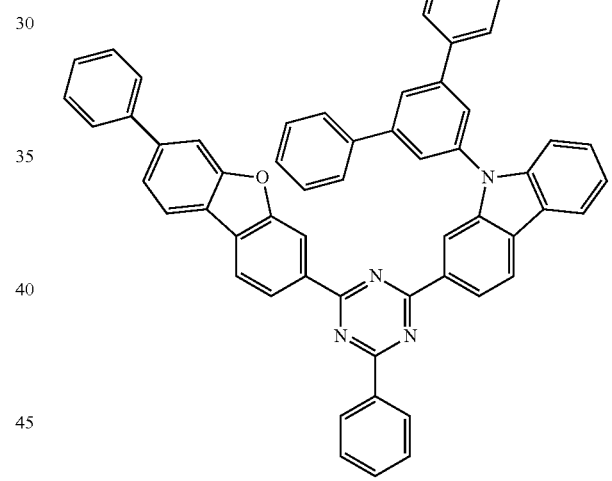
P 2-13
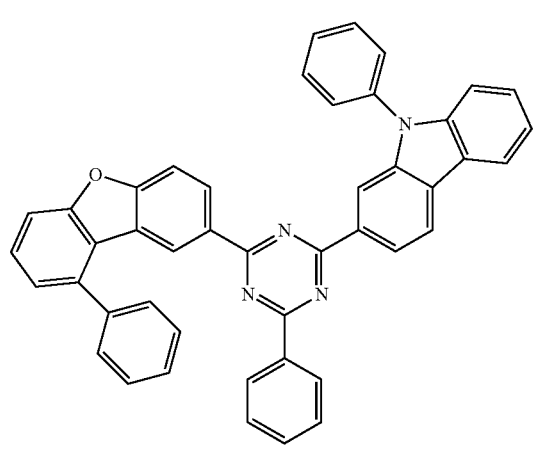
P 2-16
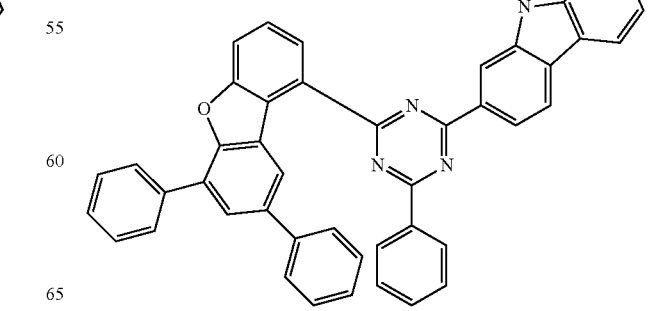

-continued
P 3-1
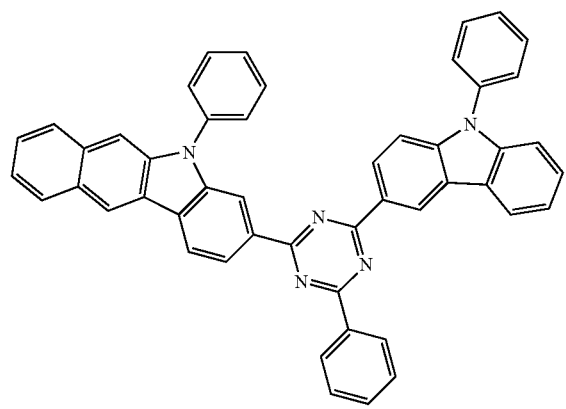
P 3-4
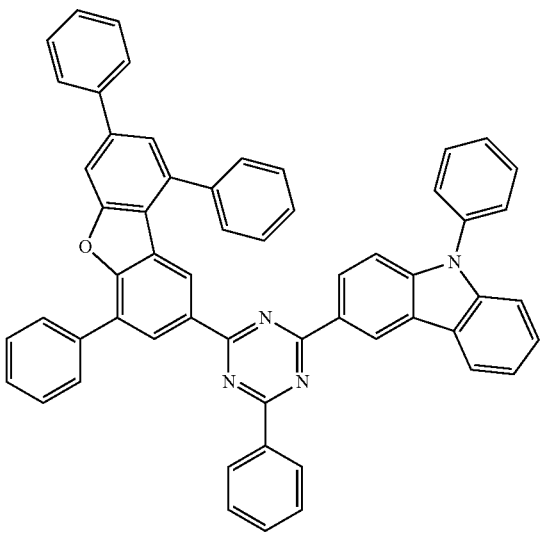
P 3-2
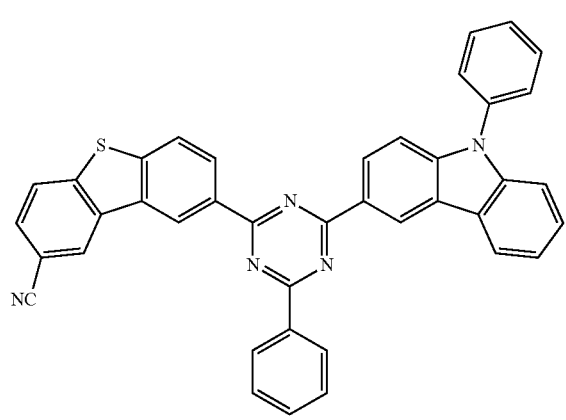
P 3-5
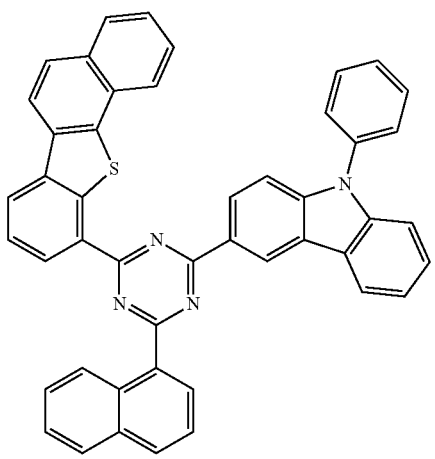
P 3-3
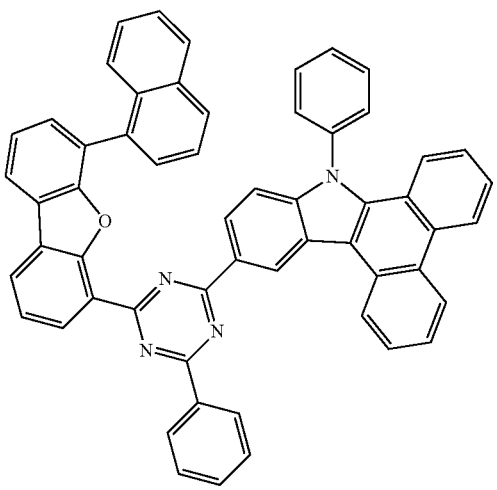
P 3-6
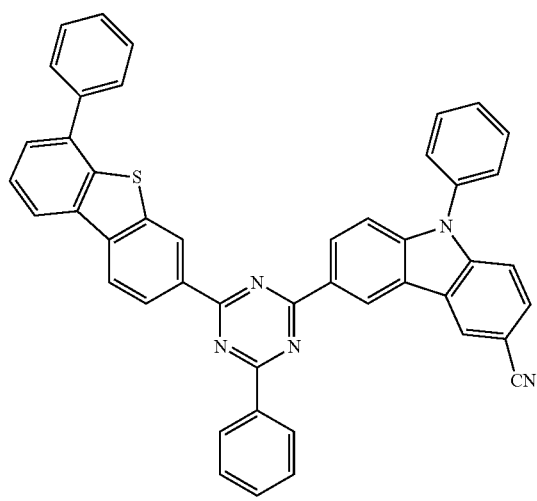

P 3-7
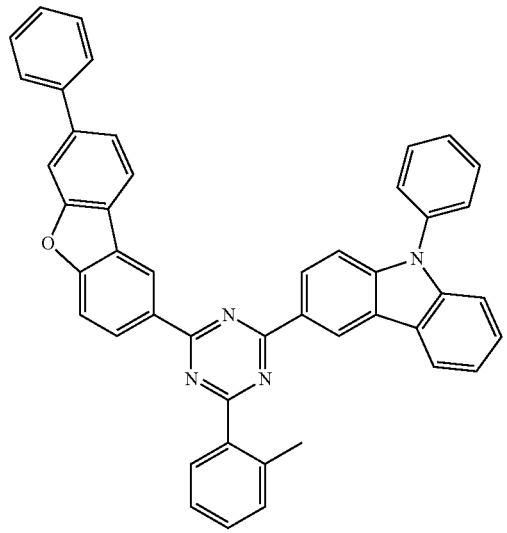
P 3-8
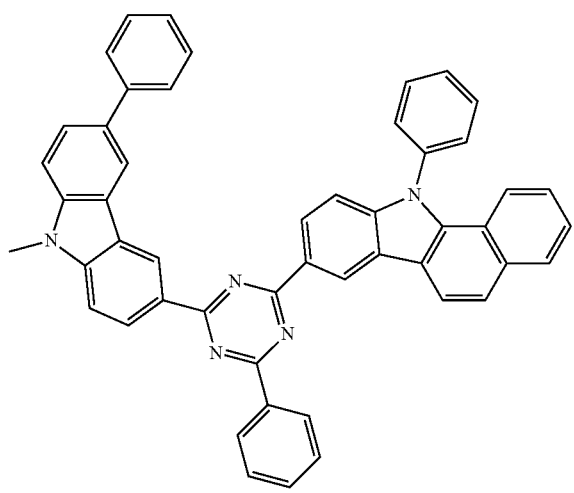
P 3-9
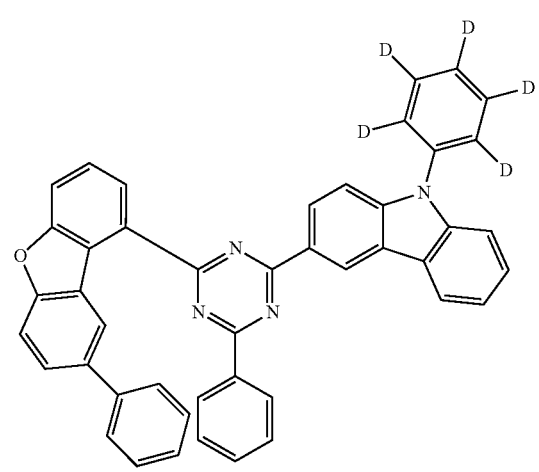
P 3-10
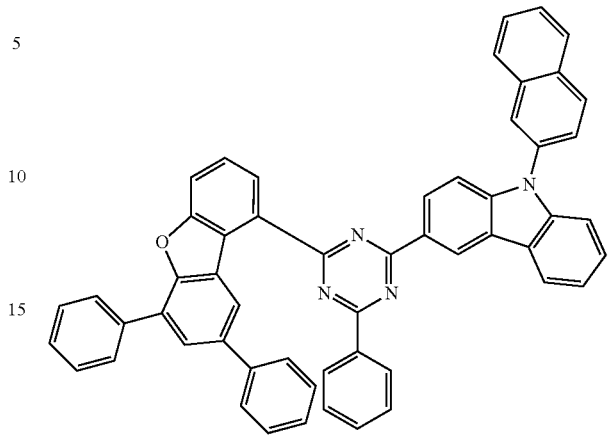
P 3-11
P 3-12
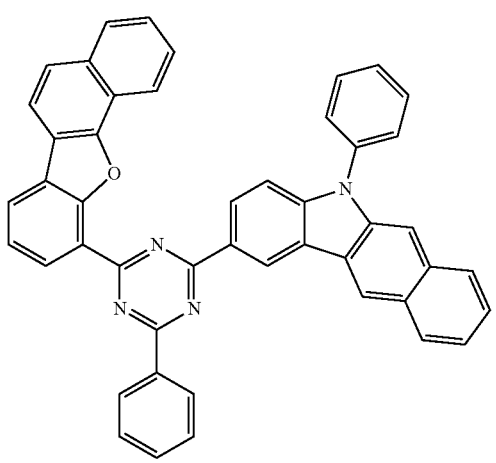

P 4-1
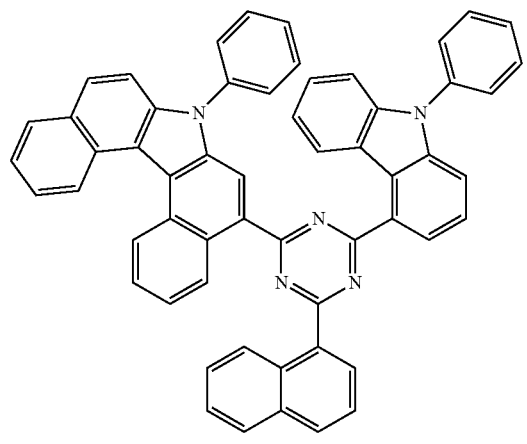
P 4-2
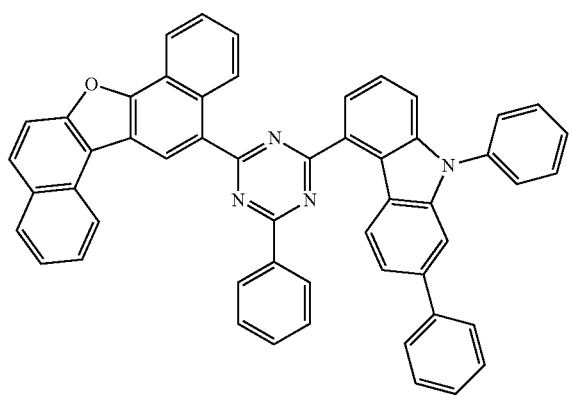
P 4-3
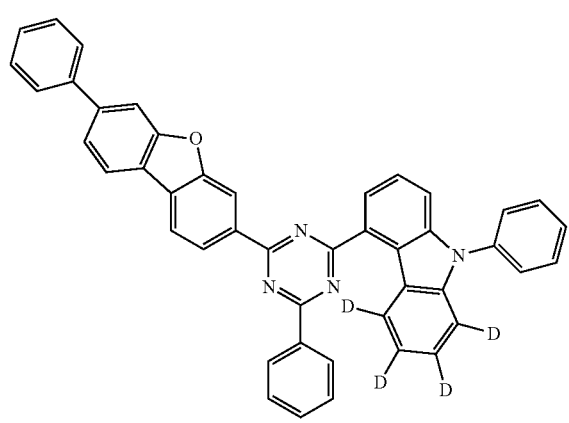
P 4-4
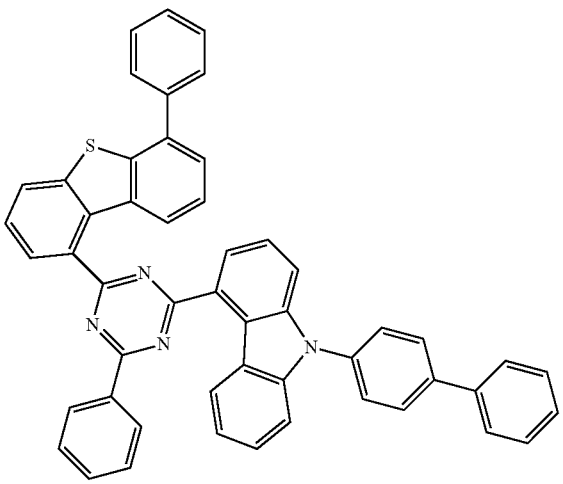
P 4-5
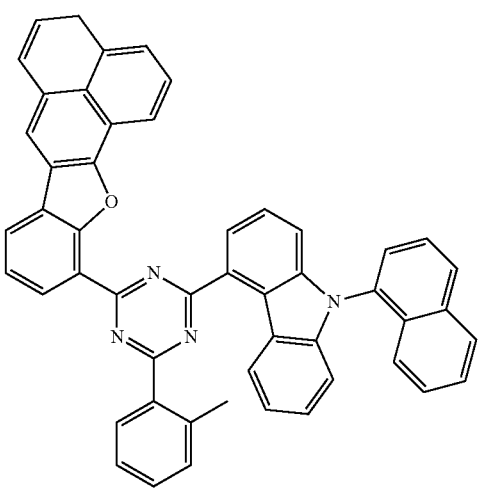
P 4-6
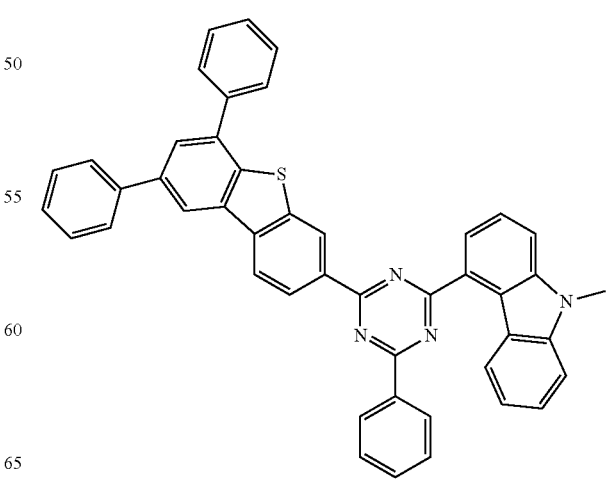

P 4-7
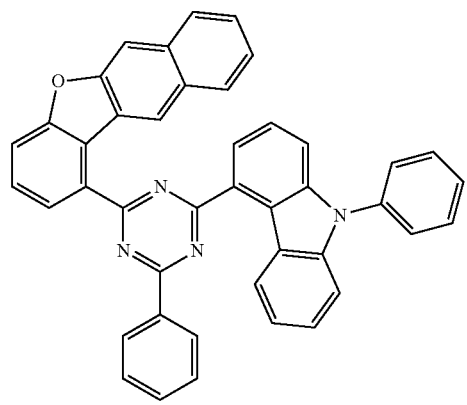
P 4-8
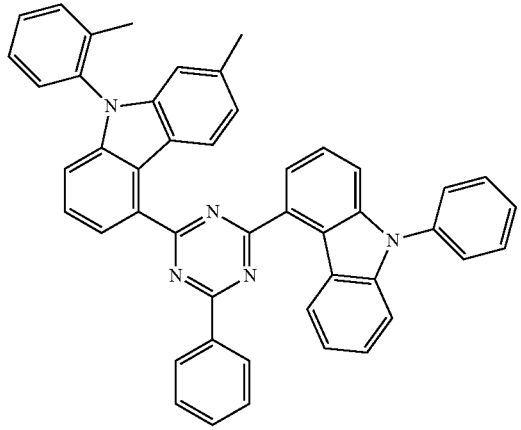
P 4-9
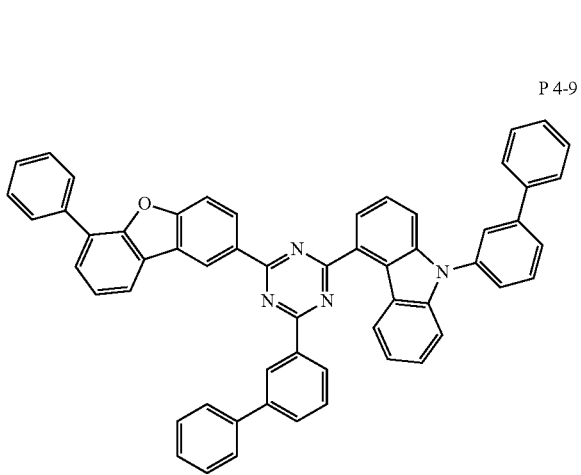
P 4-10
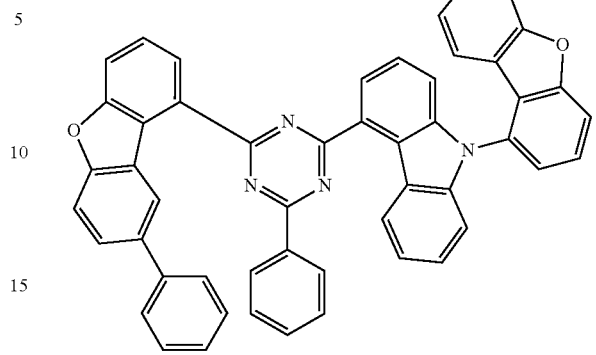
P 4-11
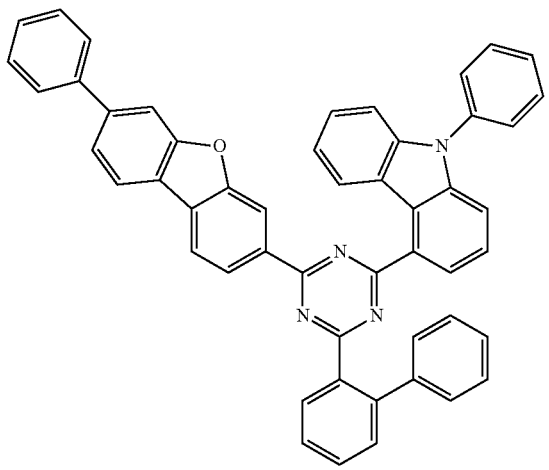
P 4-12
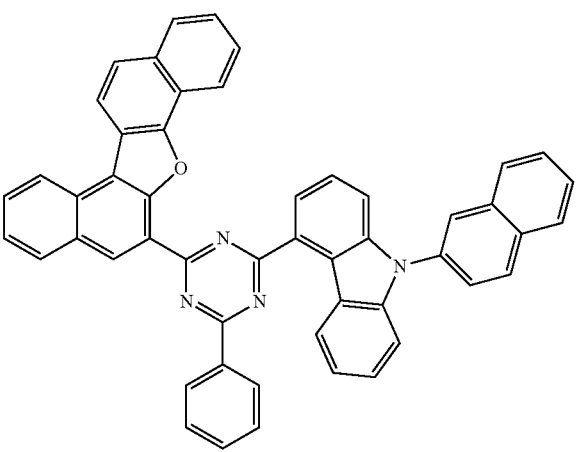

P 4-13
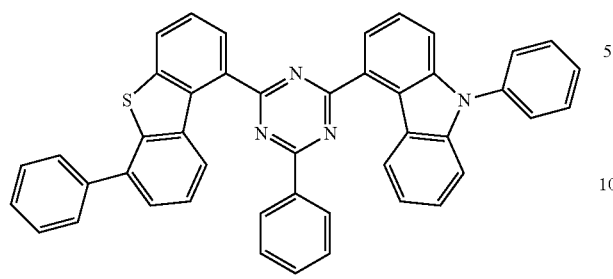

P 4-15
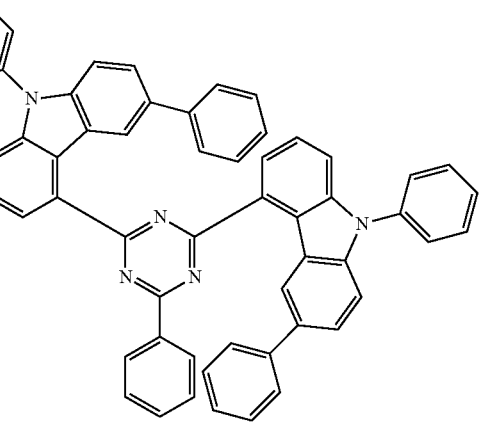

P 4-14
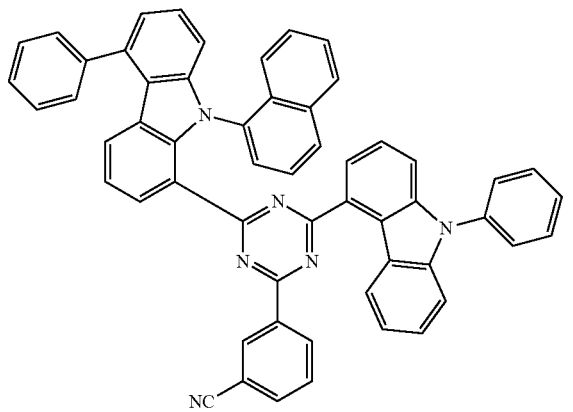

P 4-16
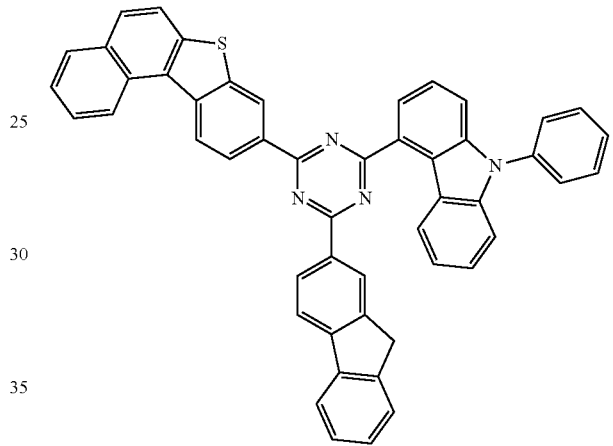

The FD-MS values of the compounds are shown in Table 1 below.

TABLE 1

| Compound | FD-MS | Compound | FD-MS |
|---|---|---|---|
| P 1-1 | m/z = 715.27 ($C_{51}H_{33}N_5$ = 715.86) | P 1-2 | m/z = 656.20 ($C_{45}H_{28}N_4S$ = 656.81) |
| P 1-3 | m/z = 640.23 ($C_{45}H_{28}N_5O$ = 640.75) | P 1-4 | m/z = 656.20 ($C_{45}H_{28}N_4S$ = 656.81) |
| P 1-5 | m/z = 614.21 ($C_{43}H_{26}N_4O$ = 614.71) | P 1-6 | m/z = 630.19 ($C_{43}H_{26}N_4S$ = 630.77) |
| P 1-7 | m/z = 716.26 ($C_{51}H_{32}N_4O$ = 716.84) | P 1-8 | m/z = 680.20 ($C_{47}H_{28}N_4S$ = 680.83) |
| P 1-9 | m/z = 695.27 ($C_{49}H_{25}D_5N_4O$ = 695.84) | P 1-10 | m/z = 630.19 ($C_{43}H_{26}N_4S$ = 630.77) |
| P 1-11 | m/z = 664.23 ($C_{47}H_{28}N_4O$ = 664.77) | P 1-12 | m/z = 806.25 ($C_{57}H_{34}N_4S$ = 806.99) |
| P 1-13 | m/z = 695.27 ($C_{49}H_{25}D_5N_4O$ = 695.84) | P 1-14 | m/z = 681.29 ($C_{48}H_{35}N_5$ = 681.84) |
| P 1-15 | m/z = 728.26 ($C_{52}H_{32}N_4O$ = 728.86) | P 1-16 | m/z = 796.27 ($C_{56}H_{36}N_4S$ = 796.99) |
| P 2-1 | m/z = 689.26 ($C_{49}H_{31}N_5$ = 689.82) | P 2-2 | m/z = 664.23 ($C_{47}H_{28}N_4O$ = 664.77) |
| P 2-3 | m/z = 762.19 ($C_{51}H_{30}N_4S_2$ = 762.95) | P 2-4 | m/z = 792.29 ($C_{57}H_{36}N_4O$ = 792.94) |
| P 2-5 | m/z = 716.26 ($C_{51}H_{32}N_4O$ = 716.84) | P 2-6 | m/z = 806.25 ($C_{57}H_{34}N_4S$ = 806.99) |
| P 2-7 | m/z = 772.27 ($C_{54}H_{36}N_4S$ = 772.97) | P 2-8 | m/z = 732.23 ($C_{51}H_{32}N_4S$ = 732.91) |
| P 2-9 | m/z = 654.24 ($C_{46}H_{30}N_4O$ = 654.77) | P 2-10 | m/z = 644.20 ($C_{44}H_{28}N_4S$ = 644.80) |
| P 2-11 | m/z = 792.29 ($C_{57}H_{36}N_4O$ = 792.94) | P 2-12 | m/z = 732.23 ($C_{51}H_{32}N_4S$ = 732.91) |
| P 2-13 | m/z = 640.23 ($C_{45}H_{28}N_4O$ = 640.75) | P 2-14 | m/z = 770.25 ($C_{54}H_{34}N_4S$ = 770.95) |
| P 2-15 | m/z = 792.29 ($C_{57}H_{36}N_4O$ = 792.94) | P 2-16 | m/z = 744.29 ($C_{53}H_{36}N_4O$ = 744.90) |
| P 3-1 | m/z = 689.26 ($C_{49}H_{31}N_5$ = 689.82) | P 3-2 | m/z = 605.17 ($C_{40}H_{23}N_5S$ = 605.72) |
| P 3-3 | m/z = 790.27 ($C_{57}H_{34}N_4O$ = 790.93) | P 3-4 | m/z = 792.29 ($C_{57}H_{36}N_4O$ = 792.94) |
| P 3-5 | m/z = 680.20 ($C_{47}H_{28}N_4S$ = 680.83) | P 3-6 | m/z = 681.20 ($C_{46}H_{27}N_5S$ = 681.82) |
| P 3-7 | m/z = 654.24 ($C_{46}H_{30}N_4O$ = 654.77) | P 3-8 | m/z = 703.27 ($C_{50}H_{33}N_5$ = 703.85) |
| P 3-9 | m/z = 645.26 ($C_{45}H_{23}D_5N_4O$ = 645.78) | P 3-10 | m/z = 766.27 ($C_{55}H_{34}N_4O$ = 766.90) |
| P 3-11 | m/z = 842.30 ($C_{61}H_{38}N_4O$ = 843.00) | P 3-12 | m/z = 664.23 ($C_{47}H_{28}N_4O$ = 664.77) |
| P 3-13 | m/z = 640.23 ($C_{45}H_{28}N_4O$ = 640.75) | P 3-14 | m/z = 720.30 ($C_{51}H_{28}D_5N_5$ = 720.89) |
| P 3-15 | m/z = 766.27 ($C_{55}H_{34}N_4O$ = 766.90) | P 3-16 | m/z = 756.29 ($C_{54}H_{36}N_4O$ = 756.91) |
| P 4-1 | m/z = 789.29 ($C_{57}H_{35}N_5$ = 789.94) | P 4-2 | m/z = 740.26 ($C_{53}H_{32}N_4O$ = 740.87) |
| P 4-3 | m/z = 644.25 ($C_{45}H_{24}D_5N_4O$ = 644.77) | P 4-4 | m/z = 732.23 ($C_{51}H_{32}N_4O$ = 732.91) |
| P 4-5 | m/z = 716.26 ($C_{51}H_{32}N_4O$ = 716.84) | P 4-6 | m/z = 670.22 ($C_{46}H_{30}N_4S$ = 670.83) |

TABLE 1-continued

| Compound | FD-MS | Compound | FD-MS |
|---|---|---|---|
| P 4-7 | m/z = 614.21 ($C_{43}H_{26}N_4O$ = 614.71) | P 4-8 | m/z = 667.27 ($C_{47}H_{33}N_5$ = 667.82) |
| P 4-9 | m/z = 792.29 ($C_{57}H_{36}N_4O$ = 792.94) | P 4-10 | m/z = 730.24 ($C_{51}H_{30}N_4O_2$ = 730.83) |
| P 4-11 | m/z = 716.26 ($C_{51}H_{32}N_4O$ = 716.84) | P 4-12 | m/z = 714.24 ($C_{51}H_{30}N_4O$ = 714.83) |
| P 4-13 | m/z = 656.20 ($C_{45}H_{28}N_4S$ = 656.81) | P 4-14 | m/z = 790.28 ($C_{56}H_{34}N_6$ = 790.93) |
| P 4-15 | m/z = 791.30 ($C_{57}H_{37}N_5$ = 791.96) | P 4-16 | m/z = 718.22 ($C_{50}H_{30}N_4S$ = 718.88) |

In another aspect of the present invention, the present invention provides an organic electric element comprising a first electrode, a second electrode, and an organic material layer formed between the first electrode and the second electrode, wherein the organic material layer comprises a single compound two or more compounds represented by Formula 1.

The organic material layer comprises at least one of a hole injection layer, a hole transport layer, an emission-auxiliary layer, a light emitting layer, an electron transport-auxiliary layer, an electron transport layer and an electron injection layer, preferably, the compound is comprised in the light emitting layer, more preferably the compound is used as host material of the light emitting layer.

In another aspect of the present invention, the present invention provides an electronic device comprising a display device and a control unit for driving the display device, wherein the display device comprises the organic electric element comprising compound represented by Formula 1.

Hereinafter, synthesis example of the compound represented by Formula 1 and preparation method of an organic electroluminescent element according to the present invention will be described in detail by way of examples. However, the present invention is not limited to the following examples.

SYNTHESIS EXAMPLE

The compound represented by Formula 1 according to the present invention can be synthesized by reacting Core 2 and Sub 2 as shown in Reaction Scheme 1, but there is no limitation thereto.

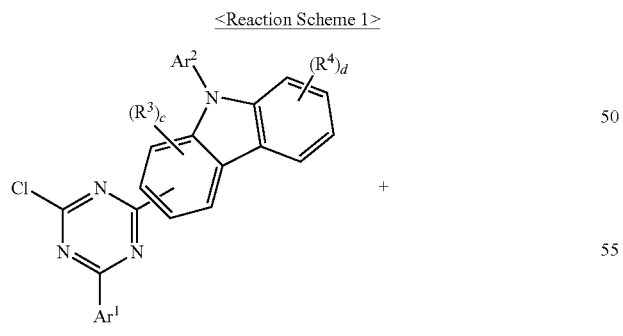

Sub 2

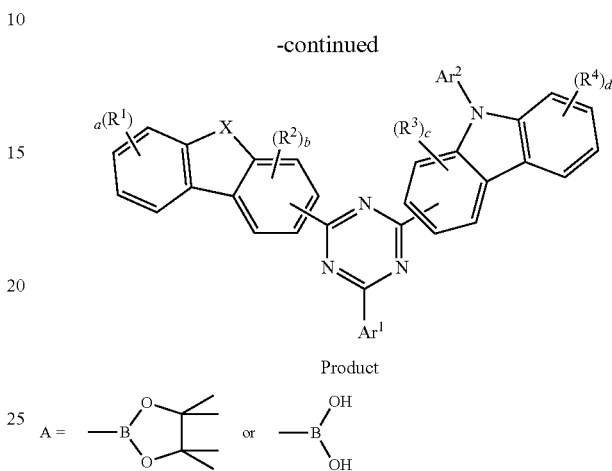

Product

Core 2 of Reaction Scheme 1 may be synthesized by the reaction route of the following Reaction Scheme 2, but are not limited thereto.

<Reaction Scheme 2>

Core 1 of Reaction Scheme 2 may be synthesized by the reaction route of the following Reaction Scheme 3, but are not limited thereto.

<Reaction Scheme 3>
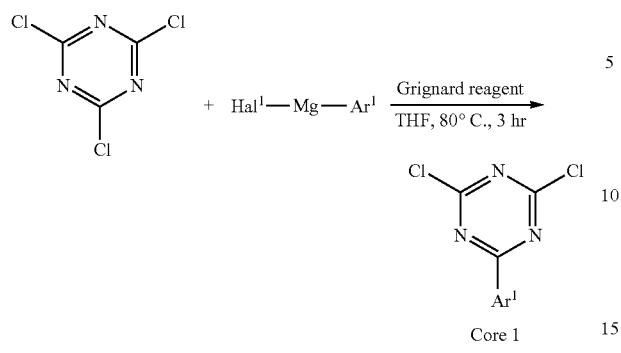
(Hal¹ is I, Br or Cl.)
Exemplary compounds of Core 1, Sub 1, and Core 2 used in Reaction Schemes 1 to 3 are as follows, but are not limited thereto.
Exemplary Compounds of Core 1
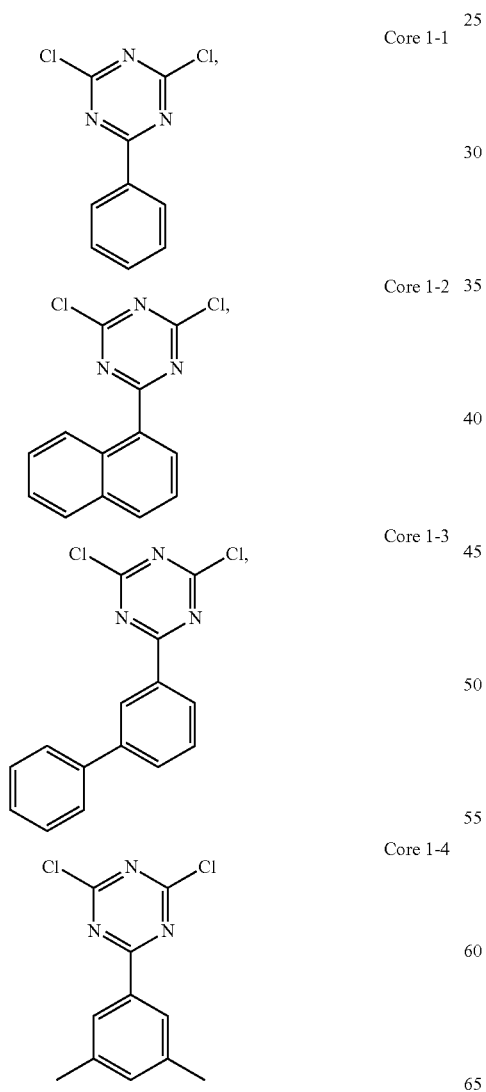
Core 1-1
Core 1-2
Core 1-3
Core 1-4
Exemplary Compounds of Sub 1
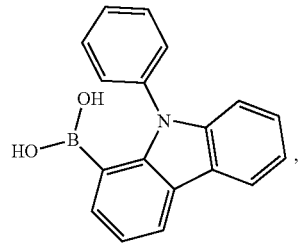
Sub 1-1
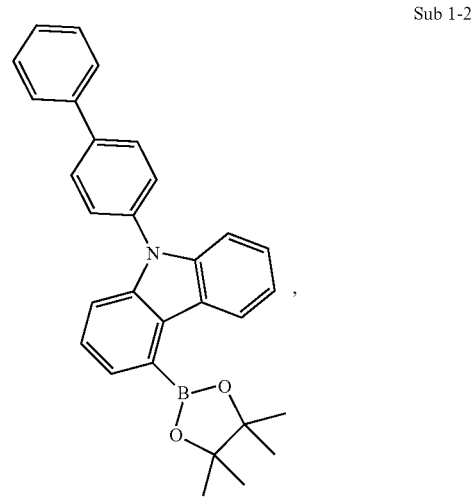
Sub 1-2
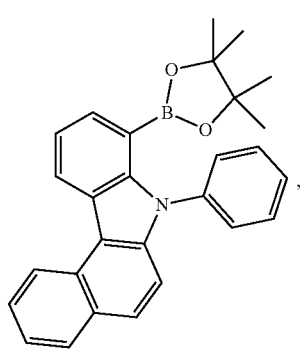
Sub 1-3
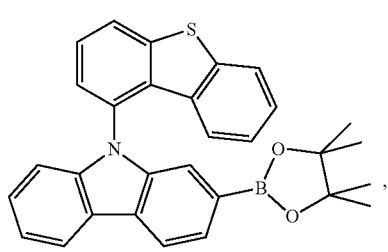
Sub 1-I-4

Sub 1-5
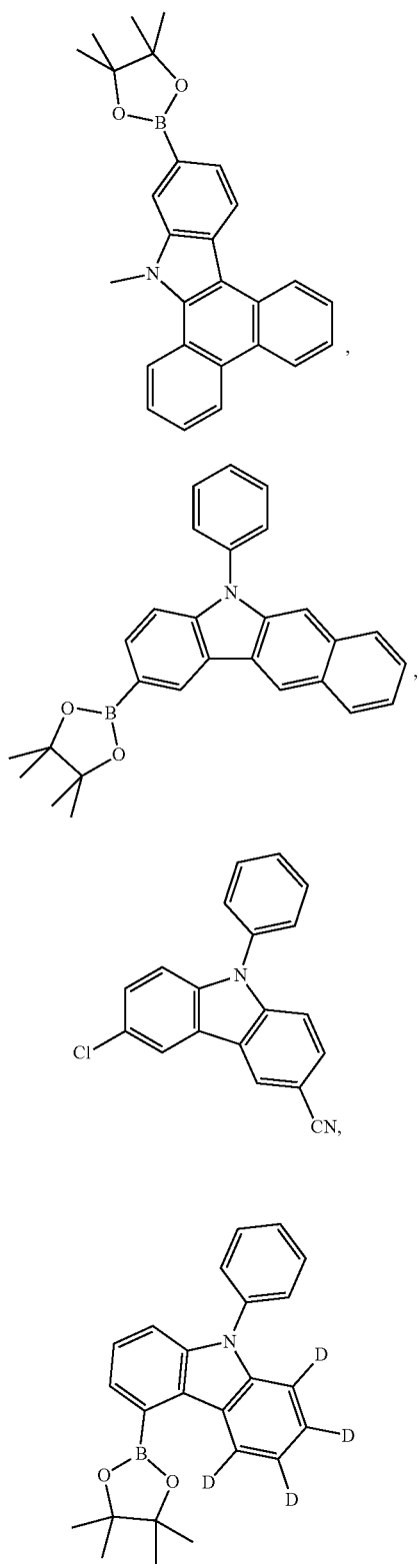
Sub 1-6
Sub 1-I-7
Sub 1-8
Core 2-1
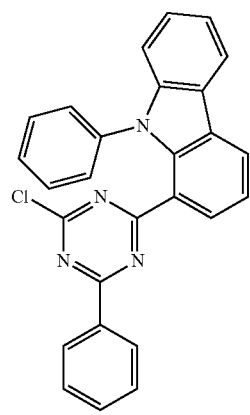
Core 2-2
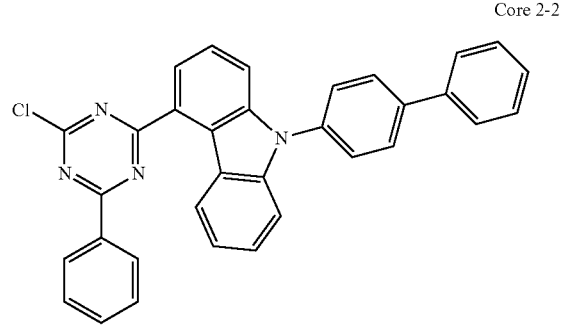
Core 2-3
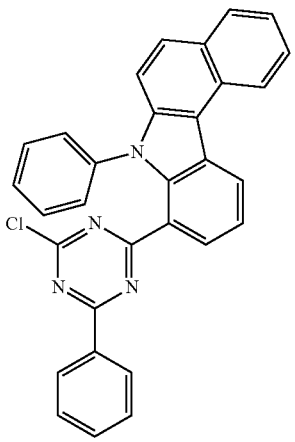
Core 2-4
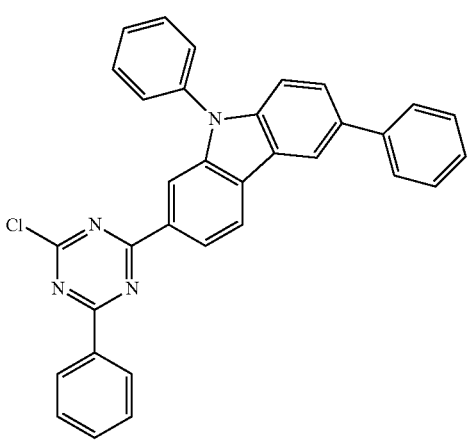
Exemplary Compounds of Core 2
Exemplary compounds of Core 2 are as follows, and FD-MS values of these compounds are shown in Table 2 below.

Core 2-5
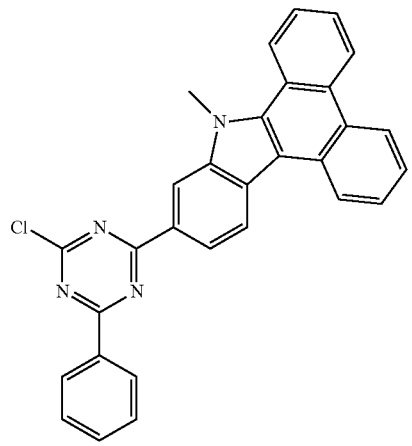
Core 2-6
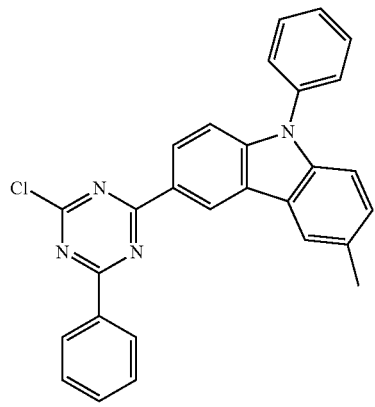
Core 2-7
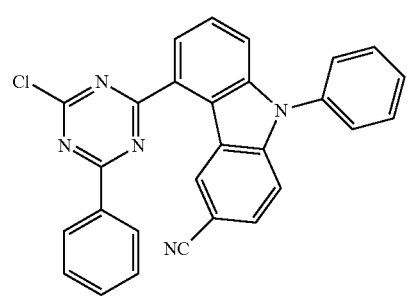
Core 2-8
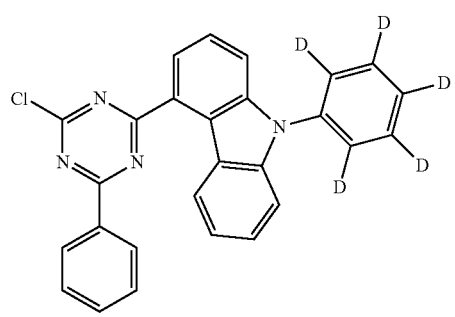
Core 2-9
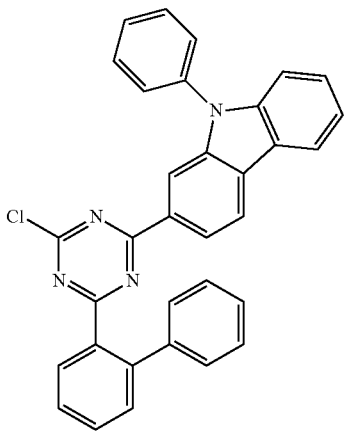
Core 2-10
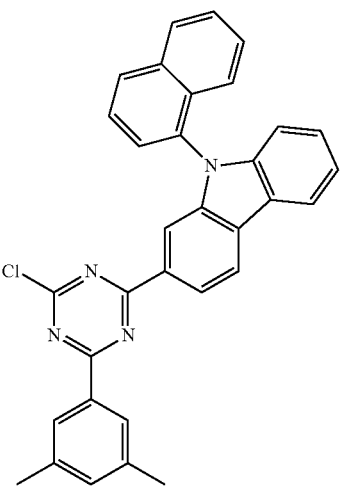
Core 2-11
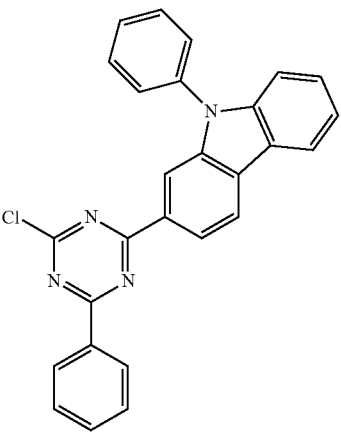

Core 2-12
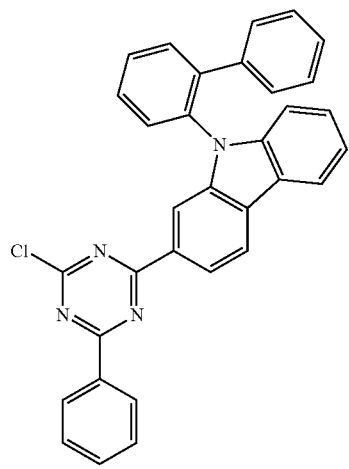
Core 2-13
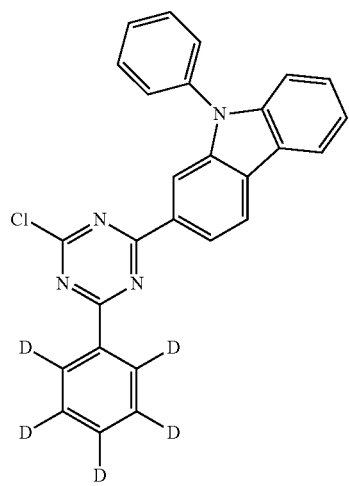
Core 2-14
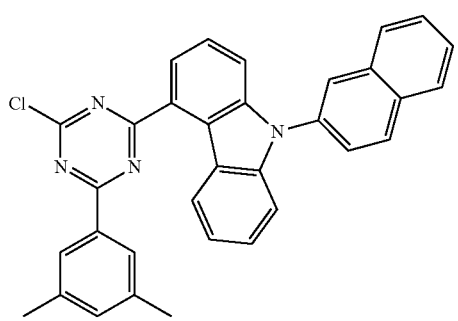
Core 2-15
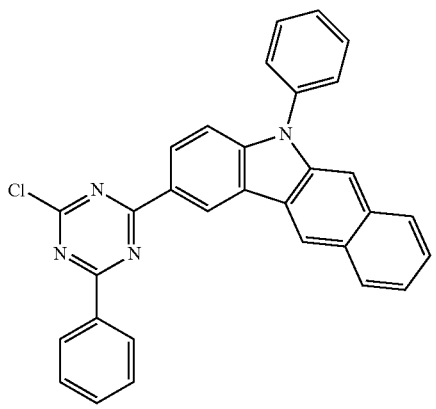
Core 2-16
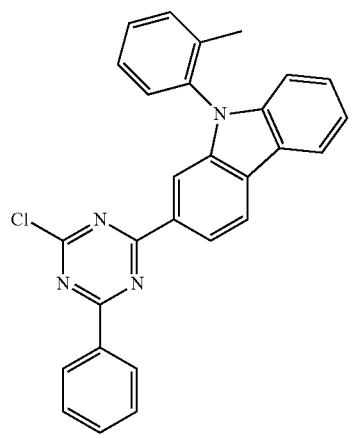
Core 2-17
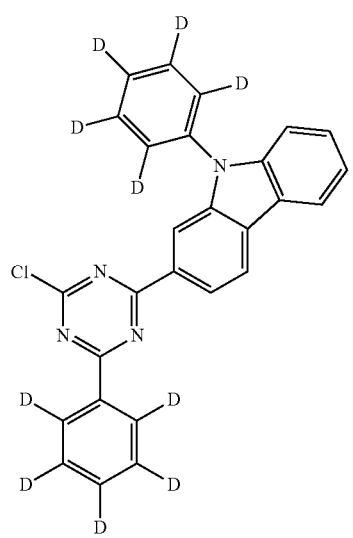

Core 2-18
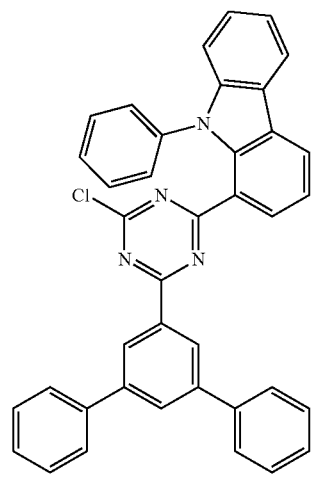
Core 2-19
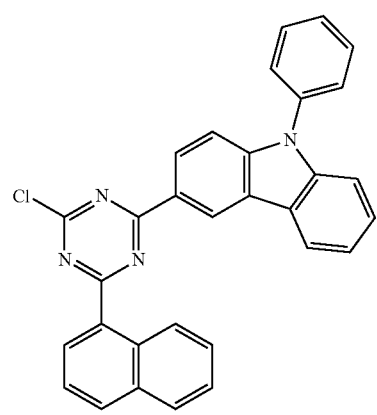
Core 2-20
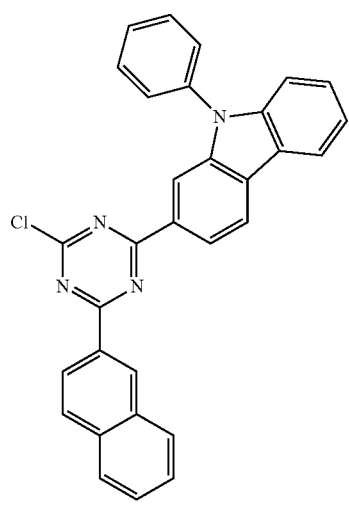
Core 2-21
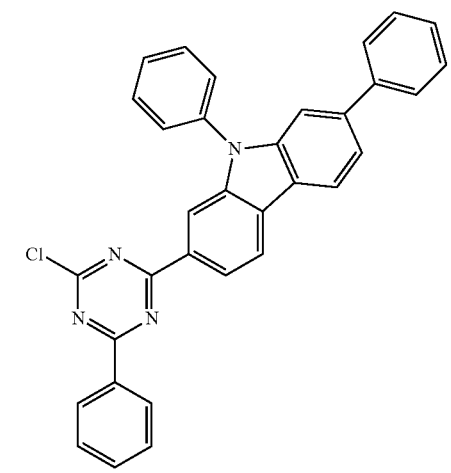
Core 2-22
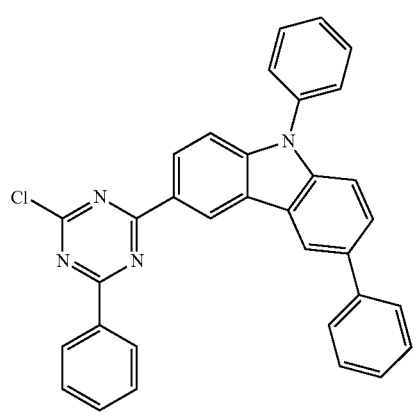
Core 2-23
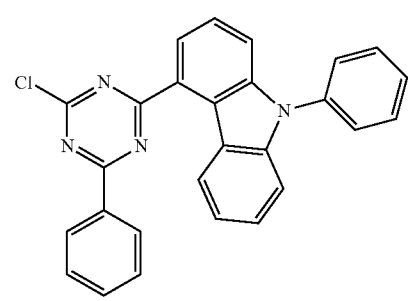
Core 2-24
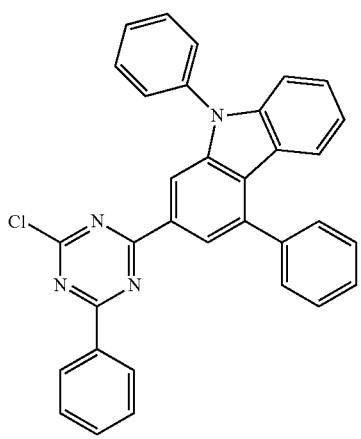

Core 2-25
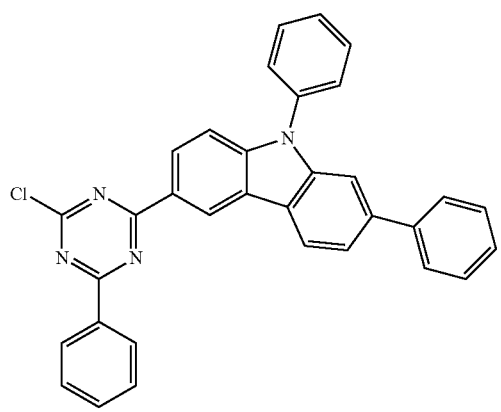
Core 2-26
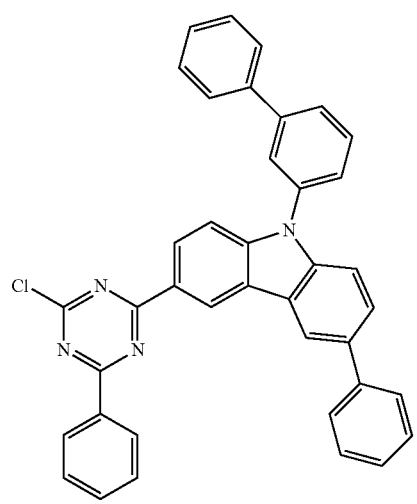
Core 2-27
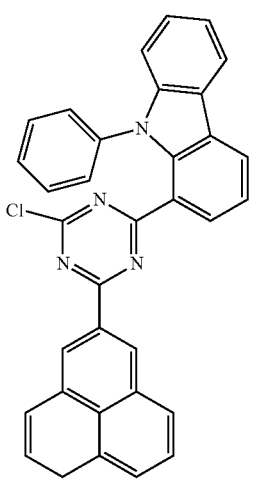
Core 2-28
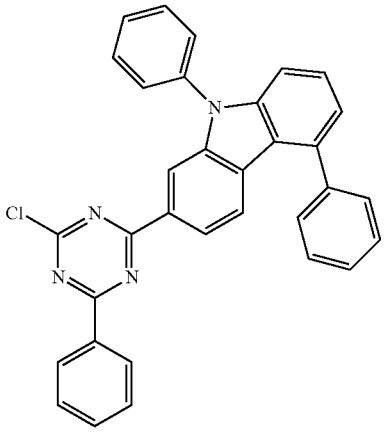
Core 2-29
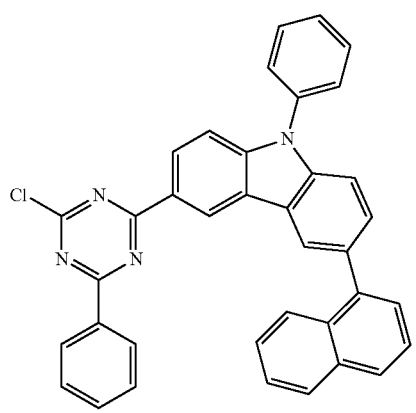
Core 2-30
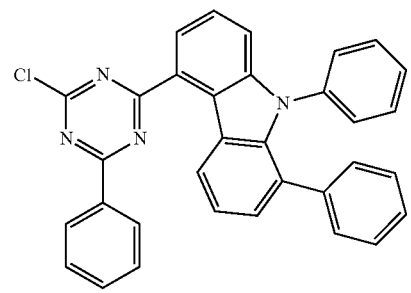
Core 2-31
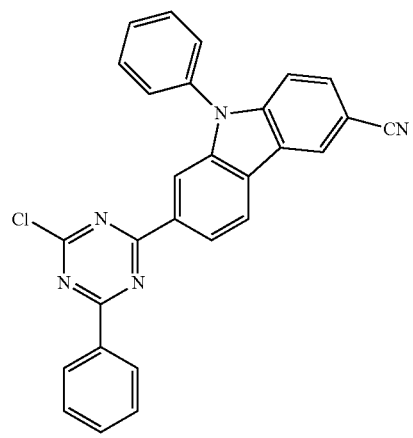

Core 2-32
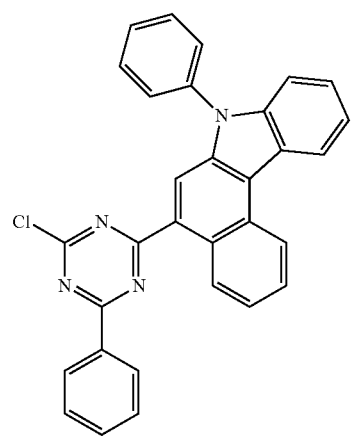
Core 2-33
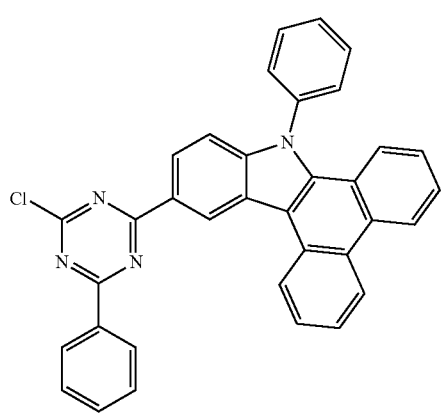
Core 2-34
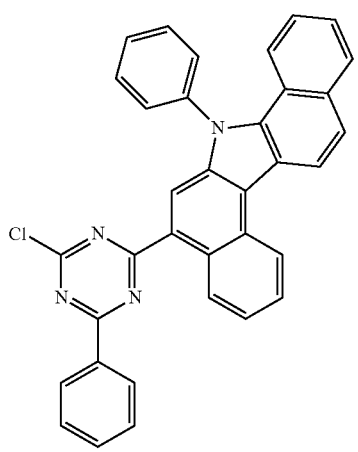
Core 2-35
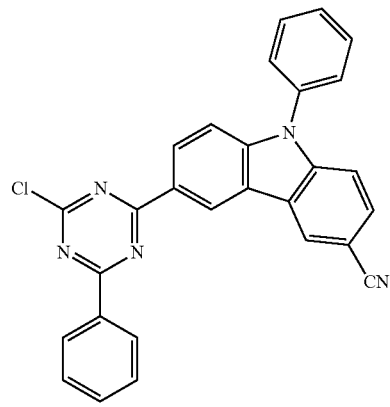
Core 2-36
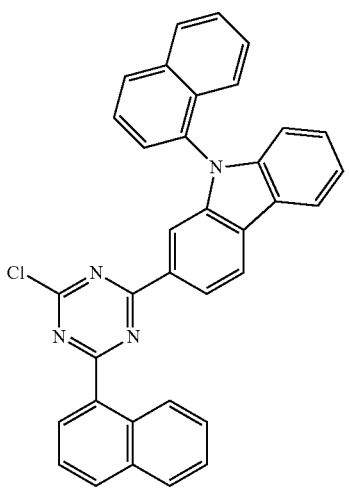
Core 2-37
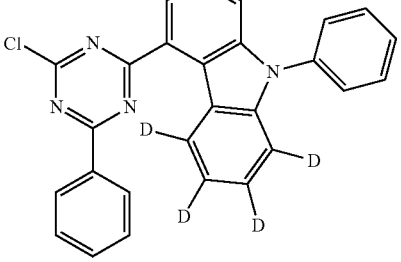
Core 2-38
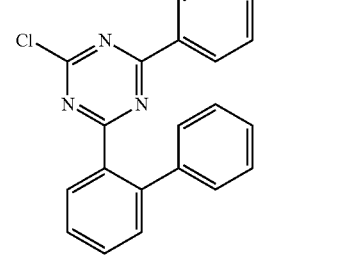

1. Synthesis Example of Core 1

(1) Synthesis of Core 1-1

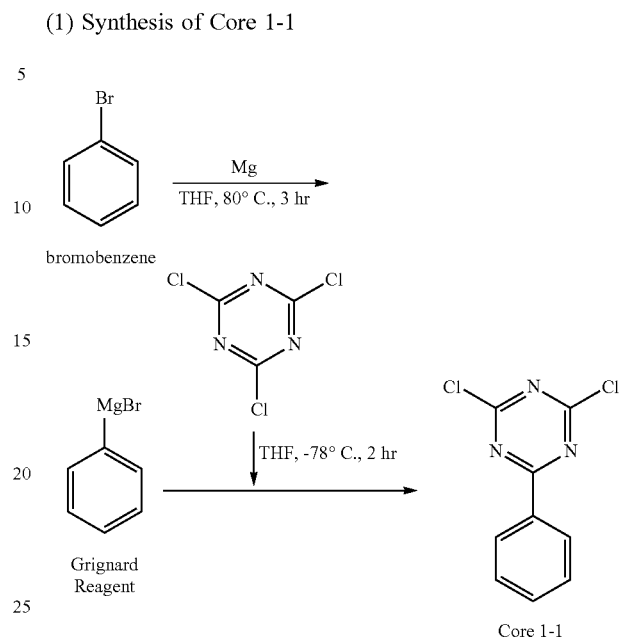

Core 2-39

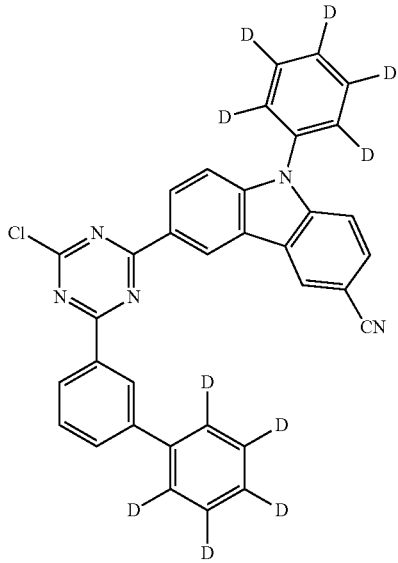

Core 2-40

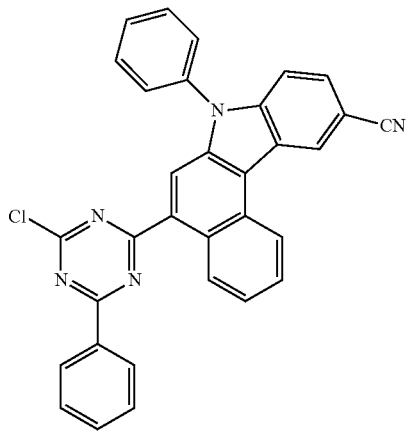

Mg (22.41 g, 921.9 mmol) was placed in a round bottom flask. The dropping funnel and reflux condenser were connected to the round bottom flask to make the inside of the round bottom flask in a vacuum state and the moisture inside the round flask was removed through flame drying. After removing the internal moisture, THF (2,000 mL) was placed in the round bottom flask. Then, the mixture of bromobenzene (144.75 g, 921.9 mmol) and THF (500 mL) was slowly dropped into the round bottom flask. At this time, the temperature of the round bottom flask is set to reflux at 80° C. After about 3 hours, the Grignard reagent was putted through the dropping funnel of a round bottom flask having cyanuric chloride (100.0 g, 542.3 mmol) and THF (2,500 mL). At this time, $N_2$ purging is performed so as not to meet oxygen as much as possible. After that, while slowly dropping the Grignard reagent, the temperature of the round bottom flask is maintained at −78° C., and the reaction

TABLE 2

| Compound | FD-MS | Compound | FD-MS |
|---|---|---|---|
| Core 2-1 | m/z = 432.11 ($C_{27}H_{17}ClN_4$ = 432.91) | Core 2-2 | m/z = 508.15 ($C_{33}H_{21}ClN_4$ = 509.01) |
| Core 2-3 | m/z = 482.13 ($C_{31}H_{19}ClN_4$ = 482.97) | Core 2-4 | m/z = 508.15 ($C_{33}H_{21}ClN_4$ = 509.01) |
| Core 2-5 | m/z = 482.13 ($C_{31}H_{19}ClN_4$ = 482.97) | Core 2-6 | m/z = 446.13 ($C_{28}H_{19}ClN_4$ = 446.94) |
| Core 2-7 | m/z = 457.11 ($C_{28}H_{16}ClN_5$ = 457.92) | Core 2-8 | m/z = 437.15 ($C_{27}H_{12}D_5ClN_4$ = 437.94) |
| Core 2-9 | m/z = 508.15 ($C_{33}H_{21}ClN_4$ = 509.01) | Core 2-10 | m/z = 510.16 ($C_{33}H_{23}ClN_4$ = 511.03) |
| Core 2-11 | m/z = 432.11 ($C_{27}H_{17}ClN_4$ = 432.91) | Core 2-12 | m/z = 508.15 ($C_{33}H_{21}ClN_4$ = 509.01) |
| Core 2-13 | m/z = 437.15 ($C_{27}H_{12}D_5ClN_4$ = 437.94) | Core 2-14 | m/z = 510.16 ($C_{33}H_{23}ClN_4$ = 511.03) |
| Core 2-15 | m/z = 482.13 ($C_{31}H_{19}ClN_4$ = 482.97) | Core 2-16 | m/z = 446.13 ($C_{28}H_{19}ClN_4$ = 446.94) |
| Core 2-17 | m/z = 442.18 ($C_{27}H_7D_{10}ClN_4$ = 442.97) | Core 2-18 | m/z = 584.18 ($C_{39}H_{25}ClN_4$ = 585.11) |
| Core 2-19 | m/z = 482.13 ($C_{31}H_{19}ClN_4$ = 482.97) | Core 2-20 | m/z = 482.13 ($C_{31}H_{19}ClN_4$ = 482.97) |
| Core 2-21 | m/z = 508.15 ($C_{33}H_{21}ClN_4$ = 509.01) | Core 2-22 | m/z = 482.13 ($C_{31}H_{19}ClN_4$ = 482.97) |
| Core 2-23 | m/z = 432.11 ($C_{27}H_{17}ClN_4$ = 432.91) | Core 2-24 | m/z = 508.15 ($C_{33}H_{21}ClN_4$ = 509.01) |
| Core 2-25 | m/z = 508.15 ($C_{33}H_{21}ClN_4$ = 509.01) | Core 2-26 | m/z = 584.18 ($C_{39}H_{25}ClN_4$ = 585.11) |
| Core 2-27 | m/z = 520.15 ($C_{34}H_{21}ClN_4$ = 521.02) | Core 2-28 | m/z = 508.15 ($C_{33}H_{21}ClN_4$ = 509.01) |
| Core 2-29 | m/z = 558.16 ($C_{37}H_{23}ClN_4$ = 559.07) | Core 2-30 | m/z = 508.15 ($C_{33}H_{21}ClN_4$ = 509.01) |
| Core 2-31 | m/z = 457.11 ($C_{28}H_{16}ClN_5$ = 457.92) | Core 2-32 | m/z = 482.13 ($C_{31}H_{18}ClN_4$ = 482.97) |
| Core 2-33 | m/z = 532.15 ($C_{35}H_{21}ClN_5$ = 533.03) | Core 2-34 | m/z = 532.15 ($C_{35}H_{21}ClN_4$ = 533.03) |
| Core 2-35 | m/z = 462.14 ($C_{28}H_{11}D_5ClN_5$ = 462.95) | Core 2-36 | m/z = 532.15 ($C_{35}H_{21}ClN_4$ = 533.03) |
| Core 2-37 | m/z = 432.10 ($C_{27}H_{15}ClN_5$ = 430.90) | Core 2-38 | m/z = 584.18 ($C_{39}H_{25}ClN_4$ = 585.11) |
| Core 2-39 | m/z = 543.20 ($C_{34}H_{10}D_{10}ClN_5$ = 544.O8) | Core 2-40 | m/z = 507.13 ($C_{32}H_{18}ClN_5$ = 507.98) | proceeds for two hours. When the reaction was completed, the reaction product was quenched by adding water and then water in the reaction product was removed. Then, the reaction product was filtered under reduced pressure. An organic layer was dried over MgSO$_4$ and concentrated. Then, a silica gel column and recrystallization were applied to the concentrate to obtain 94.40 g (yield: 77%) of the product.

(2) Synthesis of Core 1-2

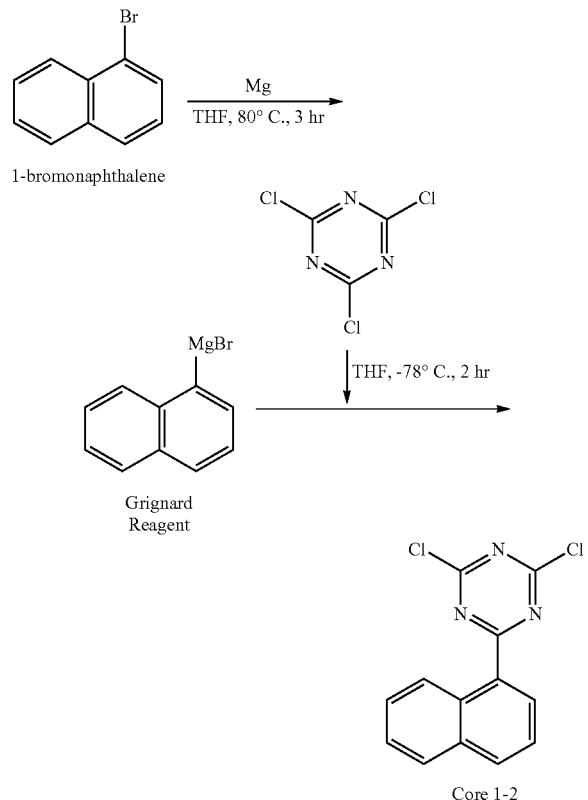

Core 1-2

(3) Synthesis of Core 1-3

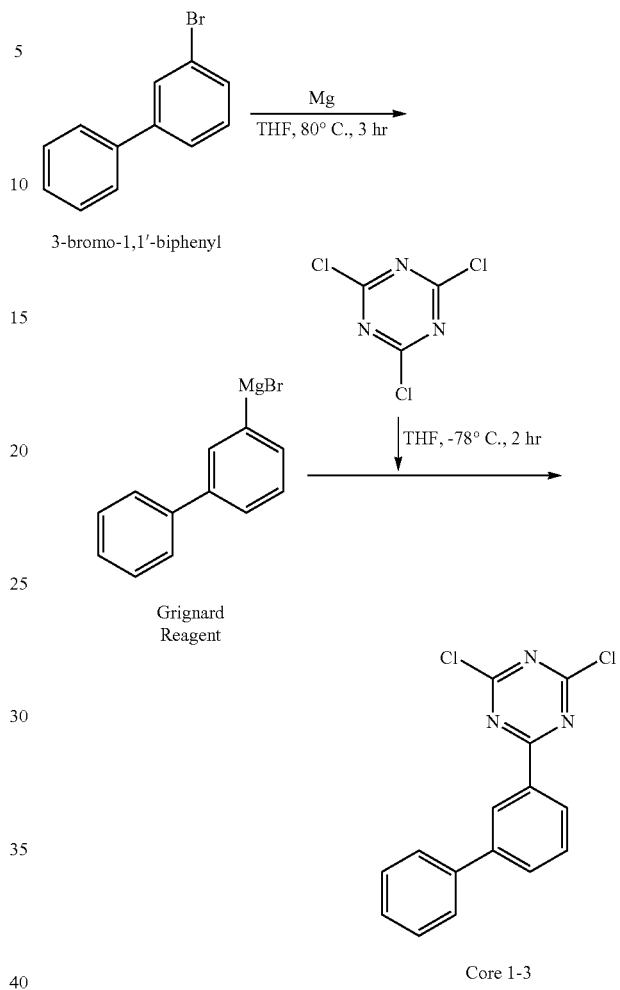

Core 1-3

Mg (24.65 g, 1106.3 mmol) was placed in a round bottom flask. The dropping funnel and reflux condenser were connected to the round bottom flask to make the inside of the round bottom flask in a vacuum state and the moisture inside the round flask was removed through flame drying. After removing the internal moisture, THF (2,000 mL) was placed in the round bottom flask. Then, the mixture of 1-bromonaphthalene (190.90 g, 921.9 mmol) and THF (500 mL) was slowly dropped into the round bottom flask. At this time, the temperature of the round bottom flask is set to reflux at 80° C. After about 3 hours, the Grignard reagent was putted through the dropping funnel of a round bottom flask having cyanuric chloride (110.0 g, 596.5 mmol) and THF (2,500 mL). At this time, N$_2$ purging is performed so as not to meet oxygen as much as possible. After that, while slowly dropping the Grignard reagent, the temperature of the round bottom flask is maintained at −78° C., and the reaction proceeds for two hours. When the reaction was completed, the reaction product was quenched by adding water and then water in the reaction product was removed. Then, the reaction product was filtered under reduced pressure. An organic layer was dried over MgSO$_4$ and concentrated. Then, a silica gel column and recrystallization were applied to the concentrate to obtain 118.59 g (yield: 70%) of the product.

Mg (25.77 g, 1060.2 mmol) was placed in a round bottom flask. The dropping funnel and reflux condenser were connected to the round bottom flask to make the inside of the round bottom flask in a vacuum state and the moisture inside the round flask was removed through flame drying. After removing the internal moisture, THF (2,000 mL) was placed in the round bottom flask. Then, the mixture of 3-bromo-1,1'-biphenyl (214.91 g, 921.9 mmol) and THF (500 mL) was slowly dropped into the round bottom flask. At this time, the temperature of the round bottom flask is set to reflux at 80° C. After about 3 hours, the Grignard reagent was putted through the dropping funnel of a round bottom flask having cyanuric chloride (115.0 g, 623.6 mmol) and THF (2,500 mL).

At this time, N$_2$ purging is performed so as not to meet oxygen as much as possible. After that, while slowly dropping the Grignard reagent, the temperature of the round bottom flask is maintained at −78° C., and the reaction proceeds for two hours. When the reaction was completed, the reaction product was quenched by adding water and then water in the reaction product was removed. Then, the reaction product was filtered under reduced pressure. An organic layer was dried over MgSO$_4$ and concentrated. Then, a silica gel column and recrystallization were applied to the concentrate to obtain 141.33 g (yield: 75%) of the product.

(4) Synthesis of Core 1-4

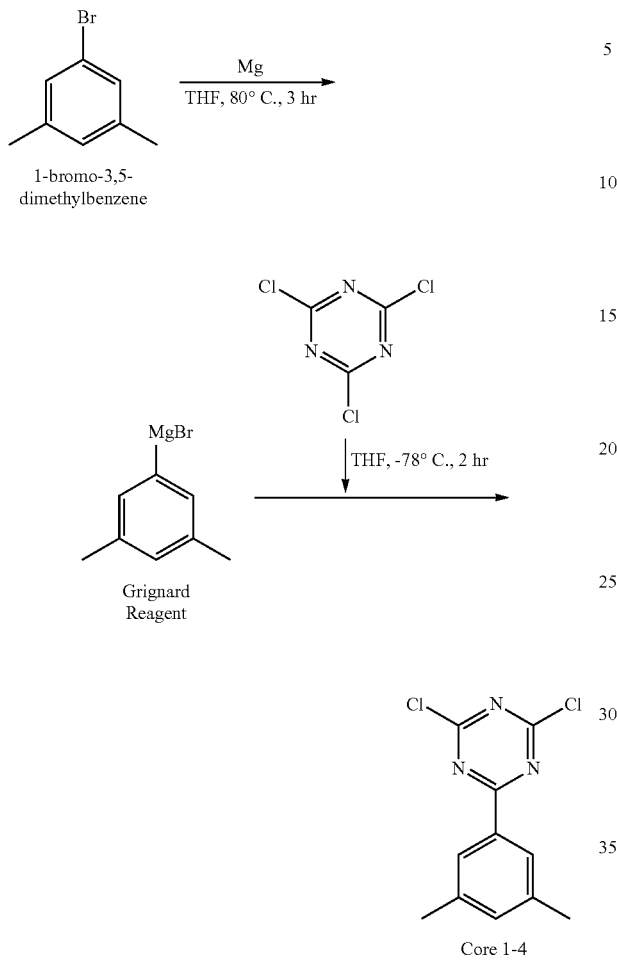

2. Synthesis Example of Core 2

(1) Synthesis of Core 2-1

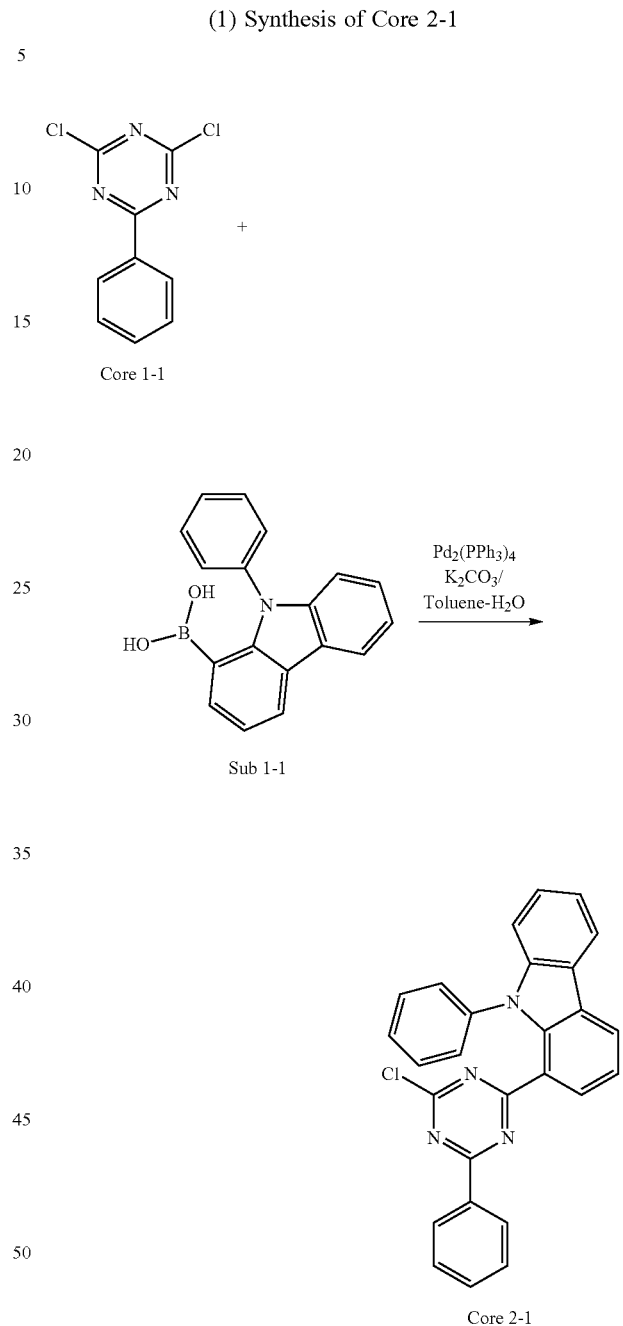

Mg (24.65 g, 1014.1 mmol) was placed in a round bottom flask. The dropping funnel and reflux condenser were connected to the round bottom flask to make the inside of the round bottom flask in a vacuum state and the moisture inside the round flask was removed through flame drying. After removing the internal moisture, THF (2,000 mL) was placed in the round bottom flask. Then, the mixture of 1-bromo-3,5-dimethylbenzene (170.61 g, 921.9 mmol) and THF (500 mL) was slowly dropped into the round bottom flask. At this time, the temperature of the round bottom flask is set to reflux at 80° C. After about 3 hours, the Grignard reagent was putted through the dropping funnel of a round bottom flask having cyanuric chloride (110.0 g, 596.5 mmol) and THF (2,500 mL). At this time, $N_2$ purging is performed so as not to meet oxygen as much as possible. After that, while slowly dropping the Grignard reagent, the temperature of the round bottom flask is maintained at −78° C., and the reaction proceeds for two hours. When the reaction was completed, the reaction product was quenched by adding water and then water in the reaction product was removed. Then, the reaction product was filtered under reduced pressure. An organic layer was dried over $MgSO_4$ and concentrated. Then, a silica gel column and recrystallization were applied to the concentrate to obtain 118.24 g (yield: 78%) of the product.

Core 1-1 (15.0 g, 66.4 mmol), Sub 1-1 (19.05 g, 66.4 mmol), $Pd_2(PPh_{-3})_4$ (2.30 g, 2.0 mmol) and $K_2CO_3$ (27.51 ml, 199.1 mmol) were placed in a round bottom flask and the mixture was dissolved in toluene (200 mL) and $H_2O$ (100 mL). Then, the solution was stirred at 120° C. and the reaction was overnight. When the reaction was completed, water was removed from the reaction product and the reaction product was filtered under reduced pressure. After that, an organic layer was dried over $MgSO_4$ and concentrated. Then, a silica gel column and recrystallization were applied to the concentrate to obtain 18.96 g (yield: 66%) of the product.

(2) Synthesis of Core 2-2

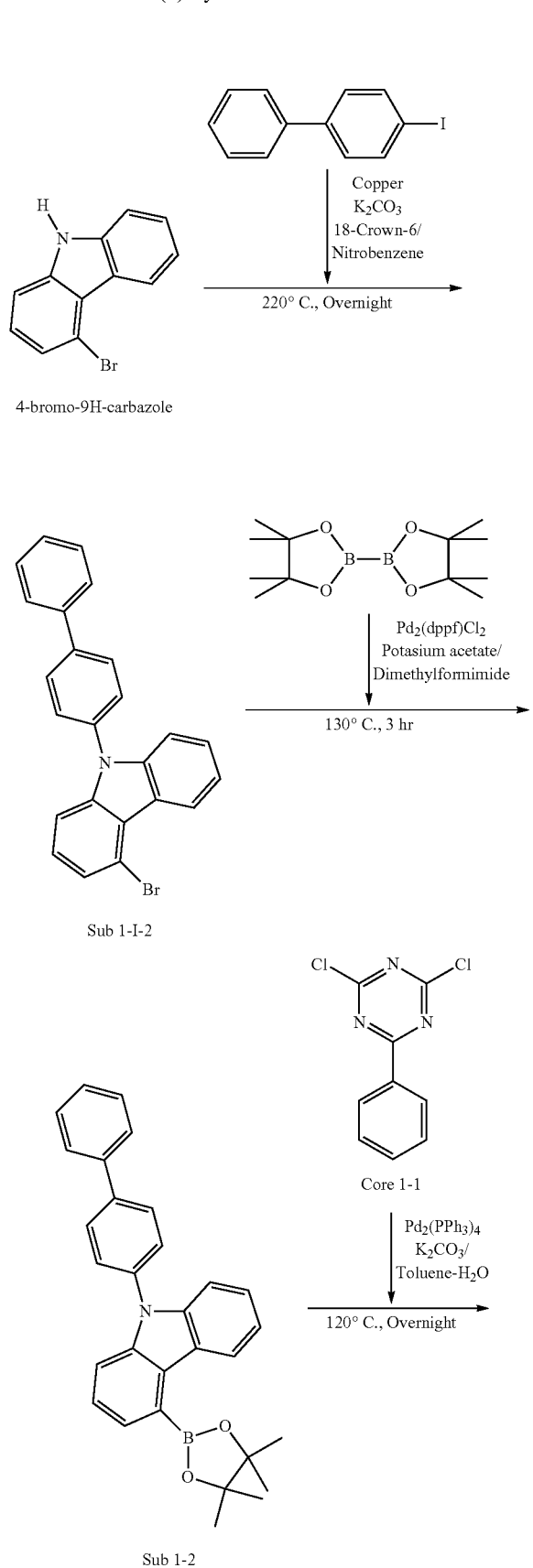

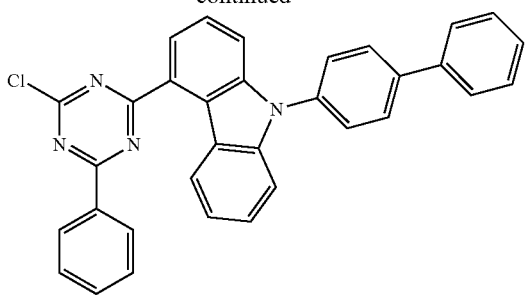

Core 2-2

(2-1) Synthesis of Sub 1-I-2

4-bromo-9H-carbazole (55.0 g, 223.5 mmol), iodobiphenyl (75.12 g, 268.2 mmol), Copper (1.42 g, 22.3 mmol), 18-Crown-6 (4.03 g, 11.2 mmol) and $K_2CO_3$ (92.66 g, 670.4 mmol) were placed in a round bottom flask and nitrobenzene (1,000 mL) was added thereto. After the mixture was heated to 220° C. and dissolved, the solution was stirred overnight. When the reaction was complete, the reaction product was concentrated under reduced pressure and quenched with water. Thereafter, the product is filtered to obtain a solid and the filtrate is collected. After water is removed from the filtrate, the filtrate was filtered under reduced pressure, dried over $MgSO_4$, and concentrated. Then, a silica gel column and recrystallization were applied to the concentrate to obtain 68.54 g (yield: 77%) of the product.

(2-2) Synthesis of Sub 1-2

Sub 1-I-2 (68.54 g, 172.1 mmol), bis(pinacolato)diboron (65.55 g, 258.1 mmol), $PdCl_2$(dppf) (4.22 g, 5.2 mmol) and potassium acetate (50.66 g, 516.2 mmol) were placed in a round bottom flask and toluene (860 mL) was added thereto. The mixture was stirred at 130° C. for 3 hours. When the reaction was complete, the reaction product was quenched by adding water and water was removed. After the reaction product was filtered under reduced pressure, an organic layer was dried over $MgSO_4$ and concentrated to obtain 50.63 g (yield: 81%) of the product.

(2-3) Synthesis of Core 2-2

Sub 1-2 (15.0 g, 41.3 mmol), Core 1-2 (12.14 g, 53.7 mmol), $Pd(PPh_3)_4$ (1.43 g, 1.2 mmol) and potassium carbonate (17.12 g, 123.9 mmol) were placed in a round bottom flask and toluene (200 mL) and $H_2O$ (50 mL) were added thereto. The mixture was heated to 120° C. and stirred overnight. When the reaction was complete, water was removed from the reaction product and an organic layer was concentrated. Then, a silica gel column and recrystallization were applied to the concentrate to obtain 15.98 g (yield: 76%) of the product.

(3) Synthesis of Core 2-3

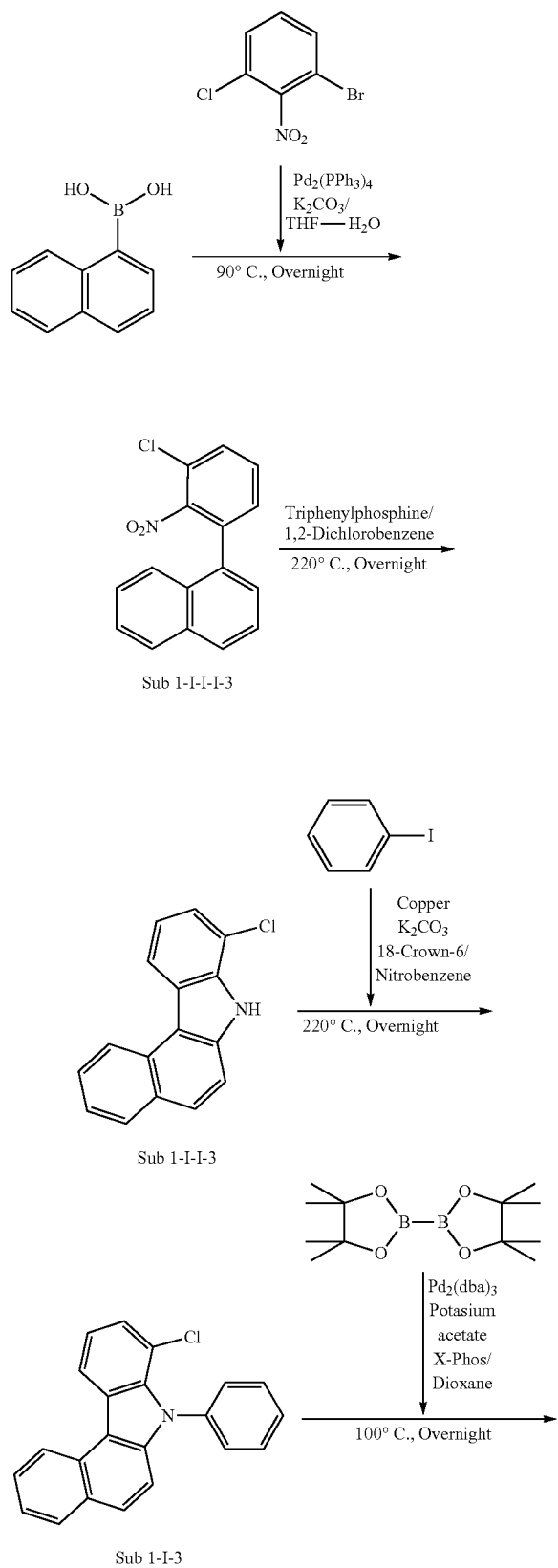

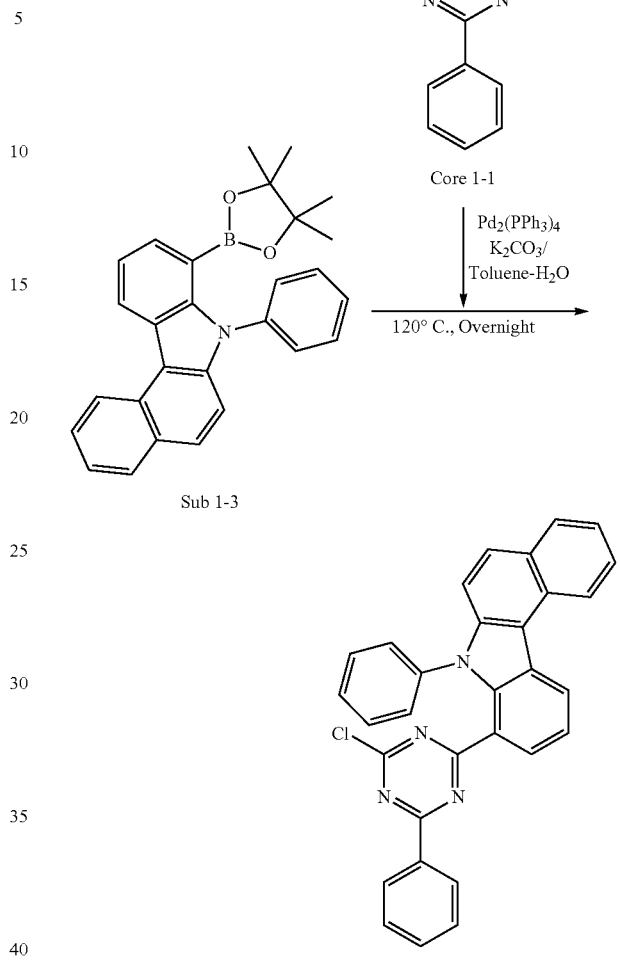

(3-1) Synthesis of Sub 1-I-I-I-3

Naphthalene-1-ylboronic acid (120.02 g, 697.8 mmol), Pd$_2$(PPh$_3$)$_4$ (21.99 g, 19.0 mmol) and K$_2$CO$_3$ (263.03 g, 1903.2 mmol) were added to 1-bromo-3-chloro-2-nitrobenzene (150.0 g, 634.4 mmol) and THF (220 mL) and H$_2$O (110 mL) were added thereto. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 111.59 g (yield: 62%) of the product.

(3-2) Synthesis of Sub 1-I-I-3

Sub 1-I-I-I-3 (111.59 g, 393.3 mmol), triphenylphosphine (309.49 g, 1180.0 mmol) and 1,2-dichlorobenzene (1,300 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO₄, and concentrated. Then, a silica gel column and recrystallization were applied to the concentrate to obtain 69.30 g (yield: 70%) of the product.

(3-3) Synthesis of Sub 1-I-3

Sub 1-I-I-3 (69.30 g, 275.3 mmol), iodobenzene (280.84 g, 1376.6 mmol), Copper (1.75 g, 27.5 mmol), 18-Crown-6 (4.96 g, 13.8 mmol), K₂CO₃ (114.15 g, 826.0 mmol) and nitrobenzene (1,000 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO₄, and concentrated. Then, a silica gel column and recrystallization were applied to the concentrate to obtain 78.52 g (yield: 87%) of the product.

(3-4) Synthesis of Sub 1-3

Sub 1-I-3 (78.52 g, 239.5 mmol), bis(pinacolato)diboron (91.24 g, 359.03 mmol), Pd₂(dba)₃ (10.97 g, 12.0 mmol), potassium acetate (70.52 g, 718.6 mmol), X-phos (11.42 g, 24.0 mmol) and dioxane (800 mL) were placed in a round bottom flask and the mixture was stirred at 100° C. overnight. When the reaction was completed, the reaction product was quenched by adding water and water was removed. Thereafter, the reaction product was filtered under reduced pressure and an organic layer was dried over MgSO₄ and concentrated to obtain 70.31 g (yield: 70%) of the product.

(3-5) Synthesis of Core 2-3

Sub 1-3 (70.31 g, 167.7 mmol), Core 1-1 (49.28 g, 218.0 mmol), Pd₂(PPh₃)₄ (5.81 g, 5.0 mmol), K₂CO₃ (69.52 g, 503.0 mmol), toluene (220 mL) and H₂O (110 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO₄, and concentrated. Then, a silica gel column and recrystallization were applied to the concentrate to obtain 49.40 g (yield: 61%) of the product.

(4) Synthesis of Core 2-4

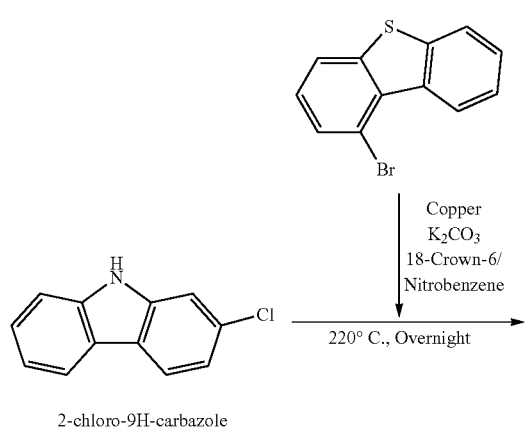

2-chloro-9H-carbazole

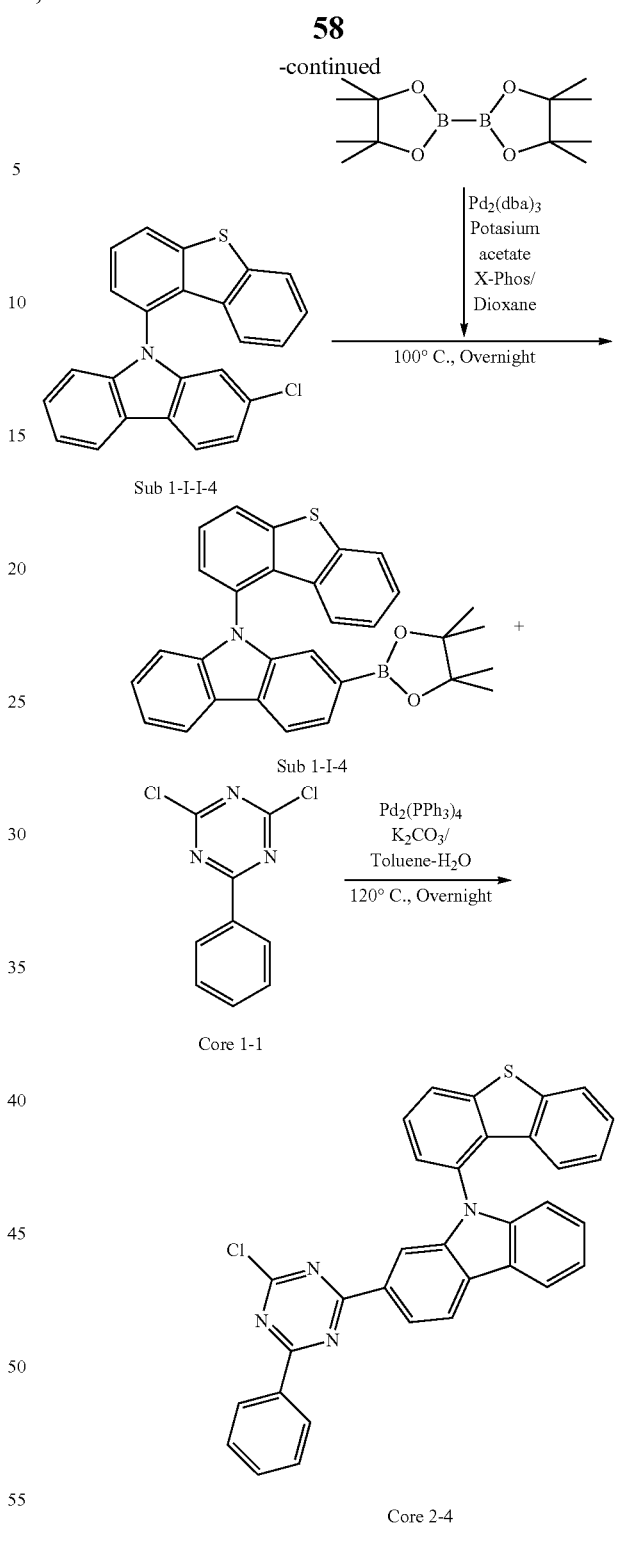

Sub 1-I-I-4

Sub 1-I-4

Core 1-1

Core 2-4

(4-1) Synthesis of Sub 1-I-I-4

2-chloro-9H-carbazole (100 g, 495.9 mmol), 1-bromodibenzo[b,d]thiophene (391.50 g, 1487.7 mmol), Copper (3.15 g, 49.6 mmol), 18-Crown-6 (8.94 g, 24.8 mmol), K₂CO₃ (205.62 g, 1,487.7 mmol) and nitrobenzene (2,500 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO₄, and concentrated. Then, a silica gel column and recrystallization were applied to the concentrate to obtain 125.65 g (yield: 66%) of the product.

(4-2) Synthesis of Sub 1-I-4

Sub 1-I-I-4 (125.65 g, 327.3 mmol), bis(pinacolato)diboron (124.67 g, 491.0 mmol), Pd₂(dba)₃ (14.99 g, 16.4 mmol), potassium acetate (96.37 g, 981.9 mmol), X-phos (15.60 g, 32.7 mmol) and dioxane (1,200 mL) were placed in a round bottom flask and the mixture was stirred at 100° C. overnight. When the reaction was completed, the reaction product was quenched by adding water and water was removed. Thereafter, the reaction product was filtered under reduced pressure and an organic layer was dried over MgSO₄ and concentrated to obtain 105.81 g (yield: 68%) of the product.

(4-5) Synthesis of Core 2-4

Sub 1-I-4 (105.81 g, 222.6 mmol), Core 1-1 (65.41 g, 289.3 mmol), Pd₂(PPh₃)₄ (7.72 g, 6.7 mmol), K₂CO₃ (92.28 g, 667.7 mmol), toluene (850 mL) and H₂O (400 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO₄, and concentrated. Then, a silica gel column and recrystallization were applied to the concentrate to obtain 71.98 g (yield: 60%) of the product.

(5) Synthesis of Core 2-5

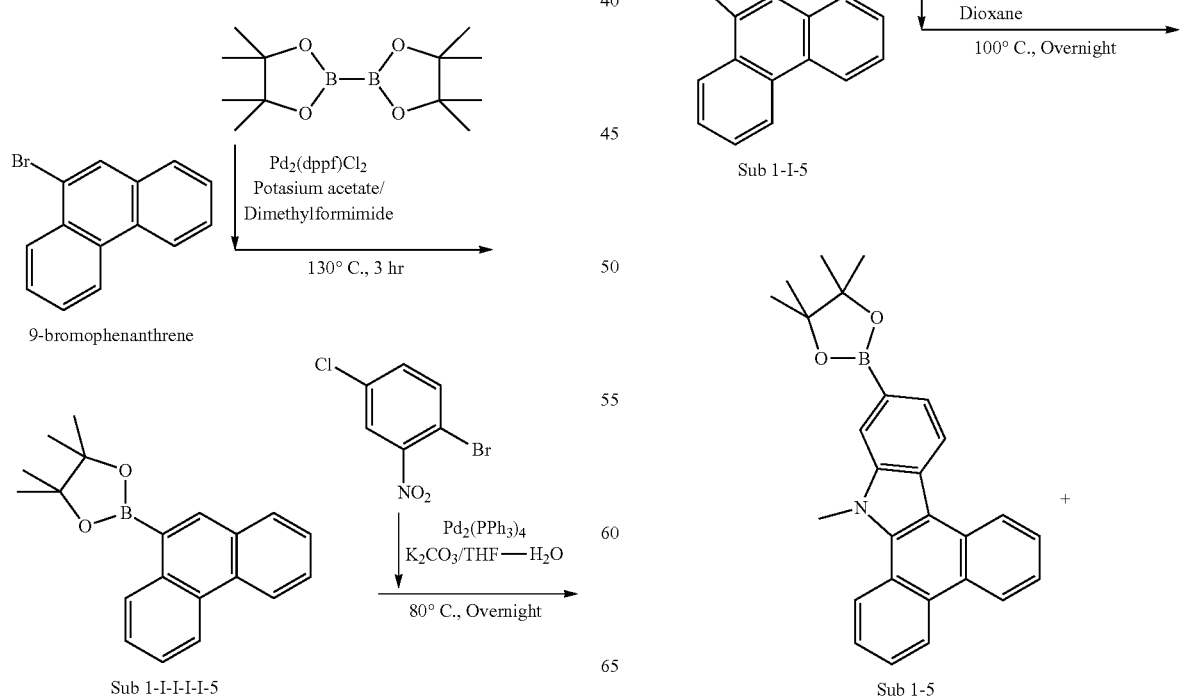

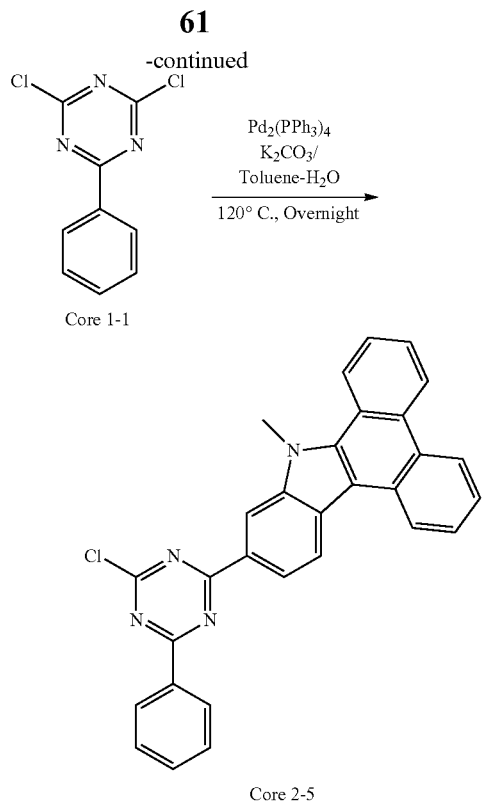

Core 1-1

Core 2-5

(5-1) Synthesis of Sub 1-I-I-I-5

9-bromophenanthrene (150.0 g, 583.4 mmol), bis(pinacolato)diboron (162.95 g, 641.7 mmol), PdCl$_2$(dppf) (14.29 g, 17.5 mmol), potassium acetate (171.75 g, 1750.1 mmol) and toluene (3,000 mL) were placed in a round bottom flask and the mixture was stirred at 130° C. for 3 hours. When the reaction was completed, the reaction product was quenched by adding water and water was removed. Thereafter, the reaction product was filtered under reduced pressure and an organic layer was dried over MgSO$_4$ and concentrated to obtain 141.97 g (yield: 80%) of the product.

(5-2) Synthesis of Sub 1-I-I-I-5

Sub 1-I-I-I-I-5 (141.97 g, 466.7 mmol), 1-bromo-4-chloro-2-nitrobenzene (165.53 g, 700.0 mmol), Pd$_2$(PPh$_3$)$_4$ (16.18 g, 14.0 mmol), K$_2$CO$_3$ (193.51 g, 1,400.1 mmol), THF (2,000 mL) and H$_2$O (1,000 mL) were placed in a round bottom flask. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 121.50 g (yield: 78%) of the product.

(5-3) Synthesis of Sub 1-I-I-5

Sub 1-I-I-I-5 (121.50 g, 364.0 mmol), triphenylphosphine (286.44 g, 1,092.1 mmol) and 1,2-dichlorobenzene (1,800 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 99.96 g (yield: 91%) of the product.

(5-4) Synthesis of Sub 1-I-5

Sub 1-I-I-5 (99.96 g, 331.2 mmol), iodomethane (235.09 g, 1,656.2 mmol), KOH (55.76 g, 993.7 mmol) and dimethylsulfoxide (1,600 mL) were placed in a round bottom flask. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 88.92 g (yield: 85%) of the product.

(5-5) Synthesis of Sub 1-5

Sub 1-I-5 (88.92 g, 281.6 mmol), bis(pinacolato)diboron (107.25 g, 422.4 mmol), Pd$_2$(dba)$_3$ (12.89 g, 14.1 mmol), potassium acetate (82.90 g, 844.7 mmol), X-phos (13.42 g, 28.2 mmol) and dioxane (1,400 mL) were placed in a round bottom flask and the mixture was stirred at 100° C. overnight. When the reaction was completed, the reaction product was quenched by adding water and water was removed. Thereafter, the reaction product was filtered under reduced pressure and an organic layer was dried over MgSO$_4$ and concentrated to obtain 75.69 g (yield: 66%) of the product.

(5-6) Synthesis of Core 2-5

Sub 1-5 (75.69 g, 185.8 mmol), Core 1-1 (54.61 g, 241.6 mmol), Pd$_2$(PPh$_3$)$_4$ (6.44 g, 5.6 mmol), K$_2$CO$_3$ (77.05 g, 557.5 mmol), toluene (1,000 mL) and H$_2$O (500 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 61.26 g (yield: 70%) of the product.

(6) Synthesis Example of Core 2-15

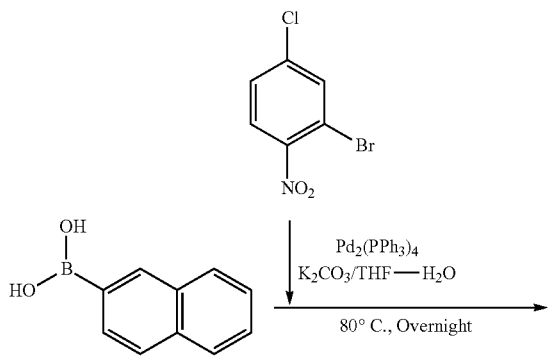

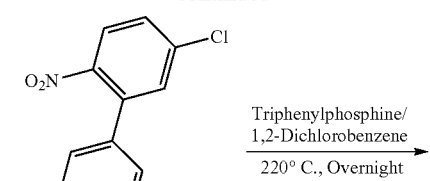

Sub 1-I-I-I-15

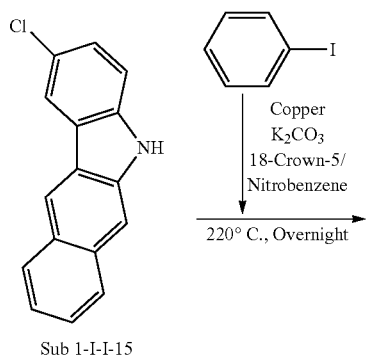

Sub 1-I-I-15

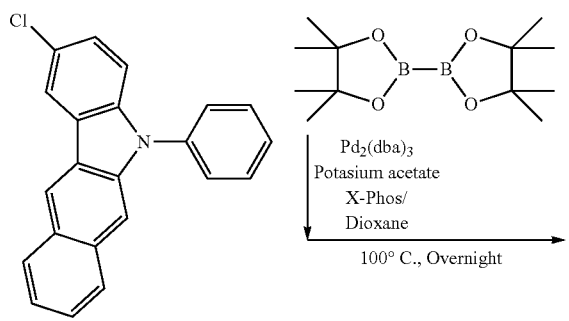

Sub 1-I-15

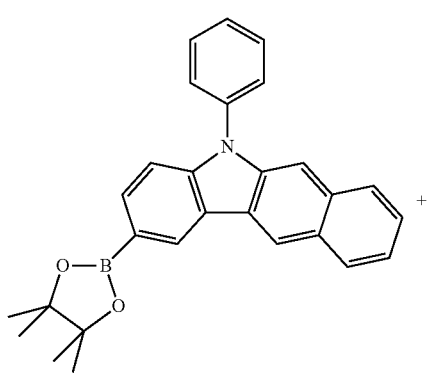

Sub 1-16

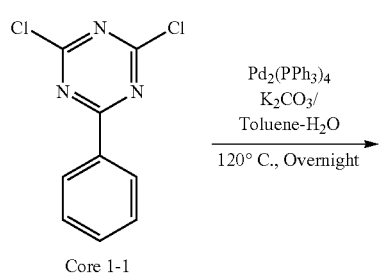

Core 1-1

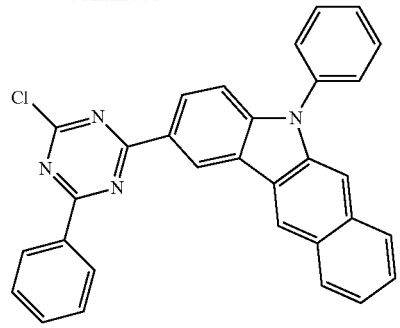

Core 2-15

(6-1) Synthesis of Sub 1-I-I-I-15

Naphthalen-2-ylboronic acid (100.0 g, 581.4 mmol), 2-bromo-4-chloro-1-nitrobenzene (274.96 g, 1,162.9 mmol), $Pd_2(PPh_3)_4$ (20.16 g, 17.4 mmol), $K_2CO_3$ (241.08 g, 1,744.3 mmol), toluene (3,000 mL) and $H_2O$ (1,500 mL) were placed in a round bottom flask. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$, and concentrated. Then, a silica gel column and recrystallization were applied to the concentrate to obtain 127.02 (yield: 77%) of the product.

(6-2) Synthesis of Sub 1-I-I-15

Sub 1-I-I-I-15 (127.02 g, 447.7 mmol), triphenylphosphine (352.29 g, 1,343.1 mmol) and 1,2-dichlorobenzene (2,200 mL) were placed in a round bottom flask. After the mixture was heated to 220° C. and dissolved, the solution was stirred overnight. When the reaction was completed, the reaction product was concentrated under reduced pressure and quenched by adding water. Then, solid was obtained by filtering the reaction product and water was removed from the filtrate. The filtrate was filtered under reduced pressure and dried over $MgSO_4$. Thereafter, the product is concentrated and separated by a silica gel column to obtain two types of isomers. Among them, the lower spot on TLC (Methylene chloride:hexane=1:3) phase is separated and recrystallized to obtain 48.46 g of the product (yield: 43%).

(6-3) Synthesis of Sub 1-I-15

Sub 1-I-I-15 (48.46 g, 192.5 mmol), iodobenzene (196.38 g, 962.6 mmol), Copper (1.22 g, 19.3 mmol), 18-Crown-6 (3.47 g, 9.6 mmol), $K_2CO_3$ (79.83 g, 577.6 mmol) and nitrobenzene (900 mL) were placed in a round bottom flask. After the mixture was heated to 220° C. and dissolved, the solution was stirred overnight. When the reaction was completed, the reaction product was concentrated under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 59.95 g (yield: 88%) of the product.

(6-4) Synthesis of Sub 1-15

Sub 1-I-15 (59.95 g, 169.4 mmol), bis(pinacolato)diboron (64.53 g, 254.1 mmol), $Pd_2(dba)_3$ (7.76 g, 8.5 mmol), potassium acetate (49.88 g, 508.3 mmol), X-phos (8.08 g, 16.9 mmol) and dioxane (850 mL) were placed in a round bottom flask and the mixture was stirred at 100° C. overnight. When the reaction was completed, the reaction product was quenched by adding water and water was removed. Thereafter, the reaction product was filtered under reduced pressure and an organic layer was dried over $MgSO_4$ and concentrated to obtain 48.31 g (yield: 68%) of the product.

(6-5) Synthesis of Core 2-15

Sub 1-15 (48.31 g, 115.2 mmol), Core 1-1 (33.86 g, 149.8 mmol), $Pd_2(PPh_3)_4$ (3.99 g, 3.5 mmol), $K_2CO_3$ (47.77 g, 345.6 mmol), toluene (550 mL) and $H_2O$ (275 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 39.88 g (yield: 68%) of the product.

(7) Synthesis Example of Core 2-35

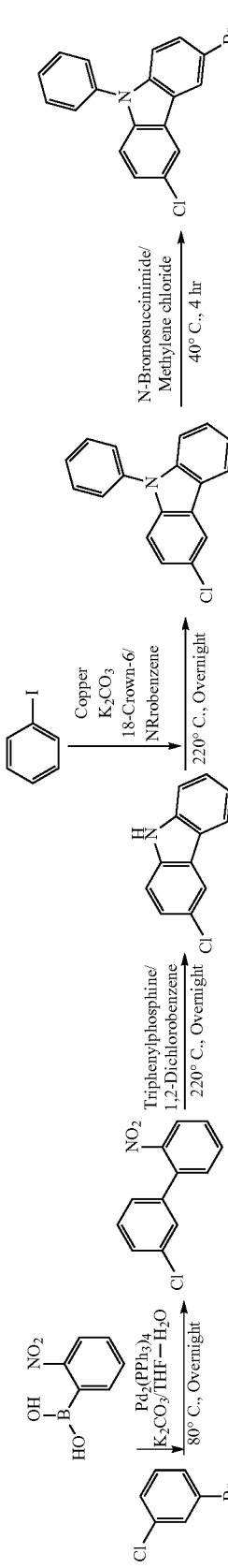
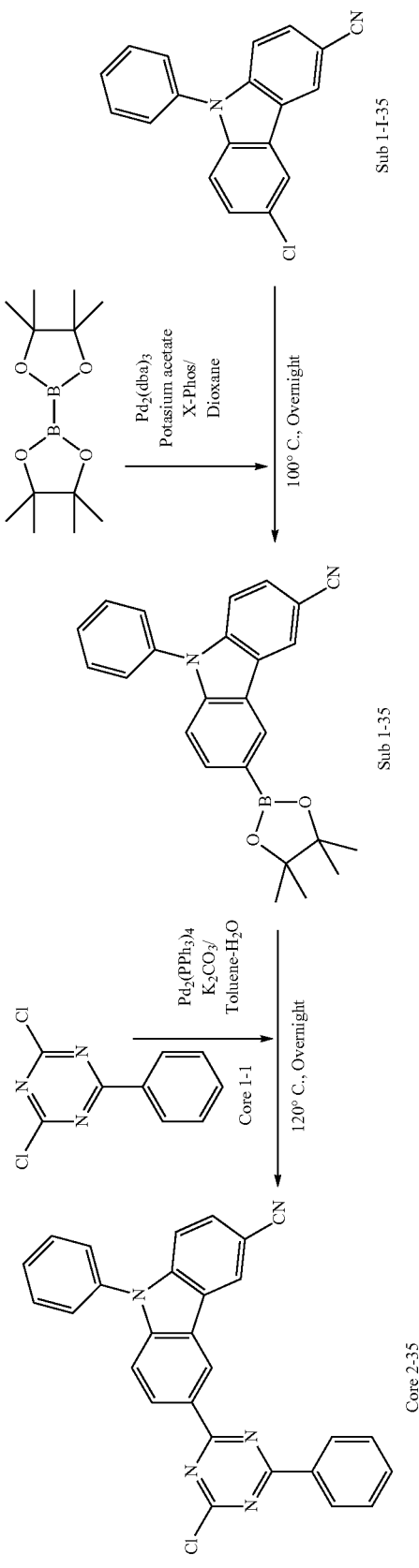

(7-1) Synthesis of Sub 1-I-I-I-I-I-35

1-bromo-3-chlorobenzene (150.0 g, 783.5 mmol), (2-nitrophenyl)boronic acid (130.79 g, 783.5 mmol), $Pd_2(PPh_3)_4$ (27.16 g, 23.5 mmol), $K_2CO_3$ (324.86 g, 2,350.5 mmol) and tetrahydrofuran (4,000 mL), $H_2O$ (2,000 mL) were placed in a round bottom flask. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 129.98 g (yield: 71%) of the product.

(7-2) Synthesis of Sub 1-I-I-I-I-35

Sub 1-I-I-I-I-I-35 (129.98 g, 556.3 mmol), triphenylphosphine (437.74 g, 1,668.9 mmol) and 1,2-dichlorobenzene (2,500 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 97.60 g (yield: 87%) of the product.

(7-3) Synthesis of Sub 1-I-I-I-35

Sub 1-I-I-I-I-35 (97.60 g, 484.0 mmol), iodobenzene (493.71 g, 2,420.0 mmol), Copper (3.08 g, 48.4 mmol), 18-Crown-6 (8.72 g, 24.2 mmol), $K_2CO_3$ (200.68 g, 1,452.0 mmol) and nitrobenzene (2,500 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 111.58 g (yield: 83%) of the product.

(7-4) Synthesis of Sub 1-I-I-35

Sub 1-I-I-I-35 (111.58 g, 401.7 mmol), N-bromosuccinimide (78.65 g, 441.9 mmol) and methylene chloride (2,000 mL) were placed in a round bottom flask. After the mixture was heated to 40° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 70.21 g (yield: 49%) of the product.

(7-5) Synthesis of Sub 1-I-35

Sub 1-I-I-35 (70.21 g, 196.9 mmol) and CuCN (57.85 g, 255.9 mmol) were dissolved in 1,000 mL of dimethylformimide and stirred at 150° C. for 24 hours. After cooling the reaction solution to room temperature, 60 mL of ammonia water and 60 mL of water were added, followed by extraction with 50 mL of $CH_2Cl_2$ three times. The collected organic layer was dried over $MgSO_4$, and a silica gel column and recrystallized were applied to the product obtained by evaporating the solvent to obtain 53.05 g (yield 89%) of the product.

(7-6) Synthesis of Sub 1-35

Sub 1-I-35 (53.05 g, 175.2 mmol), bis(pinacolato)diboron (66.74 g, 262.8 mmol), $Pd_2(dba)_3$ (8.02 g, 8.8 mmol), potassium acetate (51.59 g, 525.7 mmol), X-phos (8.35 g, 17.5 mmol) and dioxane (870 mL) were placed in a round bottom flask and the mixture was stirred overnight at 100° C. When the reaction was completed, the reaction product was quenched by adding water and water was removed. Thereafter, the reaction product was filtered under reduced pressure and an organic layer was dried over $MgSO_4$ and concentrated to obtain 58.72 g (yield: 85%) of the product.

(7-7) Synthesis of Core 2-35

Sub 1-35 (58.72 g, 148.9 mmol), Core 1-1 (43.77 g, 193.6 mmol), $Pd_2(PPh_3)_4$ (5.16 g, 4.5 mmol), $K_2CO_3$ (61.75 g, 446.8 mmol) and toluene (750 mL), $H_2O$ (300 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over $MgSO_4$ and concentrated. Then, a silica gel column and recrystallization were applied to the concentrate to obtain 60.01 g (yield: 88%) of the product.

(8) Synthesis Example of Core 2-37

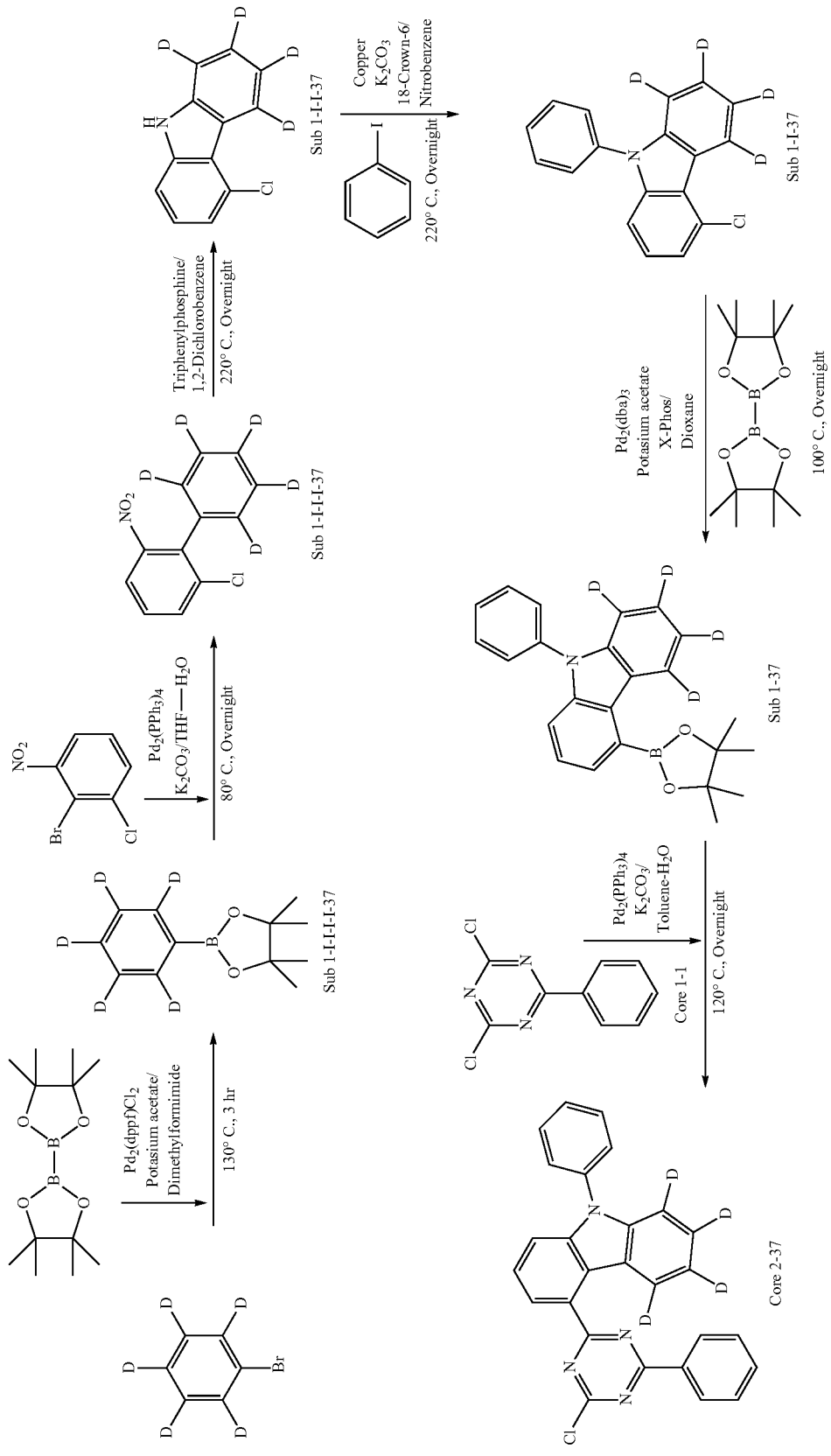

(8-1) Synthesis of Sub 1-I-I-I-I-37

1-bromobenzene-2,3,4,5,6-d$_5$ (200.0 g, 1,234.3 mmol), bis(pinacolato)diboron (344.77 g, 1,357.7 mmol), PdCl$_2$(dppf) (30.24 g, 37.0 mmol), potassium acetate (363.39 g, 3,702.8 mmol) and dimethylformimide (5,000 mL) were placed in a round bottom flask and the mixture was stirred for 3 hours at 130° C. When the reaction was completed, water was removed from the reaction product. Thereafter, the reaction product was filtered under reduced pressure and an organic layer was dried over MgSO$_4$ and concentrated to obtain 234.87 g (yield: 91%) of the product.

(8-2) Synthesis of Sub 1-I-I-I-37

Sub 1-I-I-I-I-37 (234.87 g, 1,123.2 mmol), 2-Bromo-1-chloro-nitrobenzene (398.37 g, 1,684.8 mmol), Pd$_2$(PPh$_3$)$_4$ (38.94 g, 33.7 mmol), K$_2$CO$_3$ (465.71 g, 3,369.6 mmol), tetrahydrofuran (5,000 mL) and H$_2$O (2,500 mL) were placed in a round bottom flask. After the mixture was heated to 80° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 163.53 g (yield: 61%) of the product.

(8-3) Synthesis of Sub 1-I-I-37

Sub 1-I-I-I-37 (163.53 g, 685.1 mmol), triphenylphosphine (539.12 g, 2,055.4 mmol) and 1,2-dichlorobenzene (3,500 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$, and concentrated. Then, a silica gel column and recrystallization were applied to the concentrate to obtain 125.04 g (yield: 89%) of the product.

(8-4) Synthesis of Sub 1-I-37

Sub 1-I-I-37 (125.04 g, 609.8 mmol), iodobenzene (204.01 g, 3,048.9 mmol), Copper (3.88 g, 61.0 mmol), 18-Crown-6 (10.99 g, 30.5 mmol), K$_2$CO$_3$ (252.83 g, 1,829.3 mmol) and nitrobenzene (3,000 mL) were placed in a round bottom flask. After the mixture was heated to 220° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$ and concentrated. Then, a silica gel column and recrystallization were applied to the concentrate to obtain 123.71 g (yield: 72%) of the product.

(8-5) Synthesis of Sub 1-37

Sub 1-I-37 (123.71 g, 439.0 mmol), bis(pinacolato)diboron (167.23 g, 658.5 mmol), Pd$_2$(dba)$_3$ (20.10 g, 22.0 mmol), potassium acetate (129.26 g, 1,317.1 mmol), X-phos (20.93 g, 43.9 mmol), dioxane (2,000 mL) were placed in a round bottom flask and the mixture was stirred overnight at 100° C. When the reaction was completed, the product was quenched by adding water and water was removed. Thereafter, the reaction product was filtered under reduced pressure and an organic layer was dried over MgSO$_4$ and concentrated to obtain 108.17 g (yield: 66%) of the product.

(8-6) Synthesis of Core 2-37

Sub 1-37 (108.17 g, 289.8 mmol), Core 1-1 (85.16 g, 376.7 mmol), Pd$_2$(PPh$_3$)$_4$ (10.05 g, 8.7 mmol), K$_2$CO$_3$ (120.15 g, 869.3 mmol), toluene (1,400 mL) and H$_2$O (700 mL) were placed in a round bottom flask. After the mixture was heated to 120° C. and dissolved, the solution was stirred overnight. When the reaction was completed, the reaction product was filtered under reduced pressure and quenched by adding water. Thereafter, the product was filtered to obtain a solid and the filtrate was collected. After water is removed from the filtrate, the filtrate was filtered under reduced pressure, dried over MgSO$_4$ and concentrated. Then, a silica gel column and recrystallization were applied to the concentrate to obtain 83.56 g (yield: 66%) of the product.

II. Synthesis Example of Sub 2

Compounds belonging to Sub 2 of Scheme 1 are as follows, but are not limited thereto, and FD-MS values of the following compounds are shown in Table 3 below.

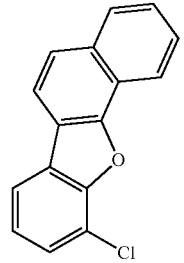

Sub 2-1

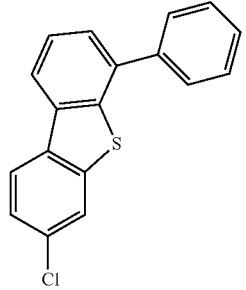

Sub 2-2

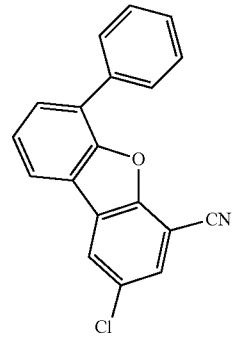

Sub 2-3

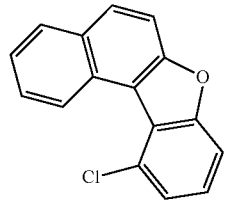

Sub 2-4

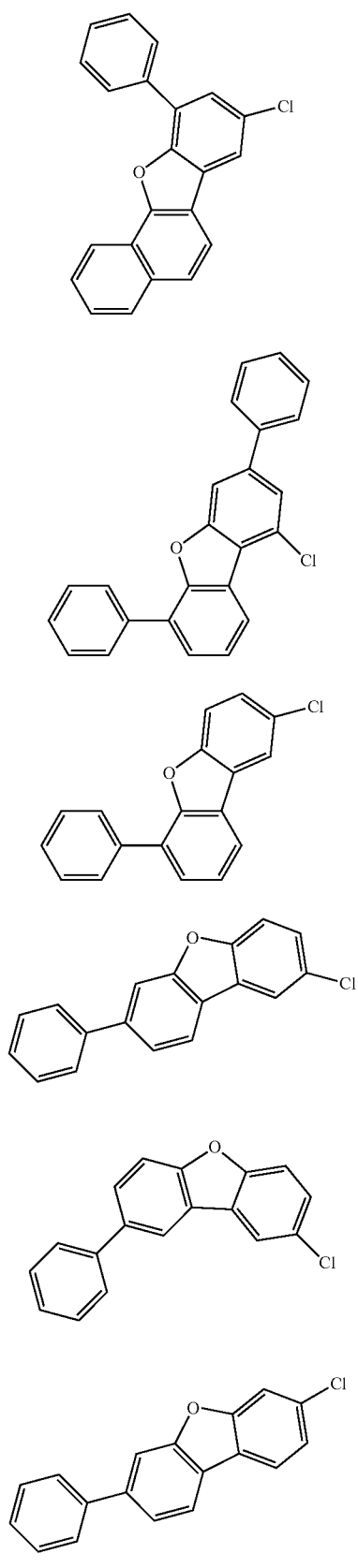

Sub 2-17
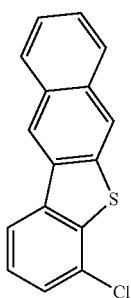
Sub 2-18
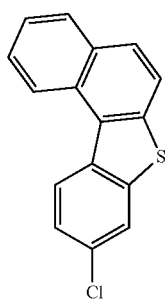
Sub 2-19
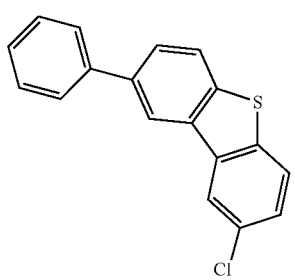
Sub 2-20
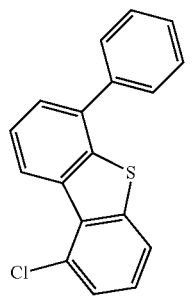
Sub 2-21
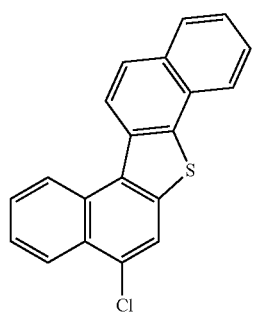
Sub 2-22
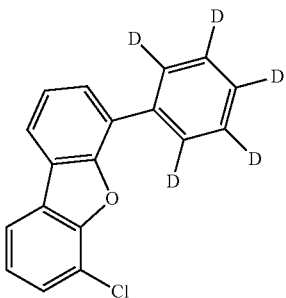
Sub 2-23
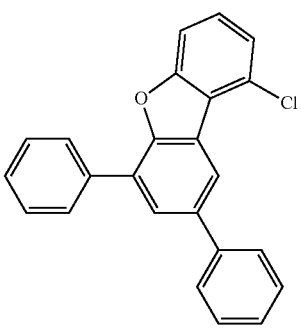
Sub 2-24
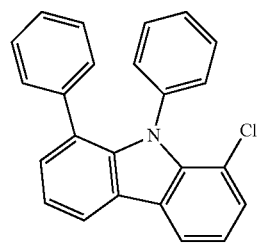
Sub 2-25
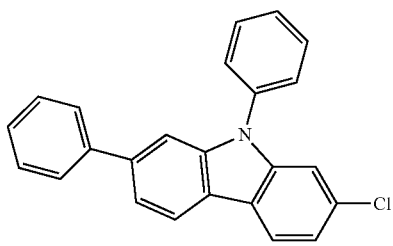
Sub 2-26
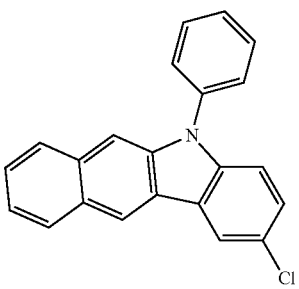

Sub 2-27
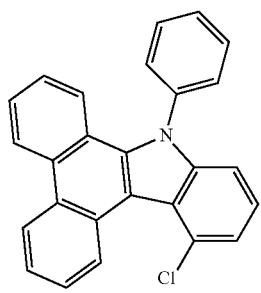
Sub 2-28
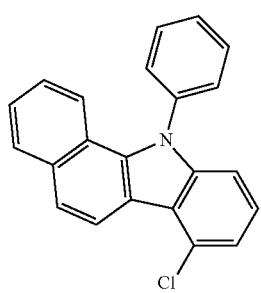
Sub 2-29
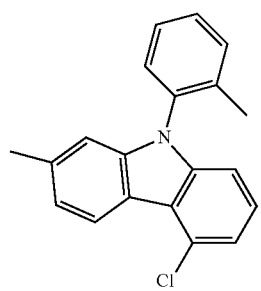
Sub 2-30
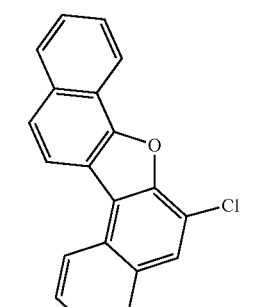
Sub 2-31
Sub 2-32
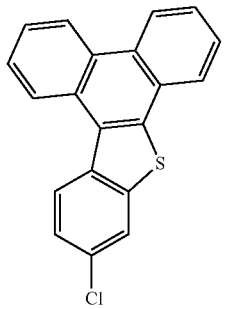
Sub 2-33
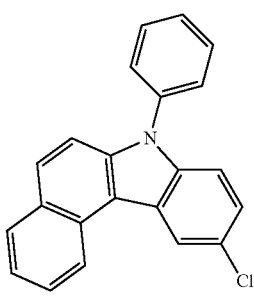
Sub 2-34
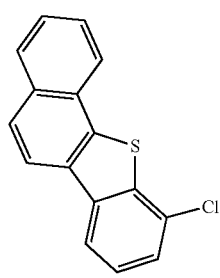
Sub 2-35
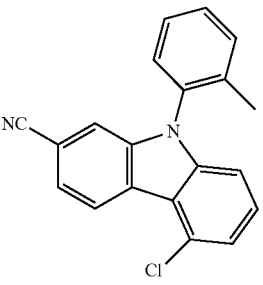
Sub 2-36
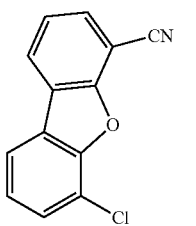

TABLE 3

| Compound | FD-MS | Compound | FD-MS |
|---|---|---|---|
| Sub 2-2 | m/z = 294.03 ($C_{18}H_{11}ClS$ = 294.80) | Sub 2-8 | m/z = 278.05 ($C_{18}H_{11}ClO$ = 278.74) |
| Sub 2-15 | m/z = 252.03 ($C_{16}H_9ClO$ = 252.70) | Sub 2-16 | m/z = 302.05 ($C_{20}H_{11}ClO$ = 302.76) |
| Sub 2-21 | m/z = 318.03 ($C_{20}H_{11}ClS$ = 318.82) | Sub 2-22 | m/z = 283.08 ($C_{18}H_6D_5ClO$ = 283.77) |
| Sub 2-28 | m/z = 327.08 ($C_{22}H_{14}ClN$ = 327.81) | Sub 2-29 | m/z = 305.10 ($C_{20}H_{16}ClN$ = 305.81) |

Synthesis examples of compounds belonging to Sub 2 are as follows.

1. Synthesis Example of Sub 2-3

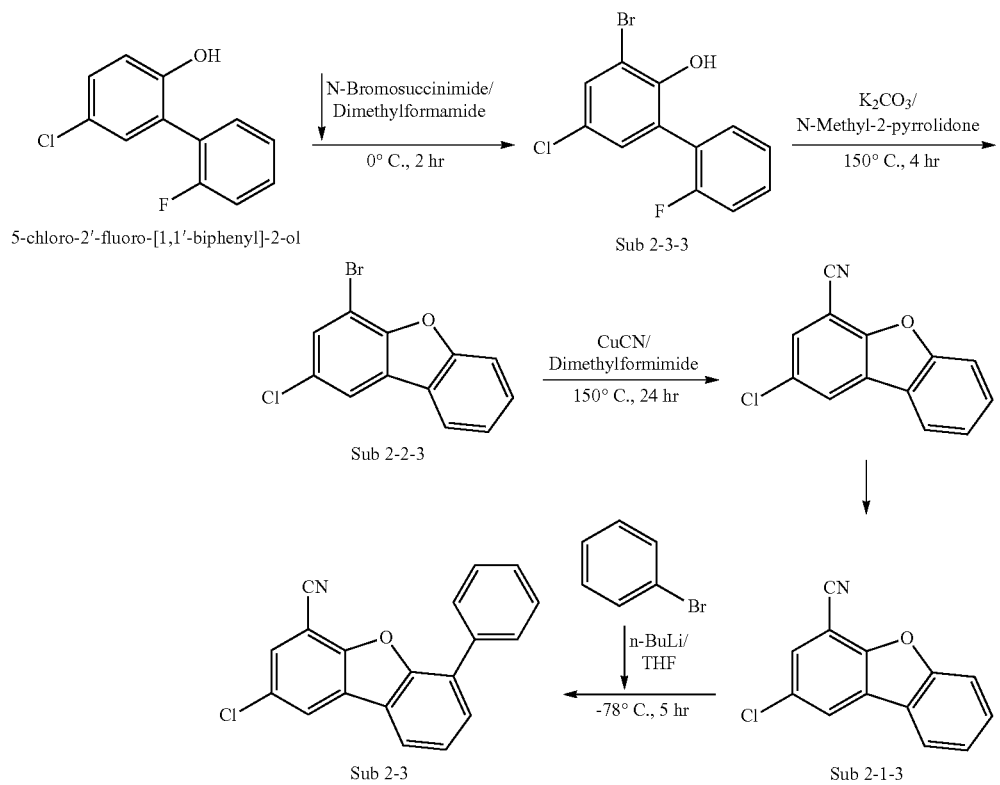

(1) Synthesis of Sub 2-3-3

5-chloro-2'-fluoro-[1,1'-biphenyl]-2-ol (100.0 g, 449.2 mmol), N-bromosuccinimide (87.94 g, 494.1 mmol) and methylene chloride (2,200 mL) were placed in a round bottom flask and the mixture was stirred at 0° C. for two hours. When the reaction was completed, water was removed from the reaction product. Thereafter, the reaction product was filtered under reduced pressure, dried over MgSO$_4$ and concentrated. Then, a silica gel column and recrystallization were applied to the concentrate to obtain 104.32 g (yield: 77%) of the product.

(2) Synthesis of Sub 2-2-3

Sub 2-3-3 (104.32 g, 345.8 mmol), K$_2$CO$_3$ (143.4 g, 1,037.5 mmol) and N-Methyl-2-pyrrolidone (1,700 mL) were placed in a round bottom flask. After the mixture was heated to 150° C. and dissolved, the solution was stirred for 4 hours. When the reaction was completed, the reaction product was filtered under reduced pressure and quenched by adding water. Then, water was removed from the reaction product and the reaction product was filtered under reduced pressure. The filtrate was dried over MgSO$_4$ and concentrated. Then, a silica gel column and recrystallization were applied to the concentrate to obtain 37.0 g (yield: 38%) of the product.

(3) Synthesis of Sub 2-1-3

Sub 2-2-3 (37.0 g, 131.4 mmol), CuCN (38.62 g, 170.9 mmol) and dimethylformimide (790 mL) were placed in a round bottom flask. After the mixture was heated to 150° C. and dissolved, the solution was stirred for 24 hours. When the reaction was completed, the reaction product was filtered by silicagel filter and quenched by adding water. Then, water was removed from the reaction product and the reaction product was filtered under reduced pressure. The filtrate was dried over MgSO$_4$ and concentrated. Then, a silica gel column and recrystallization were applied to the concentrate to obtain 27.23 (yield: 91%) of the product.

(4) Synthesis of Sub 2-3

After bromobenzene (28.17 g, 179.4 mmol) was dissolved in THF (1,000 mL), the temperature of the reaction mixture was lowered to −78° C. and n-BuLi (12.26 mL, 2.5M in hexane) was slowly added dropwise to the reaction mixture. Then, the mixture was stirred for 1 hour. Sub 2-1-3 (27.23 g, 119.6 mmol) was dissolved in THF and the solution was added to the mixture. Then, the mixture was stirred at room temperature for 4 hours. When the reaction was completed, the reaction product was quenched by adding water. Then, water was removed from the reaction product and the reaction product was filtered under reduced pressure. The filtrate was dried over MgSO₄ and concentrated. Then, a silica gel column and recrystallization were applied to the concentrate to obtain 16.35 g (yield: 45%) of the product.

2. Synthesis Example of Sub 2-7

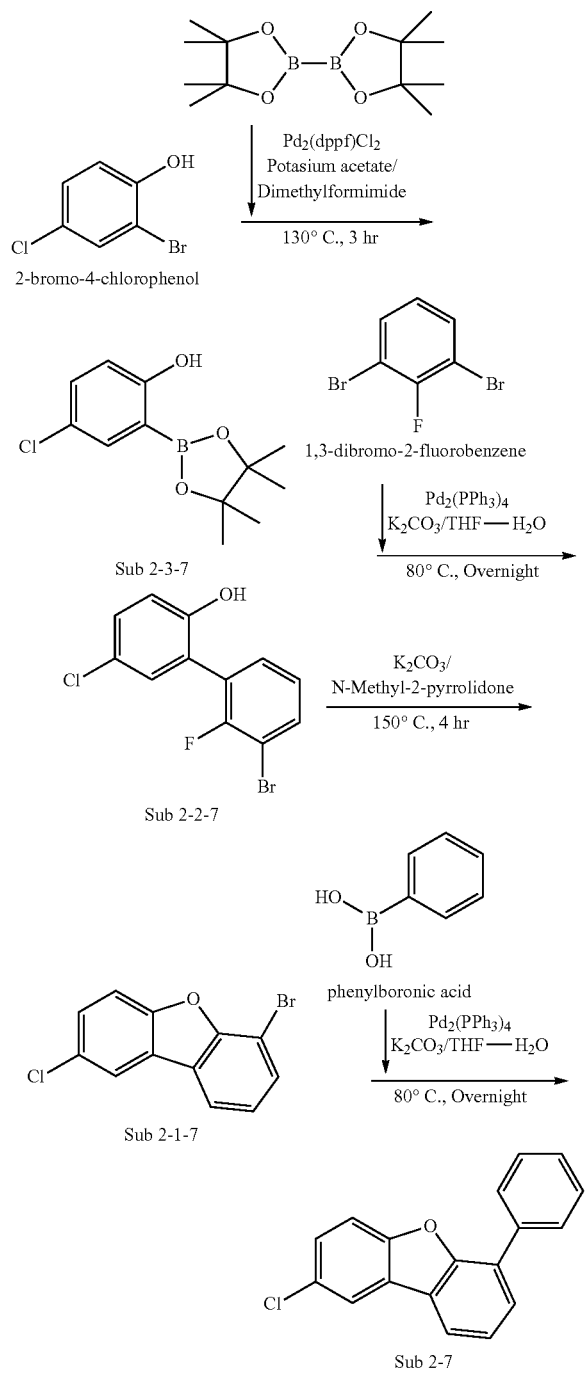

(1) Synthesis of Sub 2-3-7

2-bromo-4-chlorophenol (100.0 g, 482.0 mmol), bis(pinacolato)diboron (134.65 g, 530.2 mmol), PdCl₂(dppf) (11.81 g, 14.5 mmol), potassium acetate (141.92 g, 1,446.1 mmol) and dimethylformimide (5,000 mL) were placed in a round bottom flask and the mixture was stirred for 3 hours at 130° C. When the reaction was completed, the reaction product was quenched by adding water and water was removed. Then, the reaction product was filtered under reduced pressure, the filtrate was dried over MgSO₄ and concentrated. Then, a silica gel column and recrystallization were applied to the concentrate to obtain 96.89 g (yield: 79%) of the product.

(2) Synthesis of Sub 2-2-7

Sub 2-3-7 (96.89 g, 321.2 mmol), 1,3,-dibromo-2-fluorobenzene (122.33 g, 481.8 mmol), Pd₂(PPh₃)₄ (11.14 g, 9.6 mmol), K₂CO₃ (133.18 g, 963.6 mmol), tetrahydrofuran (1,500 mL) and H₂O (750 mL) were placed in a round bottom flask. After the mixture was heated to 80° C. and dissolved, the solution was stirred overnight. When the reaction was completed, the reaction product was concentrated under reduced pressure and quenched by adding water. Thereafter, the product was filtered to obtain a solid and the filtrate was collected. After water is removed from the filtrate, the filtrate was filtered under reduced pressure, dried over MgSO₄ and concentrated. Then, a silica gel column and recrystallization were applied to the concentrate to obtain 68.77 g (yield: 71%) of the product.

(2) Synthesis of Sub 2-1-7

Sub 2-2-7 (68.77 g, 228.1 mmol), K₂CO₃ (94.56 g, 684.2 mmol), N-Methyl-2-pyrrolidone (1,200 mL) were placed in a round bottom flask. After the mixture was heated to 150° C. and dissolved, the solution was stirred for 4 hours. When the reaction was completed, the reaction product was concentrated under reduced pressure and quenched by adding water. Thereafter, the reaction product was filtered to obtain a solid and the filtrate was collected. After water is removed from the filtrate, the filtrate was filtered under reduced pressure, dried over MgSO₄ and concentrated. Then, a silica gel column and recrystallization were applied to the concentrate to obtain 57.14 g (yield: 89%) of the product.

(3) Synthesis of Sub 2-7

Sub 2-1-7 (57.14 g, 203.0 mmol), phenylboronic acid (27.22 g, 223.3 mmol), Pd₂(PPh₃)₄ (7.04 g, 6.1 mmol), K₂CO₃ (84.15 g, 608.9 mmol), tetrahydrofuran (1,000 mL) and H₂O (500 mL) were placed in a round bottom flask. After the mixture was heated to 80° C. and dissolved, the solution was stirred overnight. When the reaction was completed, the reaction product was concentrated under reduced pressure and quenched by adding water. Thereafter, the reaction product was filtered to obtain a solid and the filtrate was collected. After water is removed from the filtrate, the filtrate was filtered under reduced pressure, dried over MgSO₄ and concentrated. Then, a silica gel column and recrystallization were applied to the concentrate to obtain 40.73 g (yield: 72%) of the product.

3. Synthesis Example of Sub 2-16

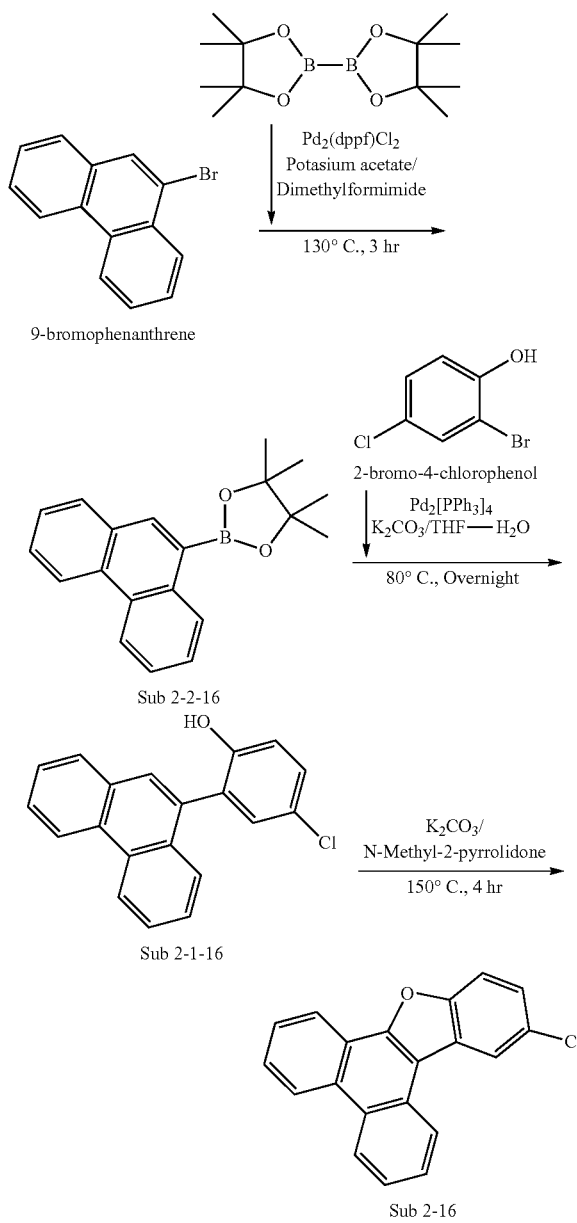

(1) Synthesis of Sub 2-2-16

9-phenanthrene (100.0 g, 388.9 mmol), bis(pinacolato)diboron (108.64 g, 427.8 mmol), PdCl$_2$(dppf) (9.53 g, 11.7 mmol), potassium acetate (114.50 g, 1,166.7 mmol), and dimethylformimide (2,000 mL) were placed in a round bottom flask and the mixture was stirred for 3 hours at 130° C. When the reaction was completed, the reaction product was quenched by adding water and water was removed. Then, after the reaction product was filtered under reduced pressure, an organic layer was dried over MgSO$_4$ and concentrated to obtain 92.28 g (yield: 78%) of the product.

(2) Synthesis of Sub 2-1-16

Sub 2-2-16 (92.28 g, 303.4 mmol), 2-bromo-4-chlorophenol (94.40 g, 455.0 mmol), Pd$_2$(PPh$_3$)$_4$ (10.52 g, 9.1 mmol), K$_2$CO$_3$ (125.78 g, 910.1 mmol), tetrahydrofuran (1,500 mL) and H$_2$O (750 mL) were placed in a round bottom flask. After the mixture was heated to 80° C. and dissolved, the solution was stirred overnight. When the reaction was completed, the reaction product was concentrated under reduced pressure and quenched by adding water. Thereafter, the reaction product was filtered to obtain a solid and the filtrate was collected. After water is removed from the filtrate, the filtrate was filtered under reduced pressure, dried over MgSO$_4$ and concentrated. Then, a silica gel column and recrystallization were applied to the concentrate to obtain 78.58 g (yield: 85%) of the product.

(3) Synthesis of Sub 2-16

Sub 2-1-16 (78.58 g, 257.8 mmol), K$_2$CO$_3$ (106.9 g, 773.5 mmol) and N-Methyl-2-pyrrolidone (1,200 mL) were placed in a round bottom flask. After the mixture was heated to 150° C. and dissolved, the solution was stirred for 4 hours. When the reaction was completed, the reaction product was concentrated under reduced pressure and quenched by adding water. Then, water was removed from the reaction product and the reaction product was filtered under reduced pressure. The filtrate was dried over MgSO$_4$ and concentrated. Then, a silica gel column and recrystallization were applied to the concentrate to obtain 35.13 g (yield: 45%) of the product.

4. Synthesis Example of Sub 2-22

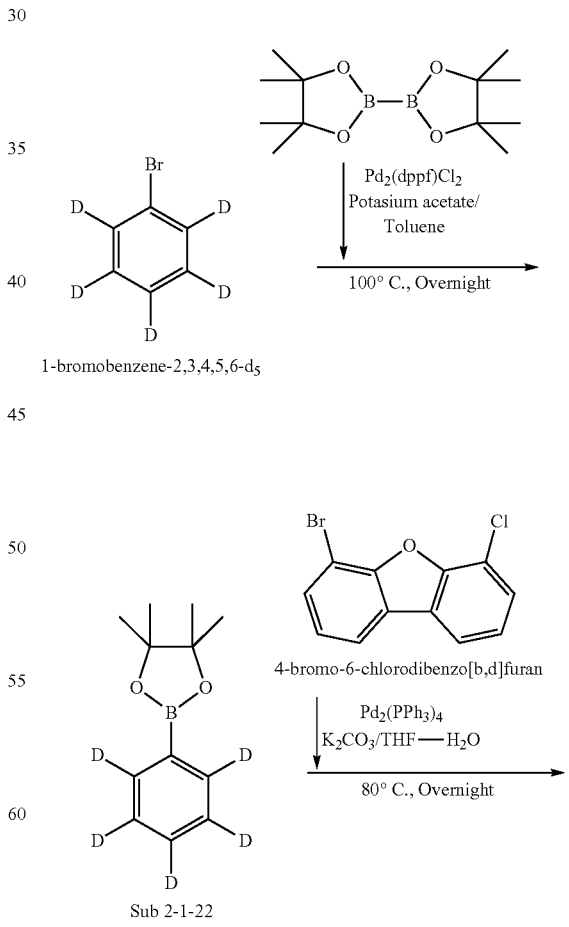

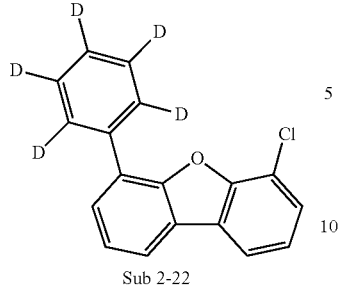

Sub 2-22

(1) Synthesis of Sub 2-1-22

1-bromonezene-2,3,4,5,6-d$_5$ (100 g, 617.1 mmol), bis(pinacolato)diboron (235.07 g, 925.7 mmol), Pd(dppf)Cl$_2$ (15.12 g, 18.5 mmol) and potassium acetate (181.70 g, 1,851 mmol) were placed in a round bottom flask and toluene (3,000 mL) was added thereto. The mixture was stirred at 100° C. overnight. When the reaction was completed, the reaction product was quenched by adding water and water was removed from the reaction product. Then, after the reaction product was filtered under reduced pressure, an organic layer was dried over MgSO$_4$ and concentrated to obtain 112.27 g (yield: 87%) of the product.

(2) Synthesis of Sub 2-22

Sub 2-1-22 (112.27 g, 536.9 mmol), 4-bromo-6-chlorodibenzo[b,d]furan (226.73 g, 805.3 mmol), Pd$_2$(PPh$_3$)$_4$ (18.61 g, 16.1 mmol) and K$_2$CO$_3$ (222.61 g, 1,610.7 mmol) were placed in a round bottom flask and THF (2,500 mL) and H$_2$O (1,750 mL) were added thereto. After the mixture was heated to 80° C. and stirred overnight. When the reaction was completed, water was removed from the reaction product and the reaction product was filtered under reduced pressure. The filtrate was dried over MgSO$_4$ and concentrated. Then, a silica gel column and recrystallization were applied to the concentrate to obtain 103.60 g (yield: 68%) of the product.

5. Synthesis Example of Sub 2-27

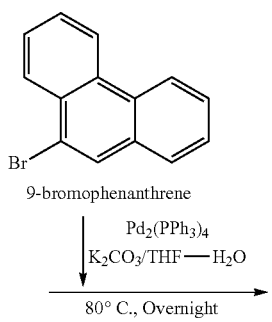

9-bromophenanthrene (2-chloro-6-nitrophenyl)boronic acid

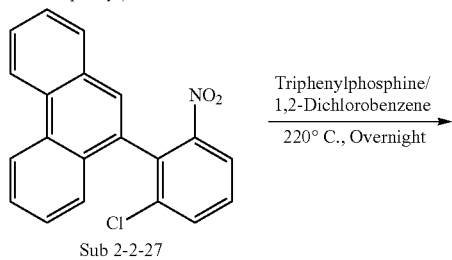

Sub 2-2-27

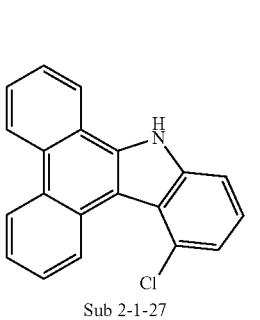

Sub 2-1-27

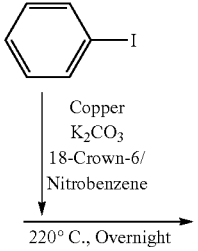

Sub 2-27

(1) Synthesis of Sub 2-2-27

(2-chloro-6-nitrophenyl)boronic acid (50.0 g, 248.3 mmol), 9-bromophenanthrene (95.77 g, 372.4 mmol), Pd$_2$(PPh$_3$)$_4$ (8.61 g, 7.4 mmol), K$_2$CO$_3$ (102.95 g, 744.9 mmol) were placed in a round bottom flask and THF (1,500 mL) and H$_2$O (750 mL) were added thereto. After the mixture was heated to 80° C. and stirred overnight. When the reaction was completed, water was removed from the reaction product and the reaction product was filtered under reduced pressure. The filtrate was dried over MgSO$_4$ and concentrated. Then, a silica gel column and recrystallization were applied to the concentrate to obtain 72.93 g (yield: 88%) of the product.

(2) Synthesis of Sub 2-1-27

Sub 2-2-27 (72.93 g, 218.5 mmol), triphenylphosphine (171.93 g, 655.5 mmol) were placed in a round bottom flask and 1,2-dichlorobenzene (1,300 mL) was added thereto. After the mixture was heated to 220° C. and dissolved, the solution was stirred overnight. When the reaction was completed, the reaction product was concentrated under reduced pressure and quenched by adding toluene and water. Then, water was removed from the reaction product and the reaction product was filtered under reduced pressure. The filtrate was dried over MgSO$_4$ and concentrated. Then, a silica gel column and recrystallization were applied to the concentrate to obtain 54.72 g (yield: 83%) of the product.

(3) Synthesis of Sub 2-27

Sub 2-1-27 (54.72 g, 181.4 mmol), iodobenzene (184.99 g, 906.8 mmol), K$_2$CO$_3$ (75.19 g, 544.1 mmol), copper (1.15 g, 18.1 mmol) and 18-crown-6 (3.27 g, 9.1 mmol) were placed in a round bottom flask and nitrobenzene (1,000 mL) was added thereto. After the mixture was heated to 220° C. and dissolved, the solution was stirred overnight. When the reaction was completed, the reaction product was applied to silicagel filter to obtain a solid. The filtrate was quenched by adding water and water was removed. Then, the filtrate was filtered under reduced pressure, dried over MgSO$_4$ and concentrated. Then, a silica gel column and recrystallization were applied to the concentrate to obtain 47.97 g (yield: 70%) of the product.

III. Synthesis Example of Final Products

1. Synthesis Example of P 1-2

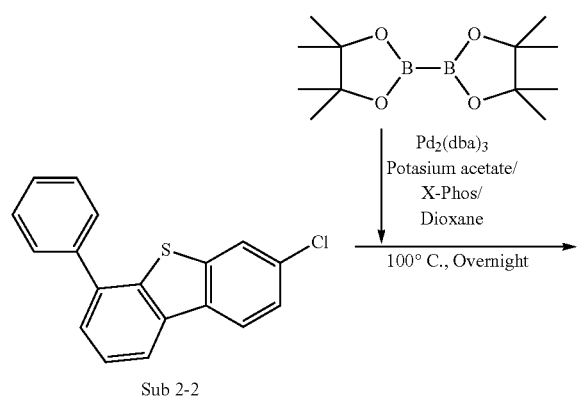

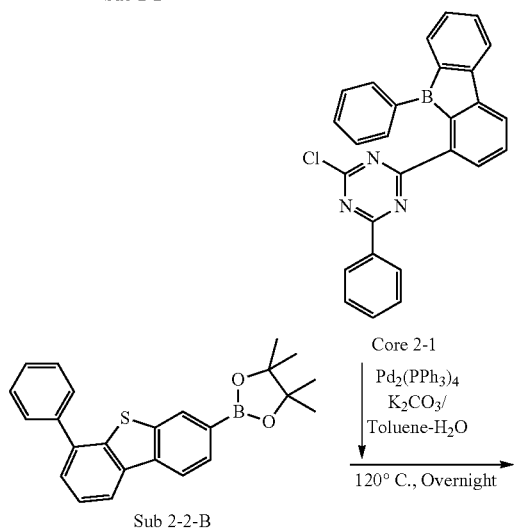

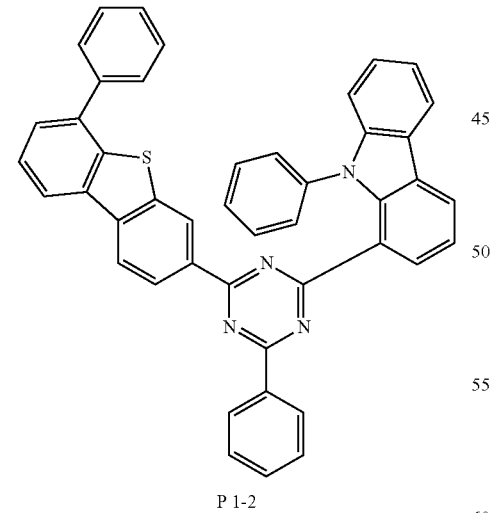

(1) Synthesis of Sub 2-2-B

Sub 2-2 (5.0 g, 17.0 mmol), bis(pinacolato)diboron (6.47 g, 25.5 mmol), Pd$_2$(dba)$_3$ (0.78 g, 0.8 mmol), potassium acetate (5.00 g, 50.9 mmol) and X-phos (0.81 g, 1.7 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO$_4$ and concentrated to obtain 5.77 g (yield: 88%) of the product.

(2) Synthesis of P 1-2

Sub 2-2-B (5.77 g, 14.9 mmol), Core 2-1 (6.47 g, 14.9 mmol), Pd$_2$(PPh$_3$)$_4$ (0.52 g, 0.4 mmol) and K$_2$CO$_3$ (6.19 g, 44.8 mmol) were placed in a round bottom flask. After THF (100 mL) and H$_2$O (50 mL) were added thereto, the mixture was heated to 120° C. and stirred overnight. When the reaction was completed, water in the reaction product was removed and the reaction product was filtered under reduced pressure. The filtrate was dried over MgSO$_4$ and concentrated. Then, a silica gel column and recrystallization were applied to the concentrate to obtain 6.97 g (yield: 71%) of the product.

2. Synthesis Example of P 2-1

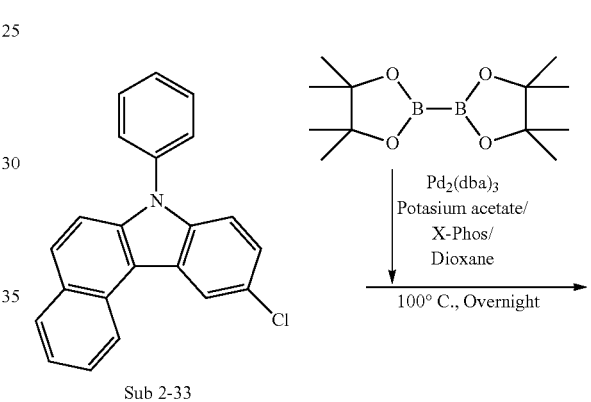

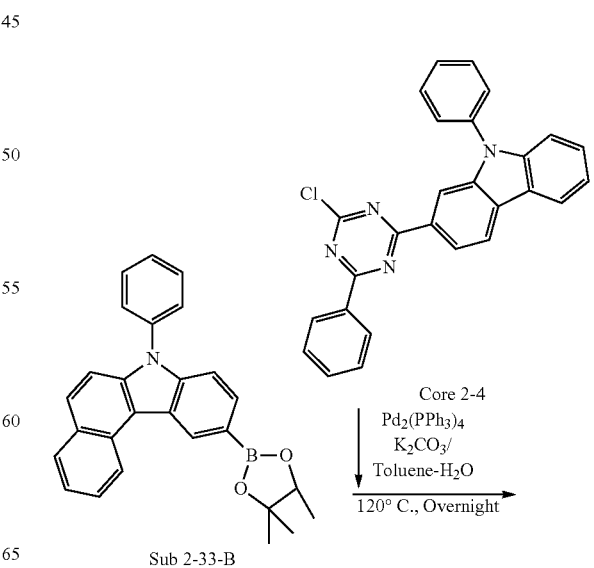

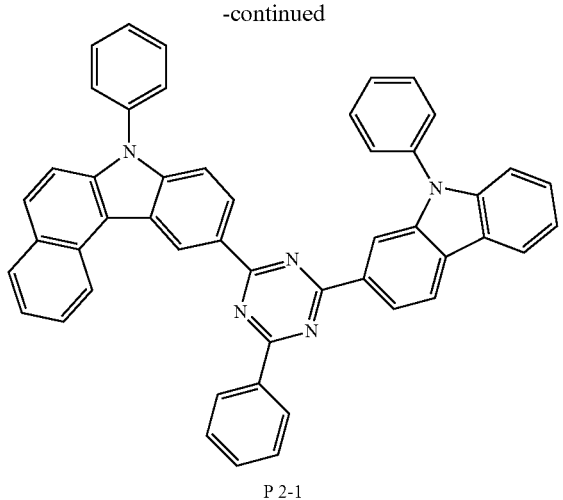

P 2-1

(1) Synthesis of Sub 2-33-B

Sub 2-33 (5.0 g, 15.3 mmol), bis(pinacolato)diboron (5.81 g, 22.9 mmol), Pd$_2$(dba)$_3$ (0.70 g, 0.8 mmol), potassium acetate (4.49 g, 45.8 mmol) and X-phos (0.73 g, 1.5 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO$_4$ and concentrated to obtain 6.40 g (yield: 4.73%) of the product.

(2) Synthesis of P 2-1

Sub 2-33-B (4.73 g, 11.3 mmol), Core 2-4 (4.88 g, 11.3 mmol), Pd$_2$(PPh$_3$)$_4$ (0.39 g, 0.3 mmol) and K$_2$CO$_3$ (4.68 g, 33.8 mmol) were placed in a round bottom flask. After THF (100 mL) and H$_2$O (50 mL) were added thereto, the mixture was heated to 120° C. and stirred overnight. When the reaction was completed, water in the reaction product was removed and the reaction product was filtered under reduced pressure. The filtrate was dried over MgSO$_4$ and concentrated. Then, a silica gel column and recrystallization were applied to the concentrate to obtain 5.60 g (yield: 72%) of the product.

3. Synthesis Example of P 2-2

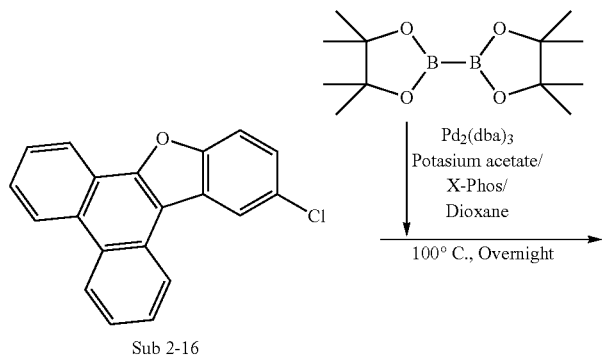

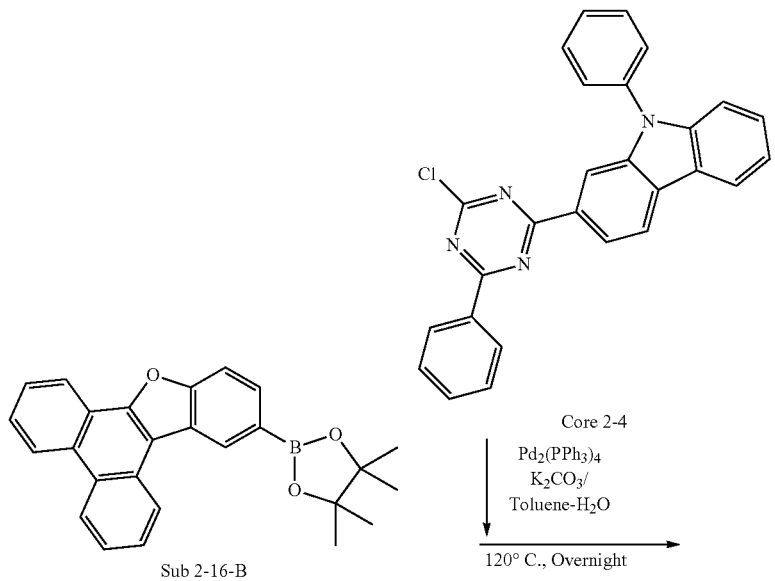

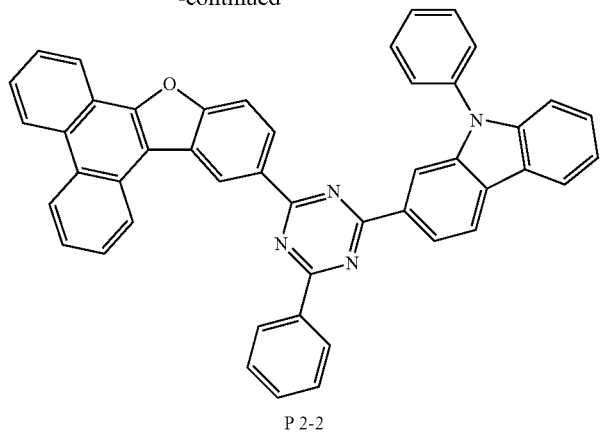

P 2-2

(1) Synthesis of Sub 2-16-B

Sub 2-16 (5.0 g, 16.5 mmol), bis(pinacolato)diboron (6.29 g, 24.8 mmol), Pd$_2$(dba)$_3$ (0.76 g, 0.8 mmol), potassium acetate (4.86 g, 49.5 mmol) and X-phos (0.79 g, 1.7 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO$_4$ and concentrated to obtain 4.69 g (yield: 72%) of the product.

(2) Synthesis of P 2-2

Sub 2-16-B (4.69 g, 11.9 mmol), Core 2-4 (5.15 g, 11.9 mmol), Pd$_2$(PPh$_3$)$_4$ (0.41 g, 0.4 mmol) and K$_2$CO$_3$ (4.93 g, 35.7 mmol) were placed in a round bottom flask. After THF (100 mL) and H$_2$O (50 mL) were added thereto, the mixture was heated to 120° C. and stirred overnight. When the reaction was completed, water in the reaction product was removed and the reaction product was filtered under reduced pressure. The filtrate was dried over MgSO$_4$ and concentrated. Then, a silica gel column and recrystallization were applied to the concentrate to obtain 6.17 g (yield: 78%) of the product.

4. Synthesis Example of P 2-9

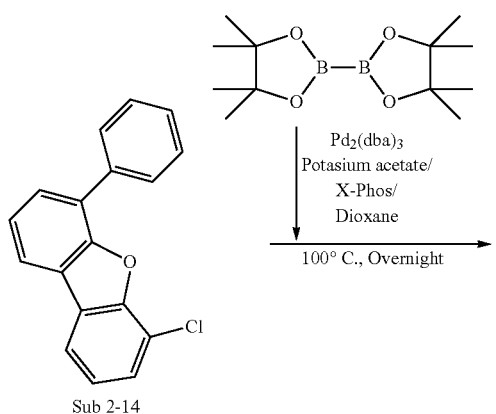

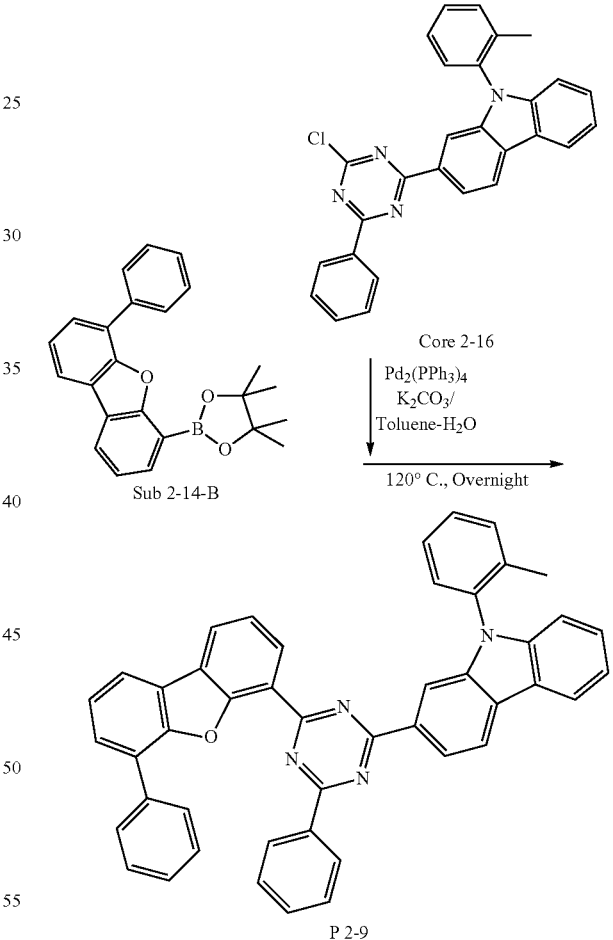

(1) Synthesis of Sub 2-14-B

Sub 2-14 (5.0 g, 17.9 mmol), bis(pinacolato)diboron (6.83 g, 26.9 mmol), Pd$_2$(dba)$_3$ (0.82 g, 0.9 mmol), potassium acetate (5.28 g, 53.8 mmol) and X-phos (0.86 g, 1.8 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO₄ and concentrated to obtain 4.58 g (yield: 69%) of the product.

(2) Synthesis of P 2-9

Sub 2-14-B (4.69 g, 12.7 mmol), Core 2-16 (5.48 g, 12.7 mmol), Pd₂(PPh₃)₄ (0.44 g, 0.4 mmol) and K₂CO₃ (5.25 g, 38.0 mmol) were placed in a round bottom flask. After THF (100 mL) and H₂O (50 mL) were added thereto, the mixture was heated to 120° C. and stirred overnight. When the reaction was completed, water in the reaction product was removed and the reaction product was filtered under reduced pressure. The filtrate was dried over MgSO₄ and concentrated. Then, a silica gel column and recrystallization were applied to the concentrate to obtain 6.72 g (yield: 81%) of the product.

5. Synthesis Example of P 3-5

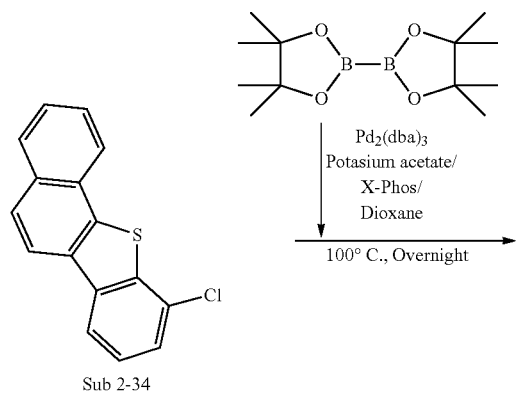

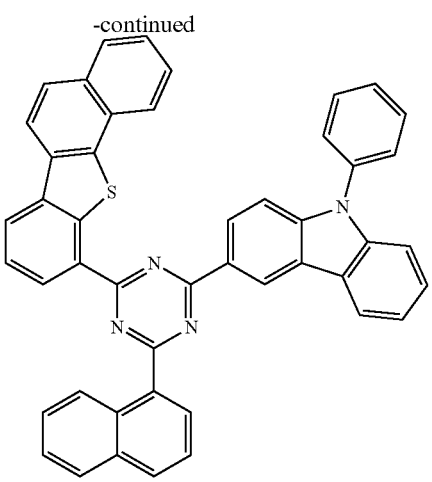

P 3-5

(1) Synthesis of Sub 2-34-B

Sub 2-34 (5.0 g, 18.6 mmol), bis(pinacolato)diboron (7.09 g, 27.9 mmol), Pd₂(dba)₃ (0.85 g, 0.9 mmol), potassium acetate (5.48 g, 55.8 mmol) and X-phos (0.89 g, 1.9 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO₄ and concentrated to obtain 4.49 g (yield: 67%) of the product.

(2) Synthesis of P 3-5

Sub 2-34-B (4.49 g, 12.5 mmol), Core 2-19 (6.02 g, 12.5 mmol), Pd₂(PPh₃)₄ (0.43 g, 0.4 mmol) and K₂CO₃ (5.17 g, 37.4 mmol) were placed in a round bottom flask. After THF (100 mL) and H₂O (50 mL) were added thereto, the mixture was heated to 120° C. and stirred overnight. When the reaction was completed, water in the reaction product was removed and the reaction product was filtered under reduced pressure. The filtrate was dried over MgSO₄ and concentrated. Then, a silica gel column and recrystallization were applied to the concentrate to obtain 7.72 g (yield: 91%) of the product.

6. Synthesis Example of P 4-8

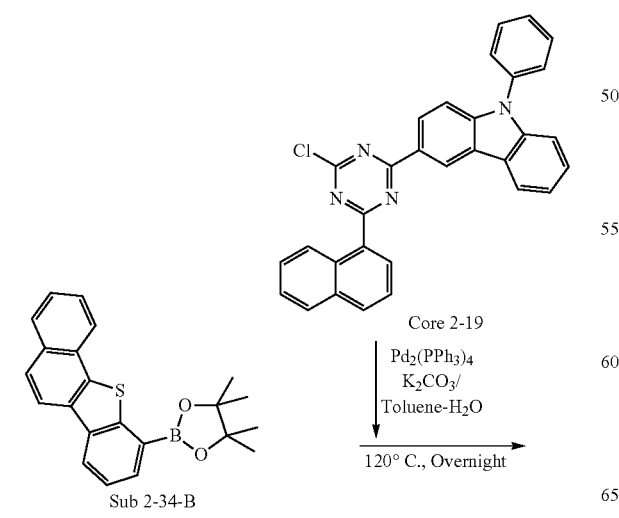

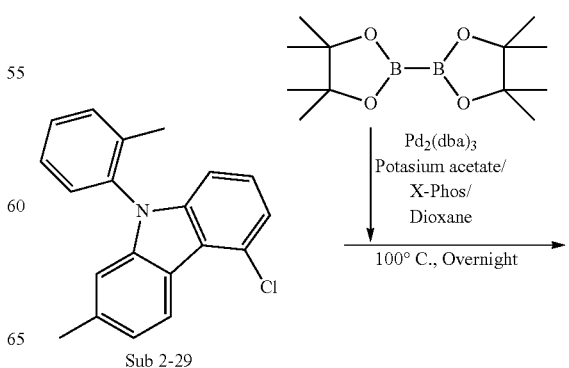

-continued

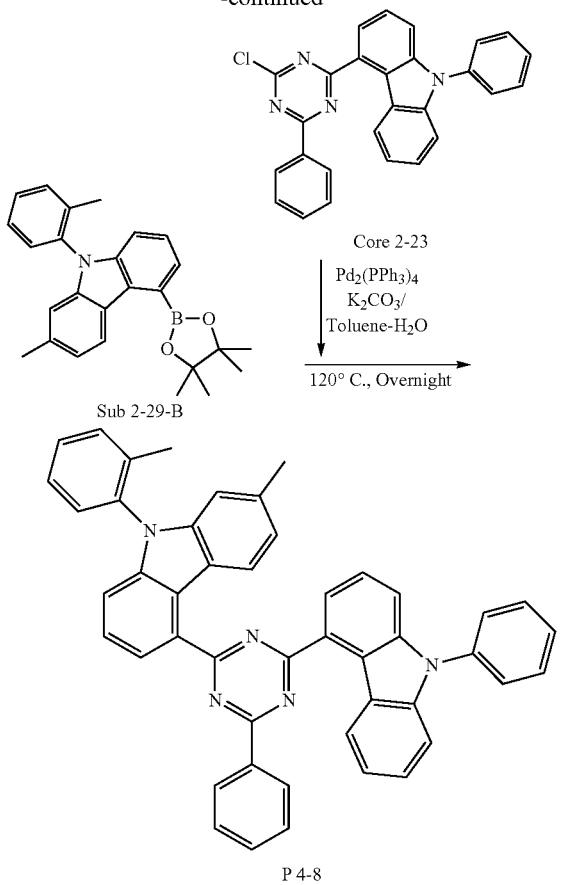

(1) Synthesis of Sub 2-29-B

Sub 2-29 (5.0 g, 16.4 mmol), bis(pinacolato)diboron (6.23 g, 24.5 mmol), Pd$_2$(dba)$_3$ (0.75 g, 0.8 mmol), potassium acetate (4.81 g, 49.1 mmol) and X-phos (0.78 g, 1.6 mmol) were placed in a round bottom flask. After dioxane (100 mL) was added thereto, the mixture was stirred overnight at 100° C. When the reaction was completed, the reaction product was quenched by adding water. Water in the reaction product was removed and the reaction product was filtered under reduced pressure. An organic layer was dried over MgSO$_4$ and concentrated to obtain 5.26 g (yield: 81%) of the product.

(2) Synthesis of P 4-8

Core 2-23 (5.73 g, 13.2 mmol), Pd$_2$(PPh$_3$)$_4$ (0.46 g, 0.4 mmol) and K$_2$CO$_3$ (5.49 g, 39.7 mmol) were added to Sub 2-29-B (5.26 g, 13.2 mmol) and THF (100 mL) and H$_2$O (50 mL) were added thereto. Then, the mixture was heated to 120° C. and stirred overnight. When the reaction was completed, water in the reaction product was removed and the reaction product was filtered under reduced pressure. The filtrate was dried over MgSO$_4$ and concentrated. Then, a silica gel column and recrystallization were applied to the concentrate to obtain 7.51 g (yield: 85%) of the product.

Fabrication and Evaluation of Organic Electric Element

Example 1

Green OLED (Host)

On the ITO layer (anode) formed on the glass substrate, N$^1$-(naphthalen-2-yl)-N$^4$,N$^4$-bis(4-(naphthalen-2-yl(phenyl) amino)phenyl)-N$^1$-phenylbenzene-1,4-diamine (hereinafter, abbreviated as "2-TNATA") was vacuum deposited to a thickness of 60 nm to form a hole injection layer, and then 4,4-bis[N-(1-naphthyl)-N-phenylamino]biphenyl (hereinafter abbreviated as "NPB") was vacuum deposited to a thickness of 60 nm to form a hole transport layer.

Thereafter, a light emitting layer having a thickness of 30 nm was deposited on the hole transport layer by using the compound P 1-1 of the present invention as a host material, [tris(2-phenylpyridine)-iridium] (hereinafter, abbreviated as "(Ir(ppy)$_3$") as a dopant material, wherein the dopant was doped so that the weight ratio of the host and the dopant was 95:5.

Next, (1,1'-biphenyl-4-olato)bis(2-methyl-8-quinolinolato)aluminum (hereinafter, "BAlq") was vacuum-deposited to a thickness of 10 nm on the light emitting layer to form a hole blocking layer, and tris(8-quinolinolato)aluminum (hereinafter, "Alq$_3$") was vacuum-deposited to a thickness of 40 nm on the hole blocking layer to form a an electron transport layer.

Thereafter, LiF was deposited to a thickness of 0.2 nm to form an electron injection layer on the electron transport layer, and then Al was deposited to a thickness of 150 nm to form a cathode on the electron injection layer.

[Example 2] to [Example 16]

The organic electroluminescent elements were manufactured in the same manner as described in Example 1 except that compounds of the present invention described in the following Table 4 instead of compound P 1-1 of the present invention were used as host material of the light emitting layer.

Comparative Example 1

The organic electroluminescent element was manufactured in the same manner as described in Example 1 except that the following Comparative Compound A instead of compound P 1-1 of the present invention was used as host material of the light emitting layer.

<Comparative Compound A>

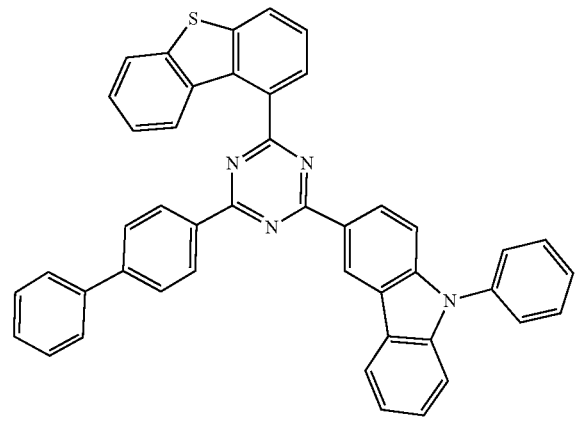

Electroluminescence (EL) characteristics were measured with PR-650 (Photo research) by applying a forward bias DC voltage to the organic electroluminescent elements prepared in Examples 1 to 16 of the present invention and Comparative Example 1. The T95 life time was measured using a life time measuring apparatus manufactured by mc science Inc. at reference brightness of 5000 cd/m$^2$. The measurement results are shown in Table 4.

TABLE 4

| Compound | | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| comp.Ex(1) | comp.Com A | 5.5 | 21.7 | 5000.0 | 23.0 | 60.8 | 0.34 | 0.62 |
| Ex.(1) | P 1-1 | 4.5 | 14.7 | 5000.0 | 33.9 | 86.6 | 0.32 | 0.65 |
| Ex.(2) | P 1-6 | 5.0 | 16.5 | 5000.0 | 30.3 | 92.3 | 0.31 | 0.61 |
| Ex.(3) | P 1-11 | 4.9 | 16.2 | 5000.0 | 30.9 | 95.9 | 0.31 | 0.62 |
| Ex.(4) | P 1-13 | 4.6 | 12.7 | 5000.0 | 39.5 | 85.4 | 0.34 | 0.64 |
| Ex.(5) | P 2-4 | 4.6 | 12.7 | 5000.0 | 39.5 | 81.0 | 0.30 | 0.62 |
| Ex.(6) | P 2-8 | 4.5 | 13.3 | 5000.0 | 37.6 | 85.8 | 0.32 | 0.64 |
| Ex.(7) | P 2-11 | 4.5 | 12.7 | 5000.0 | 39.3 | 83.8 | 0.31 | 0.63 |
| Ex.(8) | P 2-13 | 4.6 | 12.6 | 5000.0 | 39.8 | 85.6 | 0.35 | 0.64 |
| Ex.(9) | P 3-4 | 4.5 | 12.7 | 5000.0 | 39.3 | 87.4 | 0.35 | 0.60 |
| Ex.(10) | P 3-5 | 4.9 | 16.1 | 5000.0 | 31.0 | 94.9 | 0.30 | 0.63 |
| Ex.(11) | P 3-9 | 4.7 | 12.7 | 5000.0 | 39.5 | 88.9 | 0.34 | 0.63 |
| Ex.(12) | P 3-12 | 4.8 | 16.0 | 5000.0 | 31.3 | 95.8 | 0.34 | 0.62 |
| Ex.(13) | P 4-3 | 4.5 | 12.7 | 5000.0 | 39.3 | 89.7 | 0.35 | 0.64 |
| Ex.(14) | P 4-7 | 5.0 | 15.9 | 5000.0 | 31.4 | 96.6 | 0.31 | 0.64 |
| Ex.(15) | P 4-9 | 4.6 | 12.8 | 5000.0 | 39.1 | 89.1 | 0.33 | 0.64 |
| Ex.(16) | P 4-13 | 4.7 | 13.2 | 5000.0 | 37.7 | 83.7 | 0.31 | 0.61 |

From Table 4, it is can be seen that the luminous efficiency and lifetime of the organic electroluminescent element are significantly improved, and the driving voltage is also lowered according to the embodiment of the present invention, compared to Comparative Example 1. That is, when the compound of the present invention, compared to using comparative compound A, is used as a phosphorescent host, the characteristics of element are significantly improved.

Both Comparative Compound A and the present invention are the same in that carbazole and dibenzothiophen are bound to the triazine, but the compound of the present invention differs in that not all of $R^1$ to $R^4$ in Formula 1 are hydrogen, whereas in Comparative Compound A, all substituents corresponding to $R^1$-$R^4$ are hydrogen.

When at least one of $R^1$ to $R^4$ is a substituent other than hydrogen, like the compound of the present invention, the conjugation length is longer than that of Comparative Compound A in which all of substituents corresponding to $R^1$ to $R^4$ are hydrogen. As a result, it seems that the driving voltage is lowered because the hole mobility becomes faster. In addition, as substituent(s) other than hydrogen is(are) substituted for $R^1$ to $R^4$, the active-site of the compound is stabilized. As a result, in the process of depositing the compound during device manufacturing, the probability of occurrence of denaturation and side-products is lowered, and stability is also improved. In addition, when at least one of $R^1$ to $R^4$ is a substituent other than hydrogen, the process temperature is lowered during purification, and thus a great advantage occurs in terms of process cost.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

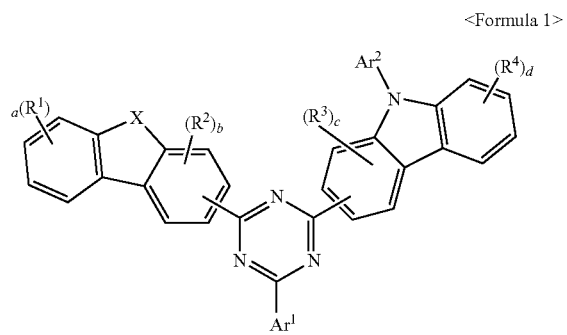

<Formula 1> wherein:

X is O or S, $R^1$ to $R^4$ are each independently selected from the group consisting of hydrogen, deuterium, halogen, a cyano group, a nitro group, a $C_6$ aryl group, a $C_3$-$C_{60}$ aliphatic ring group, a $C_1$ alkyl group, a $C_2$-$C_{20}$ alkenyl group, a $C_2$-$C_{20}$ alkynyl group, a $C_1$-$C_{30}$ alkoxy group, and a $C_6$-$C_{30}$ aryloxy group, and adjacent groups thereof may be bonded to each other to form a ring, with the proviso that at least one of $R^3$ and $R^4$ is not hydrogen nor deuterium, or at least one of $R^1$ to $R^4$ forms a ring with an adjacent group thereof, a and d are each an integer of 0 to 4, b and c are each an integer of 0 to 3, $Ar^1$ and $Ar^2$ are independently selected from the group consisting of a $C_6$-$C_{60}$ aryl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group.

2. The compound of claim 1, wherein Formula 1 is represented by one of Formula 2 to Formula 5:

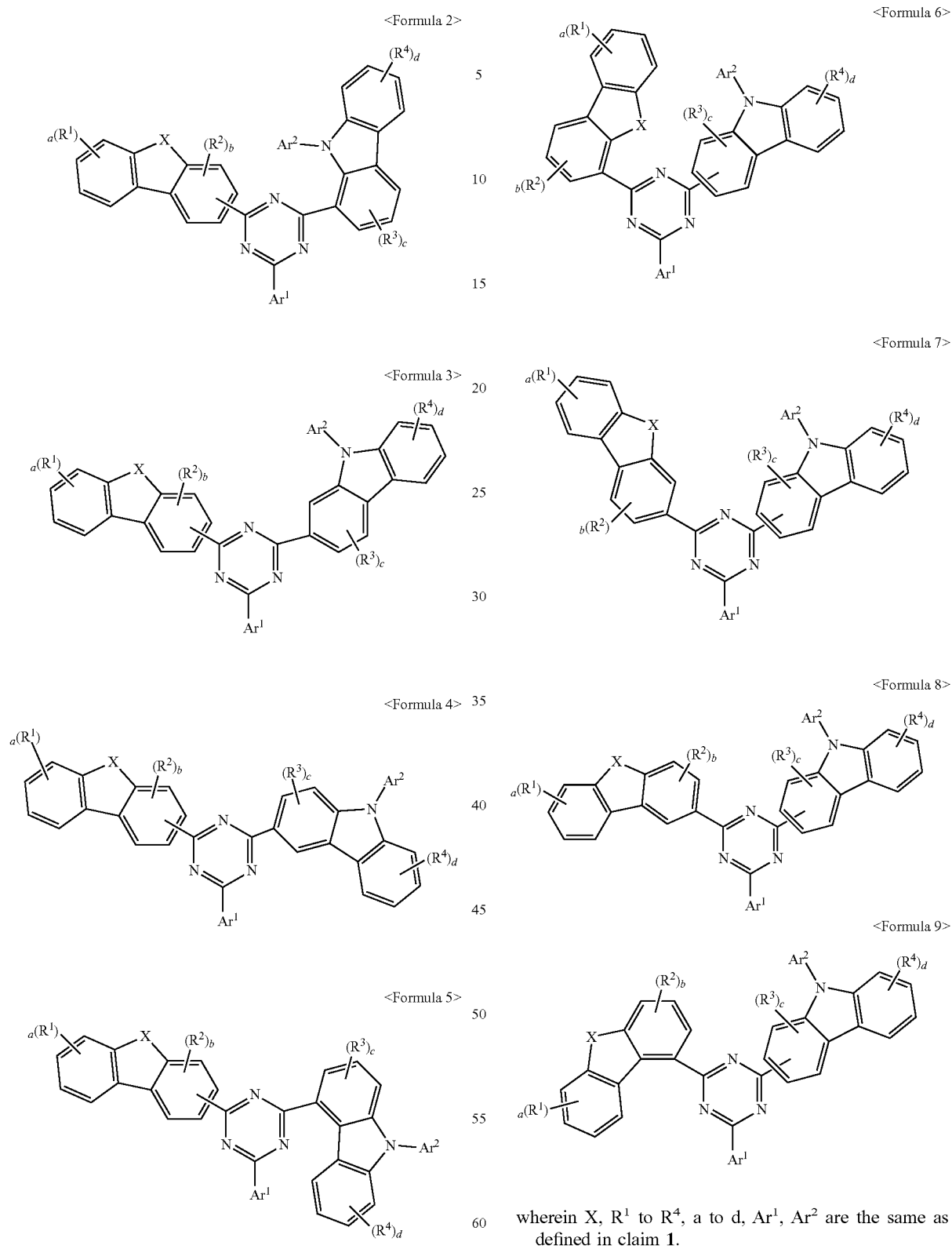

wherein X, $R^1$ to $R^4$, a to d, $Ar^1$, $Ar^2$ are the same as defined in claim 1.

3. The compound of claim 1, wherein Formula 1 is represented by one of Formula 6 to Formula 9:

wherein X, $R^1$ to $R^4$, a to d, $Ar^1$, $Ar^2$ are the same as defined in claim 1.

4. The compound of claim 1, wherein at least one of $R^1$ to $R^4$ is a Ce aryl group.

5. The compound of claim 1, wherein $R^1$ is not hydrogen.

6. A compound selected from the group consisting of the following compounds:

P 1-1
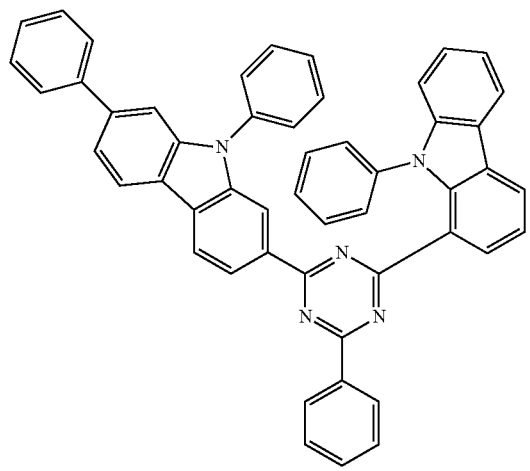
P 1-2
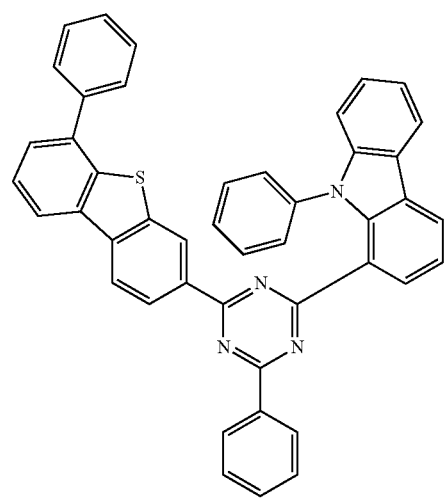
P 1-3
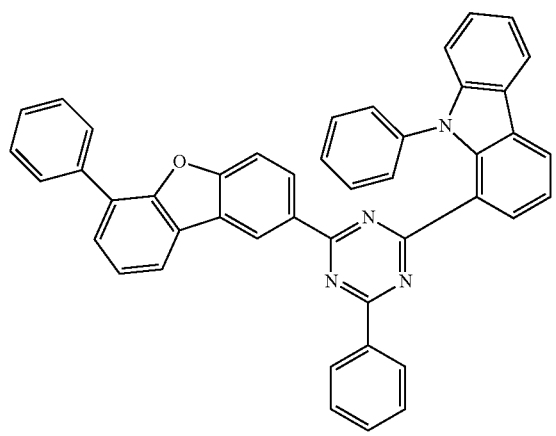
-continued
P 1-4
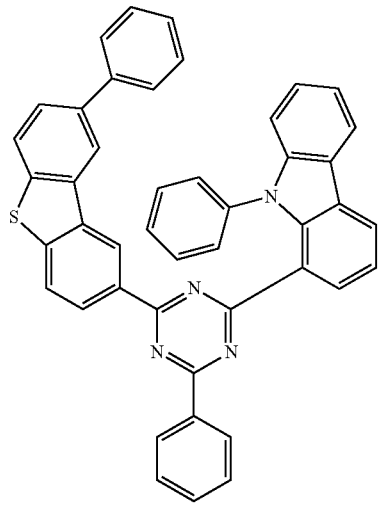
P 1-5
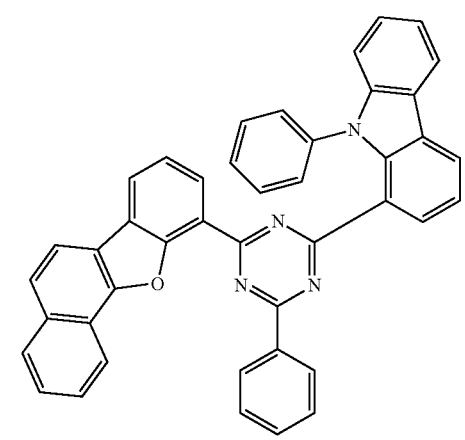
P 1-6
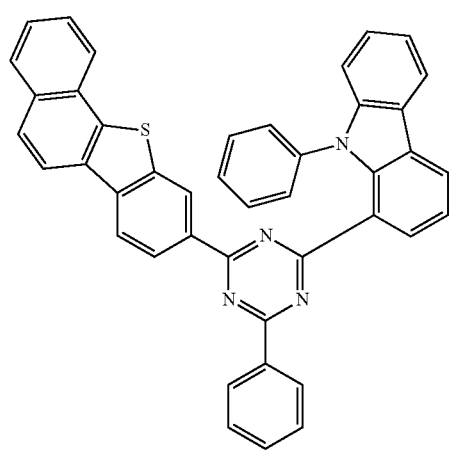

P 1-7
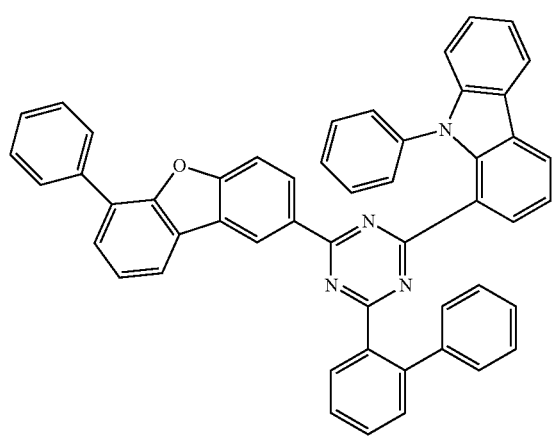
P 1-10
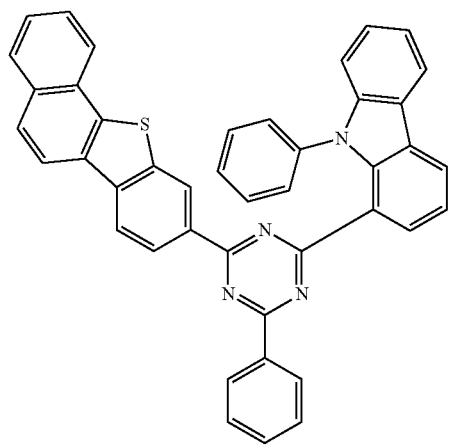
P 1-8
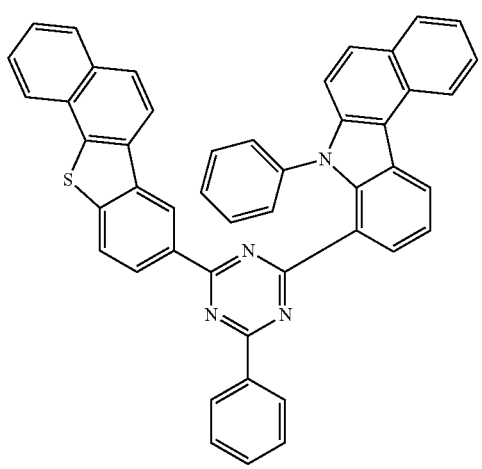
P 1-11
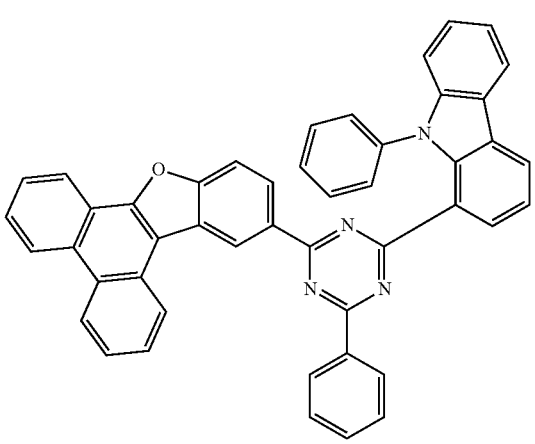
P 1-9
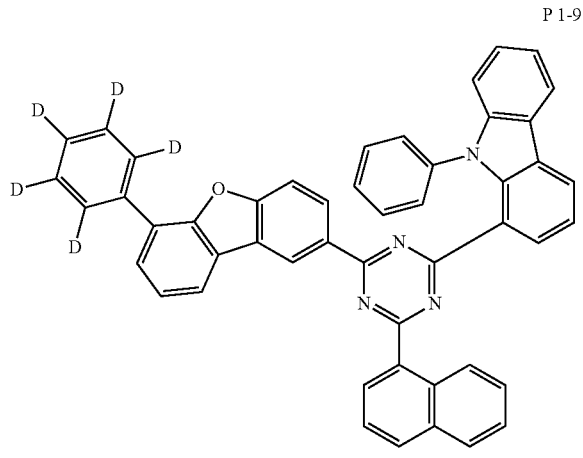
P 1-12
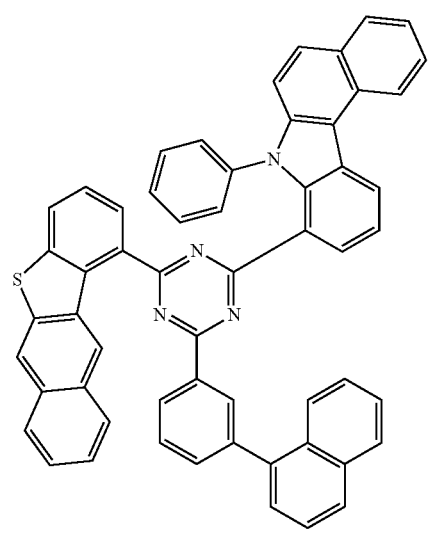

P 1-13
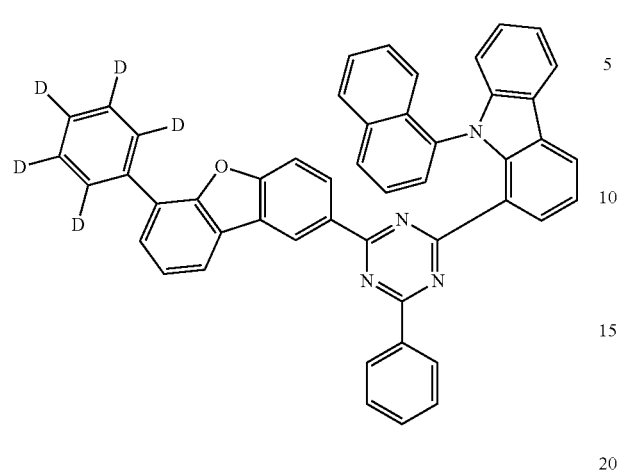
P 1-16
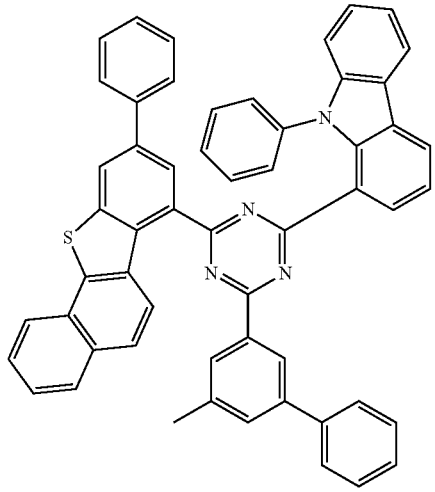
P 1-14
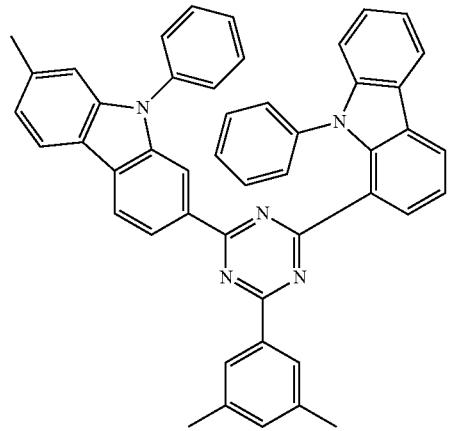
P 2-1
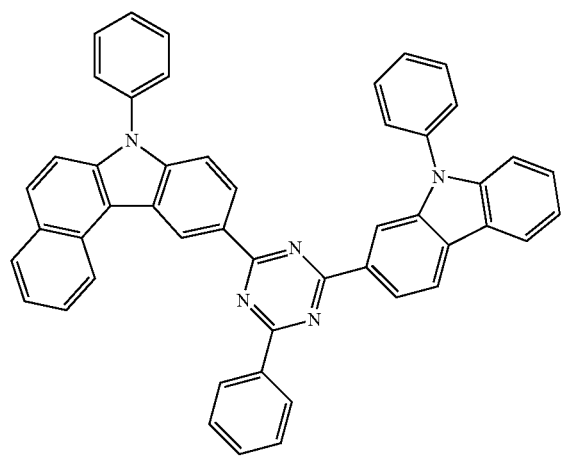
P 1-15
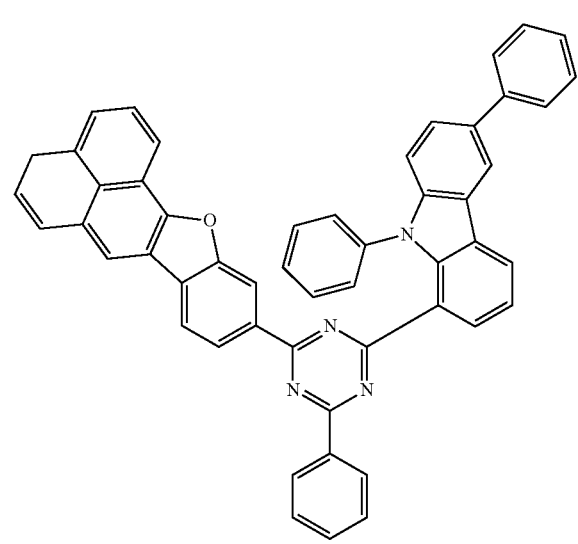
P 2-2
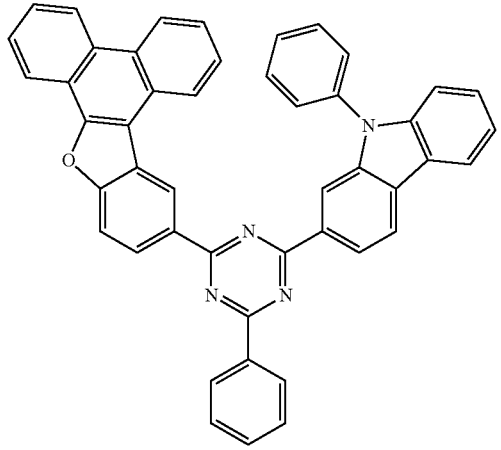

P 2-3
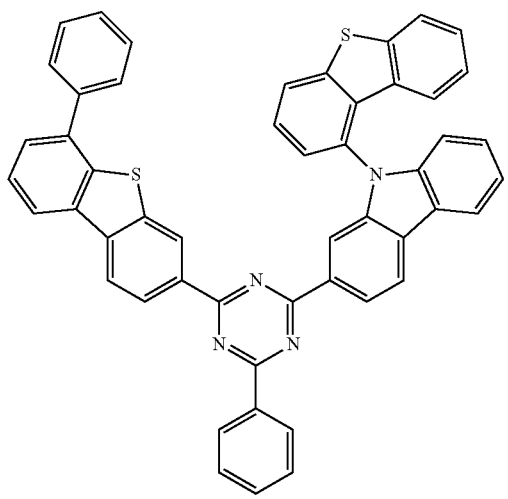
P 2-4
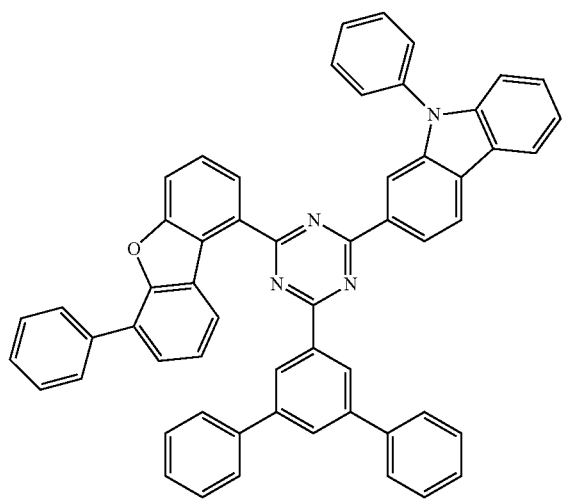
P 2-5
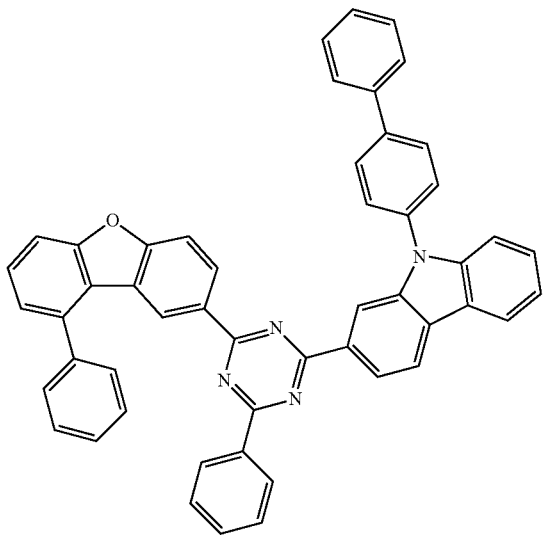
P 2-6
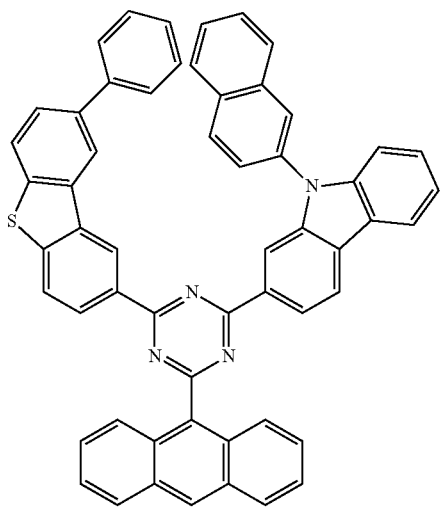
P 2-7
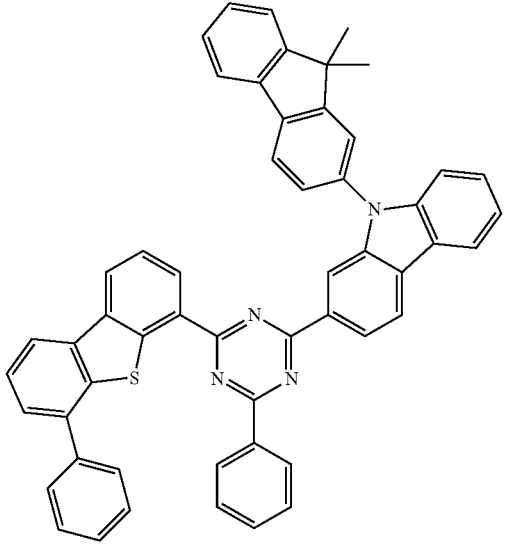
P 2-8
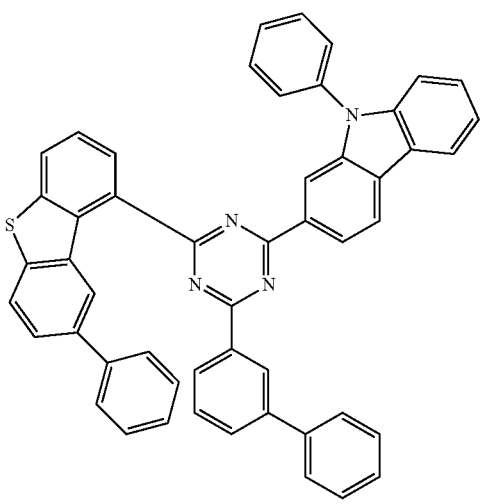

-continued
P 2-9
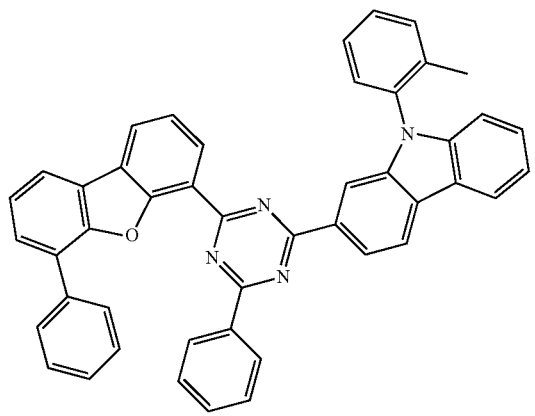
P 2-10
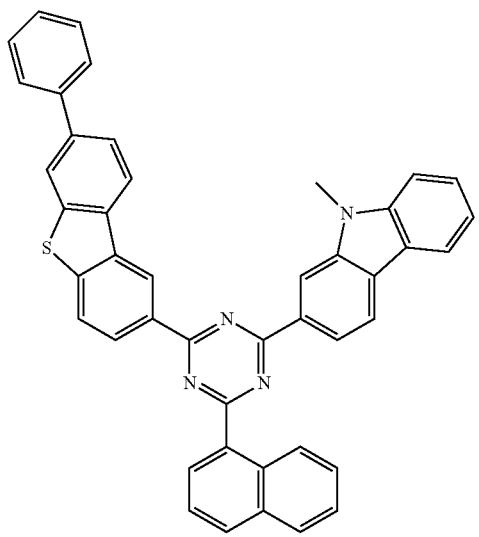
P 2-11
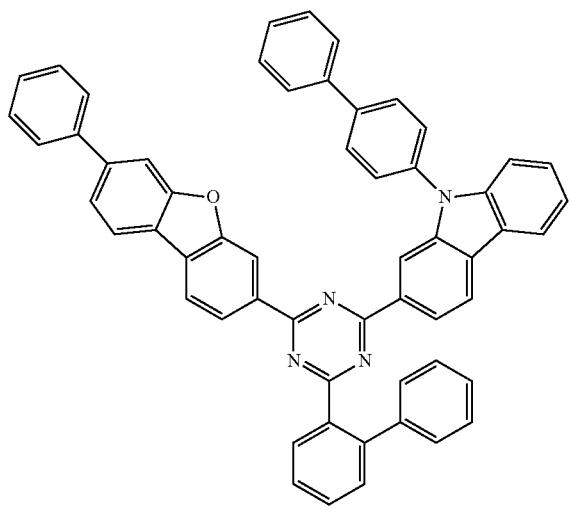
P 2-13
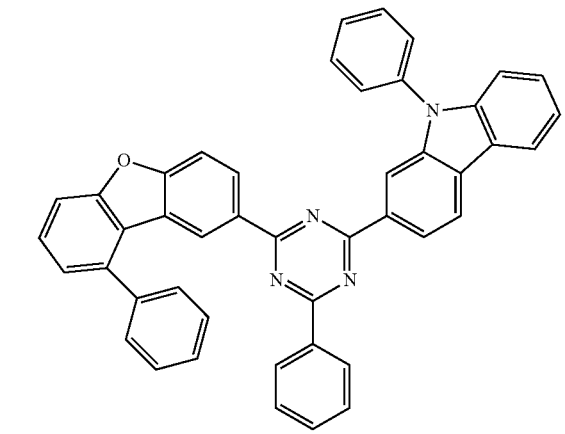
P 2-14
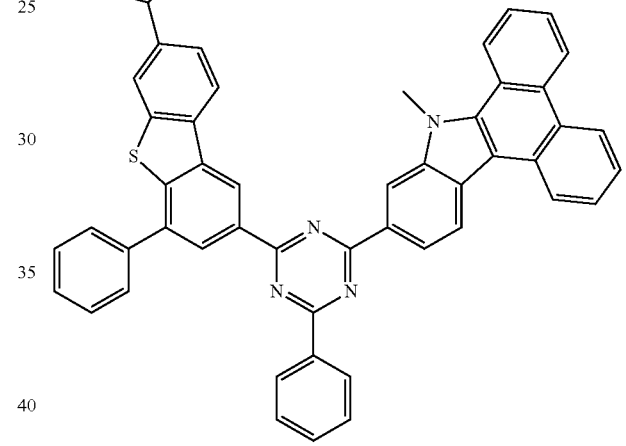
P 2-15
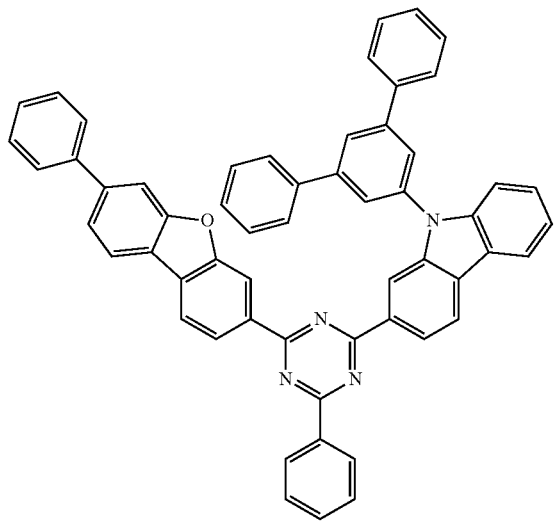

P 2-16
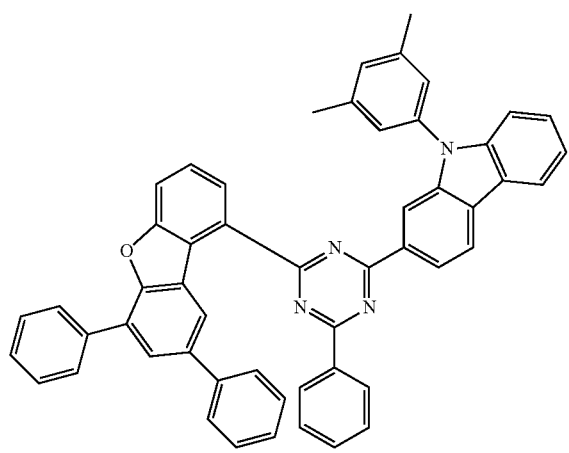
P 3-3
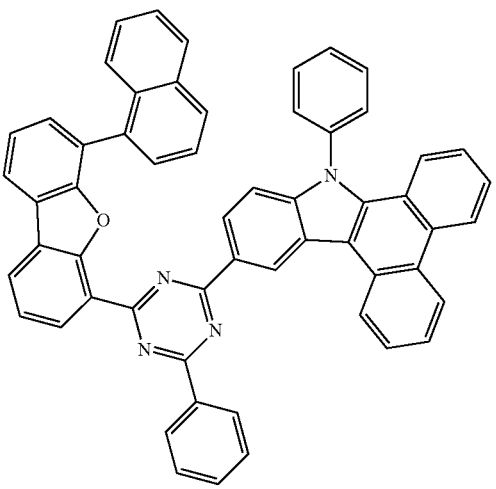
P 3-1
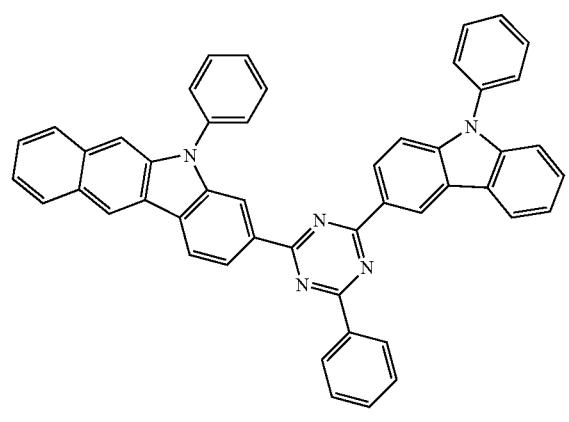
P 3-4
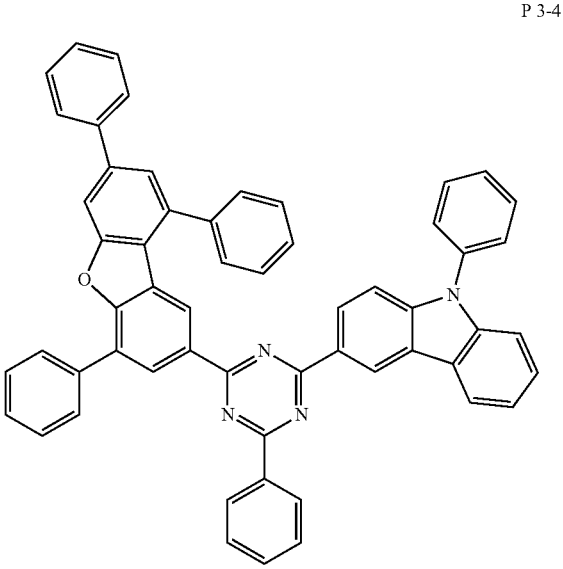
P 3-2
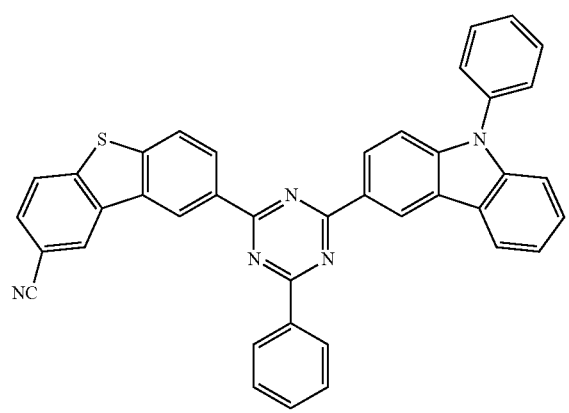
P 3-5
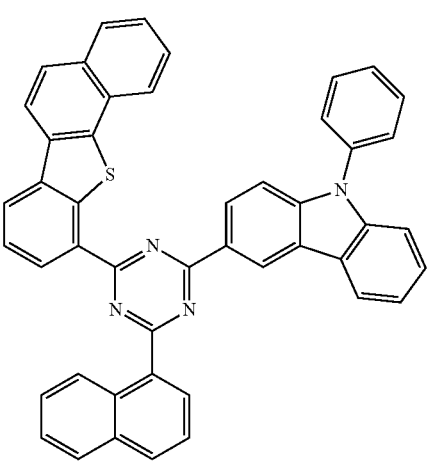

P 3-6
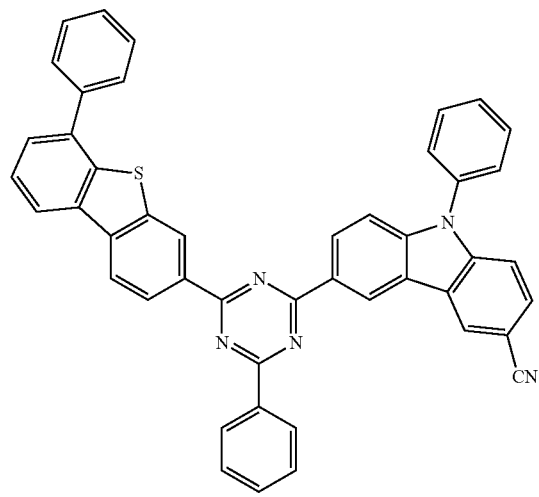
P 3-7
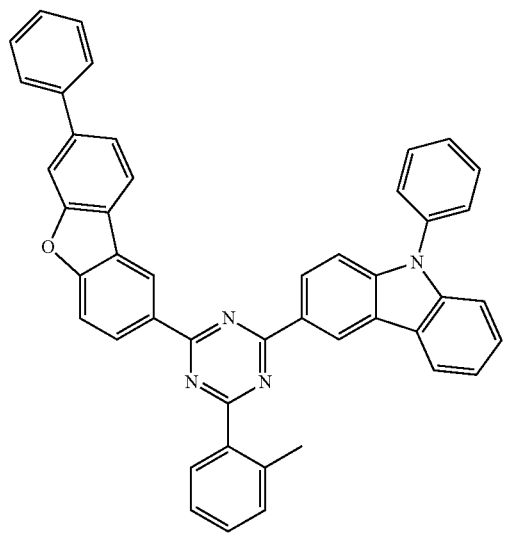
P 3-8
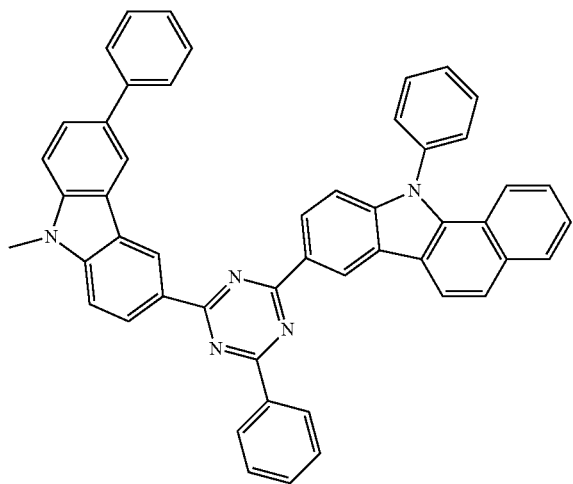
P 3-9
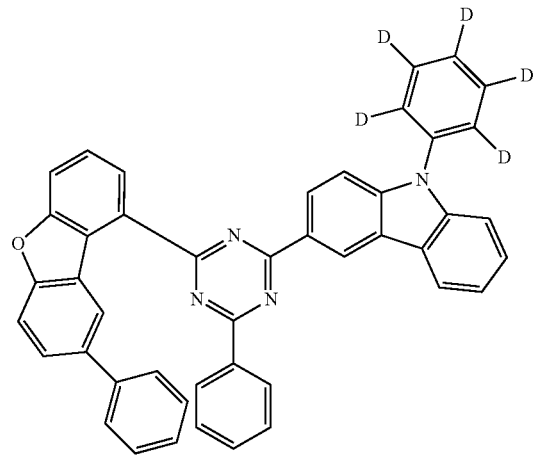
P 3-10
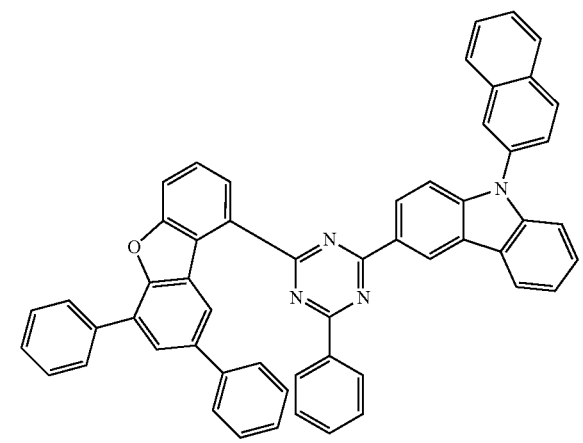
P 3-11
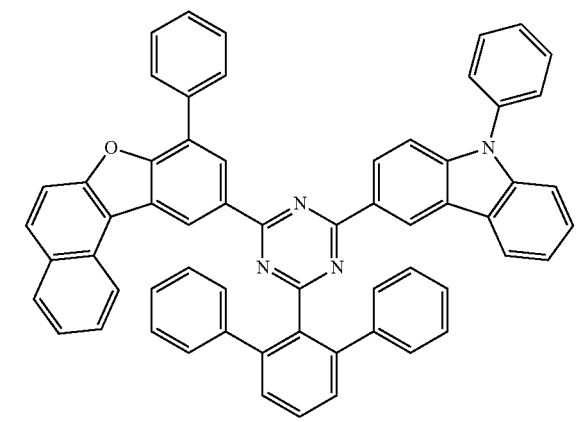

P 3-12
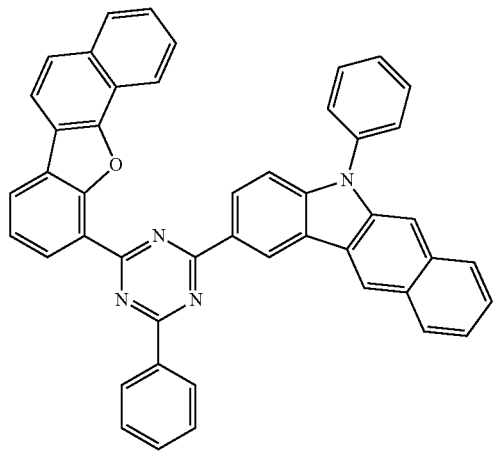
P 4-3
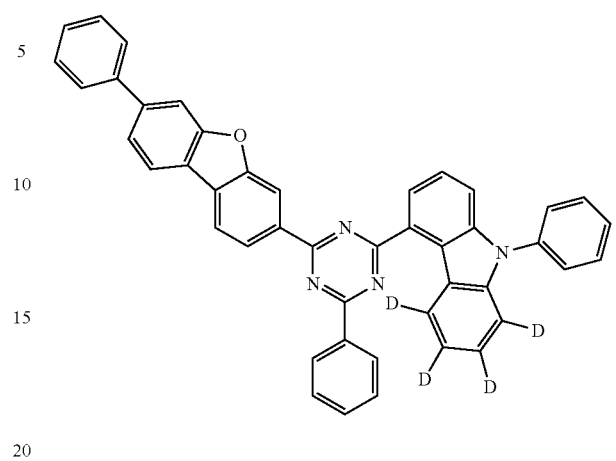
P 4-1
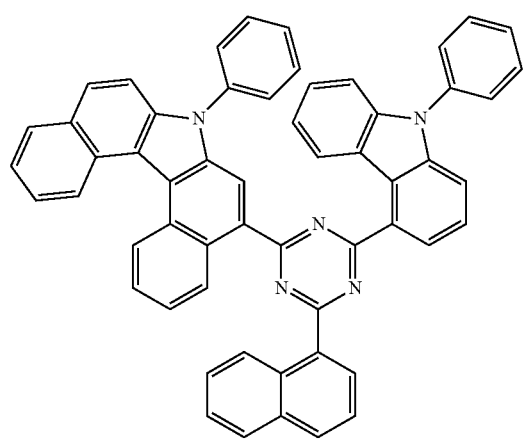
P 4-4
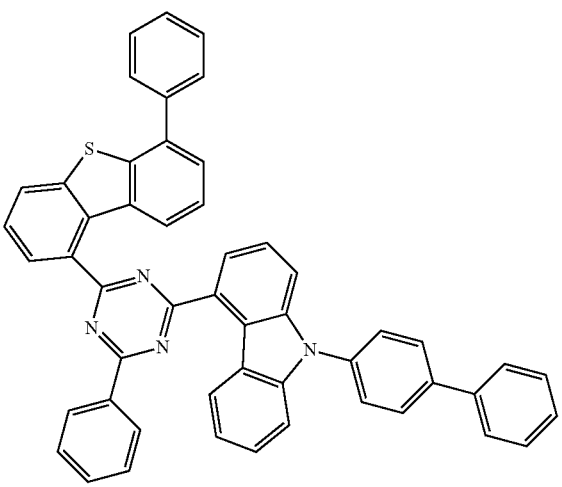
P 4-2
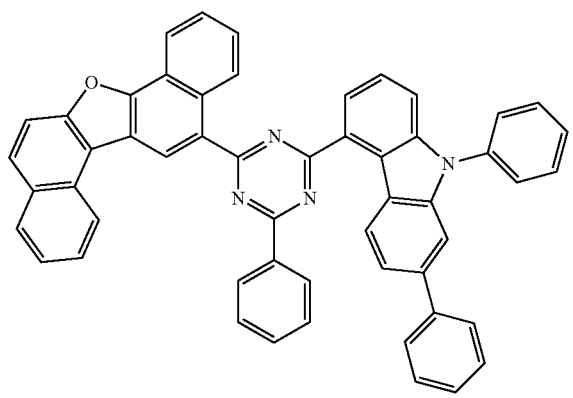
P 4-5
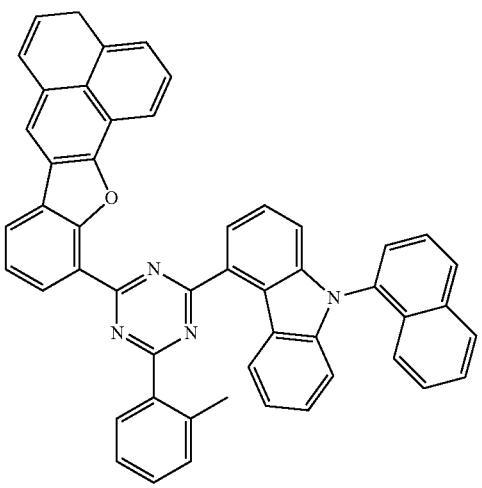

P 4-6
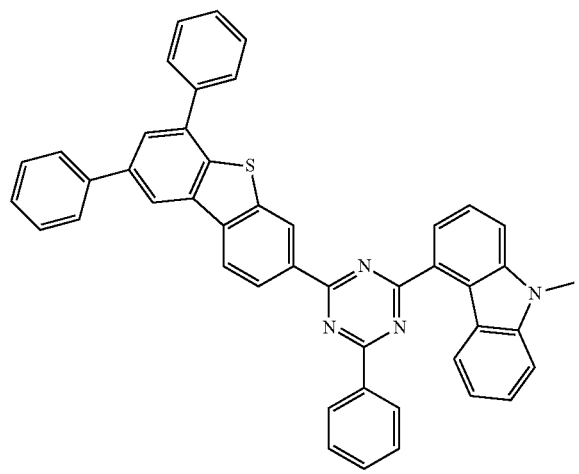
P 4-7
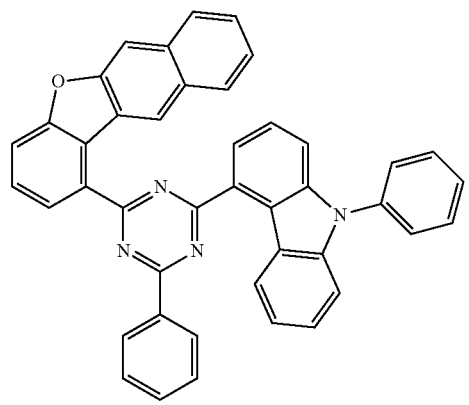
P 4-8
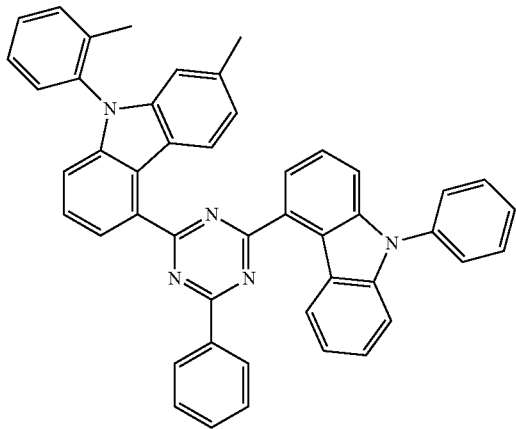
P 4-9
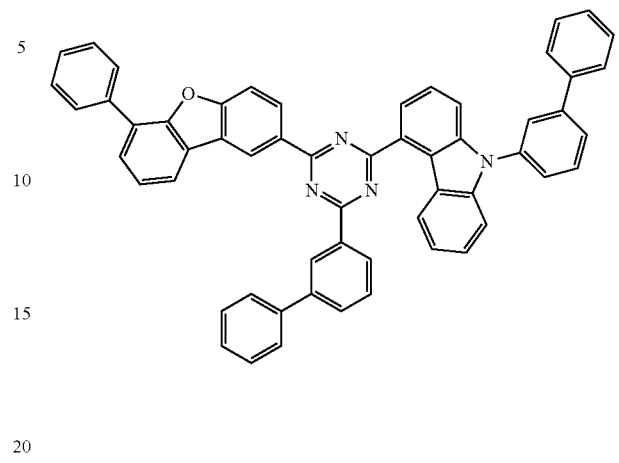
P 4-10
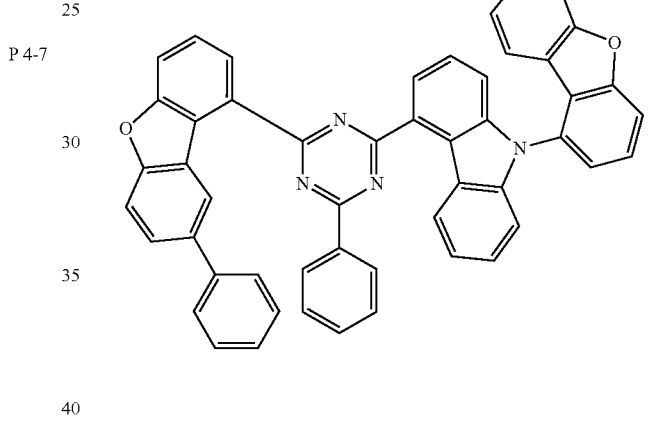
P 4-11
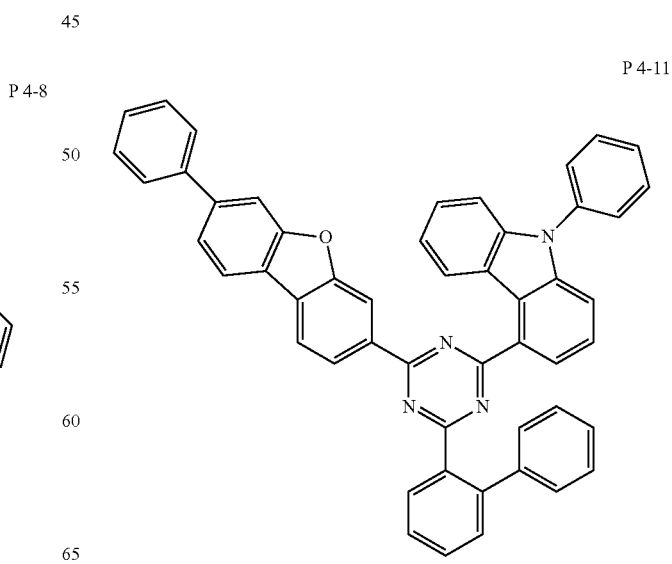

121
-continued

P 4-12

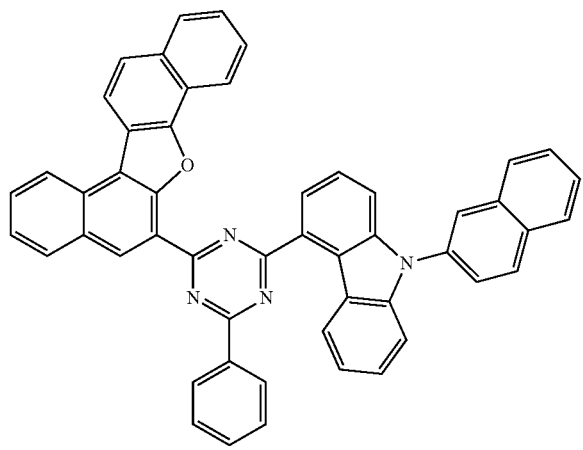

P 4-13

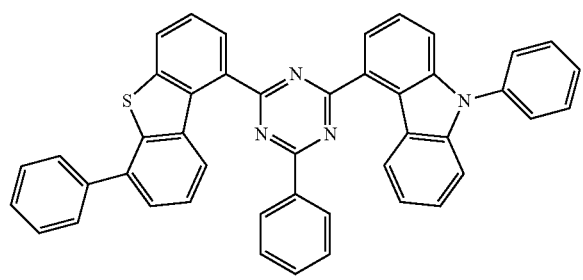

P 4-14

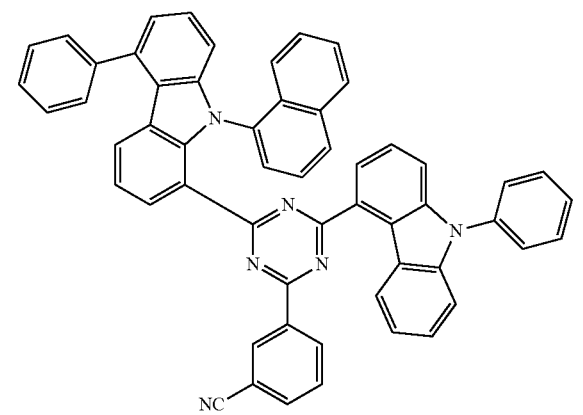

P 4-15

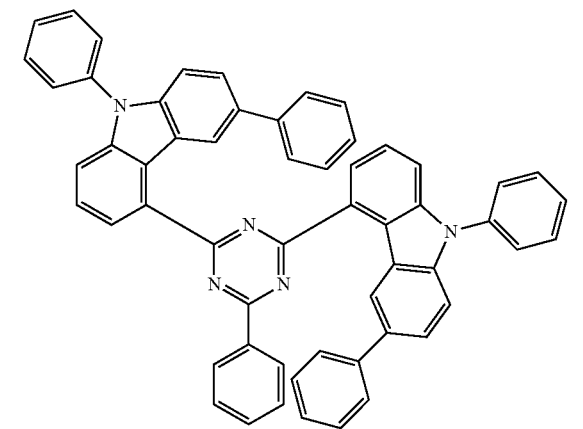

122
-continued

P 4-16

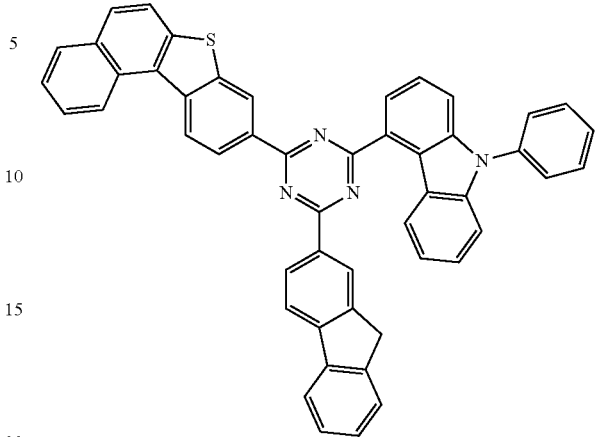

7. An organic electric element comprising a first electrode, a second electrode, and an organic material layer formed between the first electrode and the second electrode, wherein the organic material layer comprises a single compound or two or more compounds of claim 6.

8. An electronic device comprising a display device and a control unit for driving the display device, wherein the display device comprises the organic electric element of claim 7.

9. An organic electric element comprising a first electrode, a second electrode, and an organic material layer formed between the first electrode and the second electrode, wherein the organic material layer comprises a single compound or two or more compounds represented by Formula 1 of claim 1.

10. The organic electric element of claim 9, wherein the organic material layer comprises at least one of a hole injection layer, a hole transport layer, an emission-auxiliary layer, a light emitting layer, an electron transport-auxiliary layer, an electron transport layer, and an electron injection layer.

11. The organic electric element of claim 10, wherein the compound is comprised in the light emitting layer.

12. An electronic device comprising a display device and a control unit for driving the display device, wherein the display device comprises the organic electric element of claim 9.

13. The electronic device of claim 12, wherein the organic electric element is selected from the group consisting of an organic electroluminescent element, an organic solar cell, an organic photo conductor, an organic transistor, an element for monochromatic illumination and element for quantum dot display.

* * * * *